US010004826B2

(12) United States Patent
Bhatia et al.

(10) Patent No.: US 10,004,826 B2
(45) Date of Patent: Jun. 26, 2018

(54) IMPLANTABLE HUMAN LIVER TISSUE CONSTRUCTS AND USES THEREOF

(75) Inventors: Sangeeta N. Bhatia, Lexington, MA (US); Alice A. Chen, Boston, MA (US); Shengyong Ng, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 127 days.

(21) Appl. No.: 13/267,866

(22) Filed: Oct. 6, 2011

(65) Prior Publication Data

US 2012/0216304 A1 Aug. 23, 2012

Related U.S. Application Data

(60) Provisional application No. 61/390,465, filed on Oct. 6, 2010.

(51) Int. Cl.
*A61L 33/18* (2006.01)
*A61L 27/36* (2006.01)
*A61L 27/18* (2006.01)
*A61L 27/38* (2006.01)
*C12N 5/071* (2010.01)
*C12N 5/00* (2006.01)
*A01K 67/027* (2006.01)
*G01N 33/50* (2006.01)

(52) U.S. Cl.
CPC ...... *A61L 27/3604* (2013.01); *A01K 67/0271* (2013.01); *A61L 27/18* (2013.01); *A61L 27/362* (2013.01); *A61L 27/3804* (2013.01); *A61L 27/3886* (2013.01); *C12N 5/0062* (2013.01); *C12N 5/0671* (2013.01); *G01N 33/5088* (2013.01); *A01K 2207/15* (2013.01); *A01K 2267/035* (2013.01); *C12N 2502/13* (2013.01); *C12N 2533/30* (2013.01); *C12N 2533/50* (2013.01); *C12N 2533/74* (2013.01); *G01N 2500/10* (2013.01)

(58) Field of Classification Search
CPC .................................................. A61L 2430/28
See application file for complete search history.

(56) References Cited

U.S. PATENT DOCUMENTS

| | | | |
|---|---|---|---|
| 5,123,950 A | 6/1992 | Homma et al. | |
| 6,368,612 B1 | 4/2002 | Lanza et al. | |
| 6,509,514 B1 | 1/2003 | Kneteman et al. | |
| 6,864,402 B1 | 3/2005 | Rogler et al. | |
| 6,995,299 B2 | 2/2006 | Wu et al. | |
| 7,273,963 B2 | 9/2007 | Kneteman et al. | |
| 7,498,479 B2 | 3/2009 | Kneteman et al. | |
| 7,626,075 B2 | 12/2009 | Beschorner et al. | |
| 2002/0182633 A1* | 12/2002 | Chen | B82Y 5/00 435/7.1 |
| 2009/0035855 A1* | 2/2009 | Ying | A61L 27/3633 435/377 |

FOREIGN PATENT DOCUMENTS

| | | |
|---|---|---|
| EP | 1500697 A2 | 1/2005 |
| EP | 1939280 A1 | 7/2008 |
| WO | 94/08570 A1 | 4/1994 |
| WO | 08/148026 A1 | 12/2008 |
| WO | 2012/048170 A2 | 4/2012 |

OTHER PUBLICATIONS

Seo et al. (2007, Biomaterials, vol. 27, pp. 1487-1495).*
Transparent Inc. (EP 1 939 280 A1, published Feb. 7, 2008).*
Mei et al. (2009, Cell Transplantation, vol. 18, pp. 101-110).*
Cho et al. (2009, Biomedical Materials, vol. 4, pp. 1-7).*
Arcaute et al. (2006, Annals of Biomedical Engineering, vol. 34(9), pp. 1429-1441).*
Chan et al. (2010, Lab Chip, vol. 10, pp. 2062-2070).*
Nomi et al. (2002, Molecular Aspects of Med., vol. 23, pp. 463-483).*
Li et al. (2009, Tissue Engineering, vol. 15(8), pp. 2123-2133).*
Underhill et al. (2007, Biomaterials, vol. 28, pp. 256-270).*
Kaji et al. (ePub Jul. 23, 2010, Biochim Biophys Acta, vol. 1810(3), pp. 239-250).*
Matsumura et al. (2004, Transplantation, vol. 77(9), pp. 1357-1365).*
Ulbricht et al., 2014, Biomaterials, vol. 35, pp. 4848-4861.*
Cho et al. (Jan. 2010, Biotechniques, vol. 48(1), pp. 47-52).*
Azuma, Hisaya et al., "Robust expansion of human hepatocytes in Fah-/-/Rag2-/-/Il2rg-/- mice," Nature Biotechnology, vol. 25(8):903-910 (2007).
Bhatia, S.N. et al., "Effect of cell-cell interactions in preservation of cellular phenotype: cocultivation of hepatocytes and nonparenchymal cells," FASEB J., vol. 13:1883-1900 (1999).
Chen, Alice A. et al., "Humanized mice with ectopic artificial liver tissue," PNAS, vol. 108(29):11842-11847 (2011).

(Continued)

*Primary Examiner* — Thaian N Ton
*Assistant Examiner* — David A. Montanari
(74) *Attorney, Agent, or Firm* — Nelson Mullins Riley & Scarborough LLP; Amy E. Mandragouras, Esq.; Ariana D. Harris

(57) ABSTRACT

Engineered human tissue constructs are provided that are suitable for use in making humanized animals for use in pharmaceutical development. Humanized animals having the constructs implanted in vivo are provided. Methods of making and using the tissue-engineered constructs and humanized animals are also provided.

48 Claims, 34 Drawing Sheets

(56) References Cited

OTHER PUBLICATIONS

Chen, Alice A. et al., "Humanized mice with ectopic artificial liver tissue," Supporting Information, retrieved online at: www.pnas.org/cgi/doi/10.1073/pnas.1101791108, pp. 1-6 (2011).
Kaufmann, P.M. et al., "Highly Porous Polymer Matrices as a Three-dimensional Culture System for Hepatocytes," Cell Transplantation, vol. 6(5):463-468 (1997).
Khademhosseini, Ali et al., "Progress in Tissue Engineering," Scientific American, vol. 300:64-71 (2009).
Khetani, Salman R. et al., "Exploring Interactions Between Rat Hepatocytes and Nonparenchymal Cells Using Gene Expression Profiling," Hepatology, vol. 40:545-554 (2004).
Khetani, Salman R. et al., "Microscale culture of human liver cells for drug development," Nature Biotechnology, vol. 26(1):120-126 (2008).
Kneser, Ulrich et al., "Long-term differentiated function of heterotopically transplanted hepatocytes on three-dimensional polymer matrices," J. Biomed. Mater. Res., vol. 47:494-503 (1999).
Levenberg, Shulamit et al., "Engineering vascularized skeletal muscle tissue," Nature Biotechnology, vol. 23(7):879-884 (2005).
Liu, Valerie A. et al., "Three-Dimensional Photopatterning of Hydrogels Containing Living Cells," Biomedical Microdevices, vol. 4(4):257-266 (2002).
Ohashi, Kazuo et al., "Liver Tissue Engineering at Extrahepatic Sites in Mice as a Potential New Therapy for Genetic Liver Diseases," Hepatology, vol. 41:132-140 (2005).
Stevens, Molly M. et al., "In vivo engineering of organs: The bone bioreactor," PNAS, vol. 102(32):11450-11455 (2005).
Tateno, Chise et al., "Near Completely Humanized Liver in Mice Shows Human-Type Metabolic Responses to Drugs," American Journal of Pathology, vol. 165(3):901-912 (2004).
Uyama, Shiro et al., "Hepatocyte Transplantation Using Biodegradable Matrices in Ascorbic Acid-deficient Rats: Comparison with Heterotopically Transplanted Liver Grafts," Transplantation, vol. 71(9):1226-1231 (2001).
Vanbuskirk, Kelley M. et al., "Preerythrocytic, live-attenuated Plasmodium falciparum vaccine candidates by design," PNAS, vol. 106(31):13004-13009 (2009).
Yokoyama, T. et al., "In Vivo Engineering of Metabolically Active Hepatic Tissues in a Neovascularized Subcutaneous Cavity," American Journal of Transplantation, vol. 6:50-59 (2006).
International Search Report for Application No. PCT/US2011/055179, 6 pages, dated May 23, 2012.
International Preliminary Report on Patentability for Application No. PCT/US2011/055179, 12 pages, dated Apr. 9, 2013.
International Search Report and Written Opinion for Application No. PCT/US2011/055179, 17 pages, dated May 23, 2012.
Invitation to Pay Additional Fees, and, Where Applicable, Protest Fee for Application No. PCT/US2011/055179, 5 pages, dated Feb. 13, 2012.

\* cited by examiner

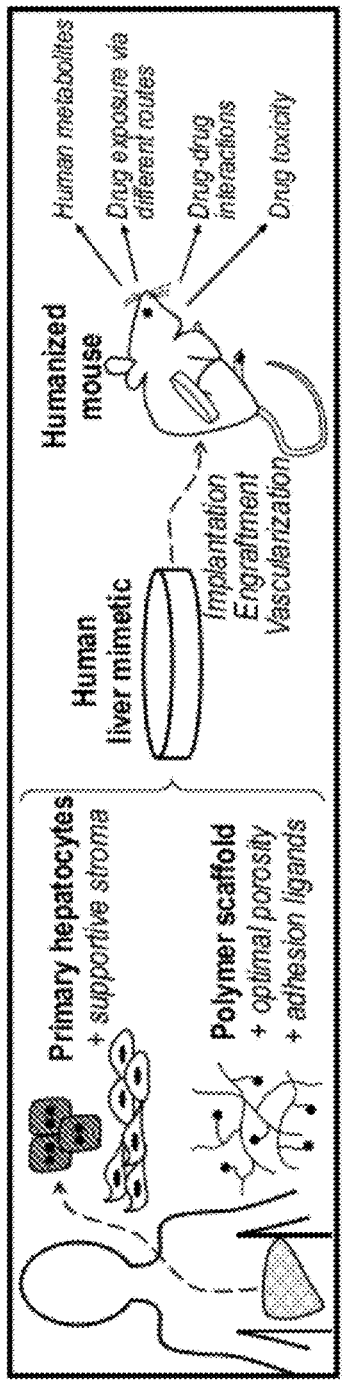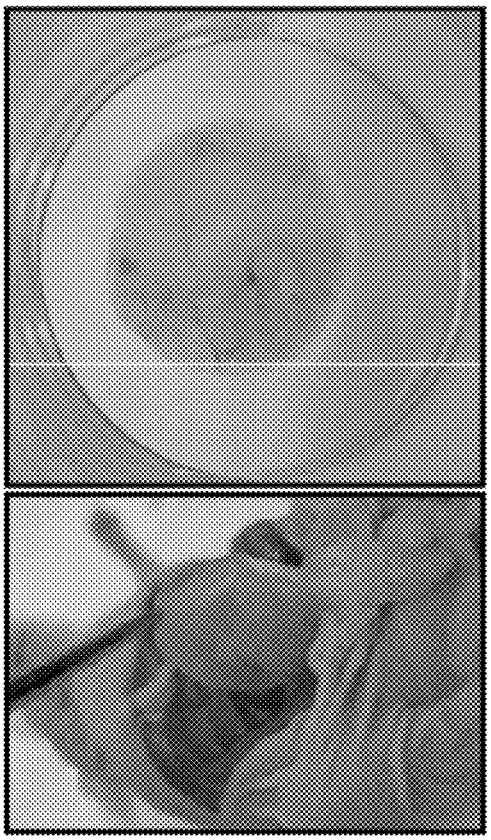
Fig. 1a
Fig. 1ab  Fig. 1c

Fig. 4a Fig. 4b

IMPLANTABLE HUMAN LIVER TISSUE CONSTRUCTS AND USES THEREOF

STATEMENT OF FEDERALLY SPONSORED RESEARCH

This invention was made with government support under grant no. ROI-DK056966-06 6914791 awarded by the National Institutes of Health (NIDDK). The government has certain rights in the invention.

BACKGROUND

In recent years, there has been enormous interest in developing "humanized" mouse models as tools for the study, treatment and prevention of human disease. Humanized mice are typically either immune-deficient mice into which human cells are injected and then coaxed to engraft in vivo via regenerative stimuli, or they may be chimeric mice genetically-engineered to express human genes. The explosion of conference meetings sponsored by both academic and pharmaceutical efforts has highlighting the rapid growth of the humanized mouse field. Within basic research settings, humanized mice have been critical to our understanding of many human biological processes that are not easily recapitulated in cell culture. For example, hematopoietic stem cell engraftment in mouse lymphoid organs has allowed researchers to study dynamics of the human immune system, including responses to infectious diseases that do not infect laboratory animals (See e.g., Baenziger et al. (2006) Proc Natl. Acad. Sci. USA. 103(43): p. 15951-6; Ishikawa et al. (2005) Blood 106(5): p. 1565-73; and Shultz et al. (2007) Nat. Rev. Immunol. 7(2): p. 118-30.). Human tissues implanted into mice have also led to greater understanding of organogenesis, carcinogenesis and metastasis (See e.g., Kuperwasser et al. (2004) Proc. Natl. Acad. Sci. USA. 101(14): p. 4966-71; and Kuperwasser et al. (2005) Cancer Res. 65(14): p. 6130-8.). Within pharmaceutical settings, transgenic mice expressing single human liver detoxification enzymes or transcription factors have allowed researchers to better understand human drugresponse pathways (See e.g., Xie and Evans (2002) Drug Discov. Today 7(9): p. 509-15.). Based on these promising findings, humanized mouse programs have been initiated within many pharmaceutical companies towards the development of tools for pre-clinical drug-testing, disease models (e.g., infectious disease models) and the development of novel therapies, diverse humanized mouse applications including drug testing, disease models and the development of novel therapies Despite these advances, the generation of humanized and chimeric mice is an inherently inefficient process with limited scalability and thus limited widespread utility. Currently, approaches for creating humanized mice require complex transgenics (to model single human genes) and/or cell transplantation protocols (to model whole human organ systems). In the case of the cell transplantation approach, manipulation of the host is often required to provide a sufficient repopulation advantage to transplanted cells. For example, injected hepatocytes home to, engraft and repopulate a mouse liver only in the setting of genetically-induced host liver injury (See e.g., Azuma et al. Nat. Biotechnol. 25(8): p. 903-10; and Tateno et al. (2004) Am. J. Pathol. 165(3): p. 901-12.). Even with this repopulation advantage, the time window required to permit cell engraftment and expansion is lengthy (several weeks to months) and the overall engraftment efficiency among injected animals low (16% injected animals). Thus, a new model which mitigates the need for repopulation stimuli—and which can be generated rapidly and reproducibly among diverse animal backgrounds—promises to significantly advance the commercial utility of humanized mouse models for studying human biology and human disease.

SUMMARY OF THE INVENTION

The present invention features tissue engineering approaches to establish humanized animal models of human tissue (e.g., liver, pancreas, neuronal tissue, muscle tissue, adipose tissue, and the like) with minimal time, cost and labor, compared to existing art. The invention features implantable scaffolds that are stabilized ex vivo using an engineered biomaterial (e.g., a biocompatible, polymeric hydrogel, tuned with key soluble and/or adhesion-promoting factors or other important biochemical cues and standard tissue culture techniques. Cells can be cultured for short periods (e.g., ~1 week) to sufficiently stabilize the desired morphology, phenotype and/or function, (or can be cultured in order to obtain the desired morphology, phenotype and/or function, for example, using progenitor or stem cells as a parenchymal cell source) and then inserted into an ectopic site in an animal (e.g., a mouse), for example, in the intraperitoneal space, subcutaneous space, in a tissue, in a body cavity, etc. The constructs of the invention are amenable to facile manipulation, implantation and integration, removal and assessment in a normal animal setting.

The invention features implantable scaffolds, e.g., natural or synthetic polymeric scaffolds, in which human parenchymal cells are encapsulated with one or more populations of non-parenchymal cells in an implantable construct. The constructs are implantable in any one of a host of laboratory animals, e.g., mice, at an ectopic site within the animal. The constructs are engineered such that the parenchymal cells maintain the differentiated morphology, phenotype and cellular function characteristic of the source tissue from which they were derived (e.g., maintain tissue specific function.) In exemplary embodiments, non-parenchymal cells are included in the engineered constructs to support the tissue specific function of the parenchymal cells and, optionally, to influence the surrounding vasculature to provide nutrients and/or oxygen to the implanted constructs. Thus, the constructs are capable of surviving and functioning in the host animal for significant periods of time making the animals implanted with such constructs ideal models for drug discovery and development. Certain non-parenchymal cells can support the differentiated phenotype and function of the co-encapsulated parenchymal cells by secreting supportive, differentiation-inducing factors or other stabilizing factors. Certain non-parenchymal cells support the parenchymal cells by influencing the environment of the co-encapsulated cells, for example, secreting cytokines and/or growth factors that influence vascularization of the constructs. Without being bound in theory, it is also contemplated that sufficiently highly functioning parenchymal cells can be encapsulated without nonparenchymal cells, for example, if stabilized or pre-stabilized with appropriate biochemical cues. Exemplary embodiments of the constructs of the invention are described in the appended claims. Certain of the generic constructs (e.g., encapsulating a variety of human-derived parenchymal cells) as claimed, can be further characterized in detailed terms as set forth infra and in the appended claims describing hepatic constructs of the invention. Detailed description infra describing methods of making, and in certain instances, methods of using hepatic constructs, can also be applied to generic constructs as claimed herein.

In exemplary aspects, the invention features a highly tunable implantable scaffold to stabilize the phenotype of human hepatocytes, which mitigates the need for complicated mouse genetics, or a lengthy engraftment and repopulation time period (~6 weeks) in vivo associated with art-recognized humanized mouse approaches for studying liver biology and disease. The human hepatocytes are not required to repopulate the mouse liver in order to rescue the mouse from liver failure; therefore, systemic, in vivo studies can be performed readily, and species-specificity confirmed on a per construct basis (i.e., upon explanting liver tissues).

Tissue engineering techniques combining scaffolds and cells have been previously used to deliver hepatocytes in vivo; however, prior work has focused on the long-term treatment of liver disease and has been challenged by the high metabolic needs of primary hepatocytes. In particular, previous work using biodegradable polymer scaffolds for hepatocyte delivery has focused on acellular scaffolds, which have proven to be limited in assuring homogenous seeding, achieving high engraftment efficiency and maintaining the hepatocyte phenotype (See e.g., Kaufmann et al. (1997) Cell Transplant 6(5): p. 463-8; and Kneser et al. (1999) J. Biomed. Mater. Res. 47(4): p. 494-503.). Indeed, hepatocytes transplanted into rats on such biodegradable polymer matrices were found to be inferior to liver grafts of equivalent liver mass in compensating for metabolic deficiencies (See e.g., Uyama et al. (2001) Transplantation 71(9): p. 1226-31.) Tissue engineers have also struggled with challenges in vascularizing and oxygenating transplanted hepatic tissues. Experienced researchers may rely on surgical techniques, namely a combination of portacaval shunt surgery and partial hepatectomy, to supply implanted tissues with portal-supplied nutrients (see e.g., Kaufmann et al. (1994) J. Transplant Proc. 26(6) 3343-5; Starzl et al. (1975) J. Surg. Gynocol. Obstet. 141(6), 843-58; and Smith et al. (2006) J. Tissue Engin., vol 12 235-244. Recently, pre-vascularization of therapeutic hepatocyte transplantation sites has been pursued to facilitate transplant integration (See e.g., Levenberg et al. (2005) Nat. Biotechnol. 23(7): p. 879-84; Ohashi et al. (2005) Hepatology 41(1): p. 132-40; Stevens et al. (2005) Proc. Natl. Acad. Sci. USA. 102(32): p. 11450-5; and Yokoyama et al. (2006) Am. J. Transplant. 6(1): p. 50-9.). Despite moderate success using these strategies for therapeutic liver tissue engineering applications, these protocols add additional surgical steps and add technical complexity, as well as time (weeks) to the generation of liver model mice.

Unlike existing tissue engineered platforms, this invention uses an encapsulating hydrogel which is optimized to support hepatic functions of a homogenously distributed cell-matrix suspension, and which can be implanted directly in vivo for efficient integration and rapid probing of human liver responses. Using non-invasive imaging technologies, it has been shown that engineered tissues survive in vivo for up to several weeks, a sufficient period of time to dose animals and assess human cytochrome P450-mediated drug-drug interactions and drug-induced human liver toxicity (See e.g., Brandon et al. (2003) Toxicol Appl Pharmacol 189(3): p. 233-46; and Wienkers and Heath (2005) Nat. Rev. Drug. Discov. 4(10): p. 825-33.). It has further been shown that engineered tissues can be infected in vitro or in vivo with virus (e.g., HCV) and that viral infection can persist for up to several weeks. This model therefore allows non-expert researchers to effectively evaluate human liver responses to pharmacologic drugs (e.g., in toxicology testing and/or therapeutic testing) in vivo. In certain embodiments, the engineered liver tissue constructs include hepatocytes encapsulated an appropriate density or concentration such that cells have sufficient oxygen and/or nutrients to survive for a period of time preceding vascularization of the tissue. The skilled artisan will appreciate the highly metabolic nature of hepatocytes and recognize the benefits of the systems of the invention in promoting survival and/or preventing necrosis of the parenchymal cells of the constructs.

The human liver model of the invention results in long term survival of human liver tissues for the study of viral life cycles, liver pathologies, and the development of new treatments (e.g., anti-viral treatments, etc.) Furthermore, the engineered tissue model has the potential to provide several unique advantages not feasible using cell transplantation techniques alone. Engineered human tissues may be used to generate human liver models in immune-competent hosts, as well as immune-compromised hosts. The humanized mice generated by the methods of the invention are also conducive to multiplexing, whereby hepatocytes from different liver donors may be simultaneously implanted and compared in the same host animal. Only in an engineered human liver mouse model can both the liver tissue and host background be so readily exchanged, tested and compared. Without requiring researchers to perform complex mouse genetics or to wait months for human hepatocytes to repopulate a damaged liver, this invention allows academic and commercial scientists to more efficiently study human-specific liver pathologies, infectious diseases, treatment therapies, dosing regimes, drug-drug interactions, and toxicity.

In exemplary aspects, the invention describes a novel humanized liver mouse model, referred to also as humanized mice with ectopic artificial liver tissue (HEAL), in which engineered human liver constructs are implanted in vivo for rapid utility in drug development and the study of human liver responses to drugs, toxins, or pathogens.

µm thick), implanted in the intraperitoneal cavity of a nude mouse and extracted on day 7 of implantation. The mimetic is shown fully extracted into a 12-well tissue culture plate for macroscopic vessel visualization.

Figure 1D:
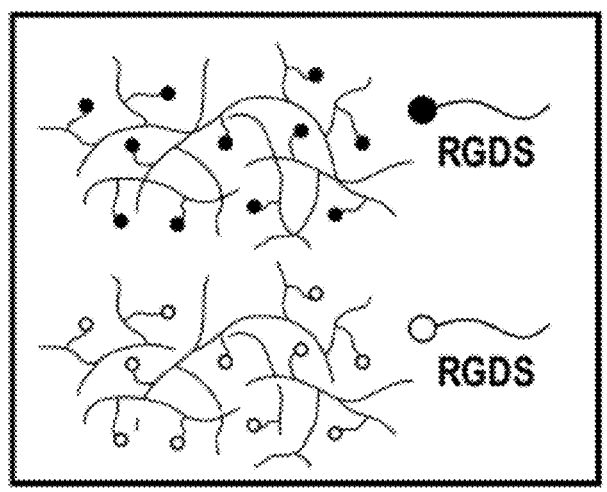
FIG. 1a: Depicts implantable human liver mimetics engineered for hepatic functions ex vivo. The schematic depicts the fabrication, implantation and utility of human liver mimetics for generating humanized mice for drug development. Primary hepatocytes are co-cultivated with stabilizing stromal fibroblasts on collagen-coated plates for 7-10 days, then photo-encapsulated with additional liver non-parenchymal cells in polyethylene glycol-diacryate (PEG-DA; 20 kDa, 10% w/v) scaffolds derivitized with adhesion peptides. The resulting human liver mimetic, approximately 20-mm diameter and 250 μm thick and comprising ~$0.5 \times 10^6$ human hepatocytes, is implanted in a laboratory mouse, where engrafted and vascularized mimetics establish humanized models for drug development applications.
FIG. 1b: depicts photographic images of human liver mimetics. A human liver mimetic comprising human hepatocytes, fibroblasts and liver endothelial cells (LEC) encapsulated in PEGDA+RGDS hydrogel (10-mm diameter, 250-μm thick), implanted in the intraperitoneal cavity of a nude mouse and extracted on day 7 of implantation. The mimetic is shown attached to the mouse mesentery tissue and partially extracted with forceps.
FIG. 1c: depicts photographic images of human liver mimetics. A human liver mimetic comprising human hepatocytes, fibroblasts and liver endothelial cells (LEC) encapsulated in PEGDA+RGDS hydrogel (10-mm diameter, 250-

FIG. 1d: depicts the covalent modification of PEG-DA hydrogels with the ligand RGDS peptide or RGES negative control (10 µmol/ml).

Figure 1E:
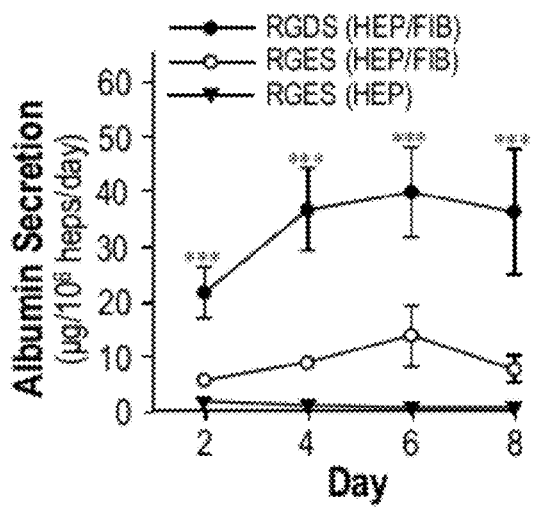

FIG. 1e: graphically depicts the assessment of encapsulated primary hepatocytes (HEP) versus hepatocyte/stromal fibroblast co-cultures (HEP/FIB) for the hepatic function of albumin secretion over time.

Figure 1F:
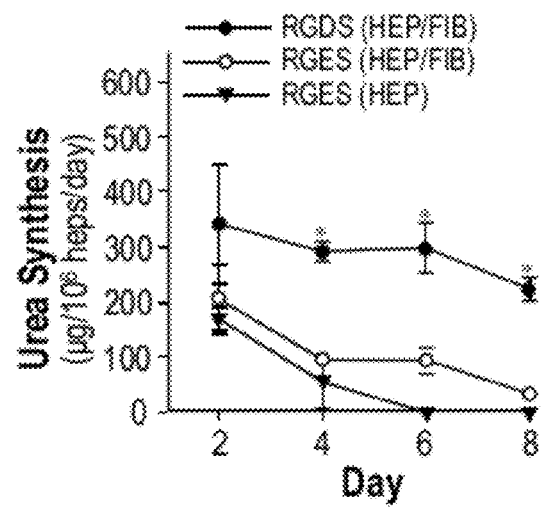

FIG. 1f: graphically depicts the assessment of encapsulated primary hepatocytes (HEP) versus hepatocyte/stromal fibroblast co-cultures (HEP/FIB) for the hepatic function of urea synthesis over time (10 µmol/ml).

Figure 1G:
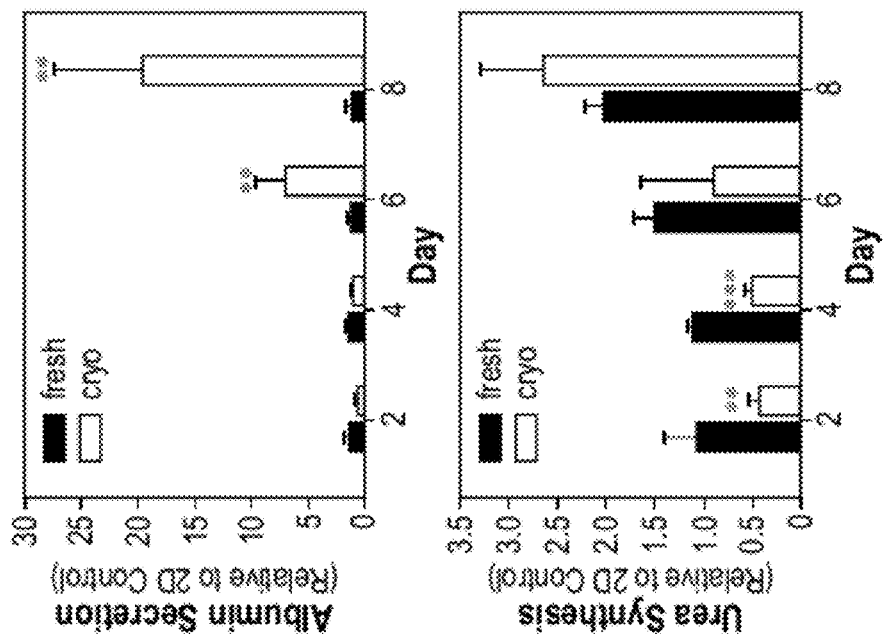

FIG. 1g: graphically depicts the functional assessment and viability of human liver mimetics fabricated from fresh versus cyropreserved primary human hepatocytes. Fresh or cryopreserved primary human hepatocytes were co-cultivated with stromal fibroblasts on collagen plates for 7-10 d, then encapsulated in PEG-DA hydrogels (10% w/v, 20 kDa) derivitized with RGDS (10 µmol/ml). Hepatic functions albumin secretion and urea synthesis were measured over time from spent media from fresh (black bars) or cryopreserved (white bars) hepatic mimetics. Functions are reported relative to monolayer hepatocyte/fibroblast co-cultures on collagen.

Figure 1H:
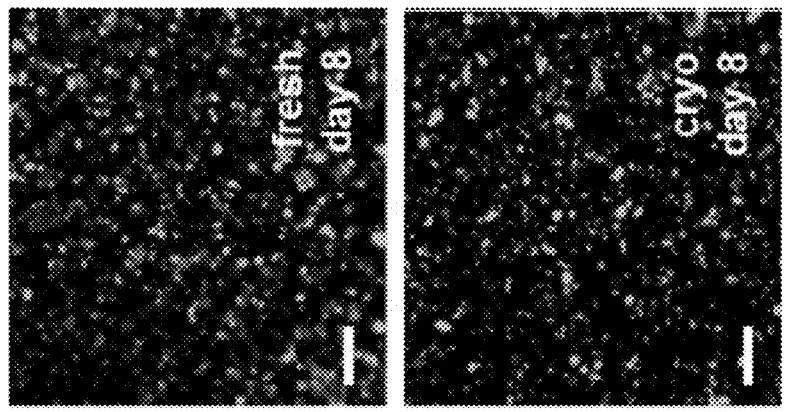

FIG. 1h: depicts fluorescence micrographs of fresh (top) versus cryopreserved (bottom) human liver mimetics treated with the green/red calcein AM/ethidium homodimer viability/death stain, 8 days after encapsualtion. Scale bars 200 µm. p<0.01, *p<0.001 for n=6 and SEM.

Figure 1I:
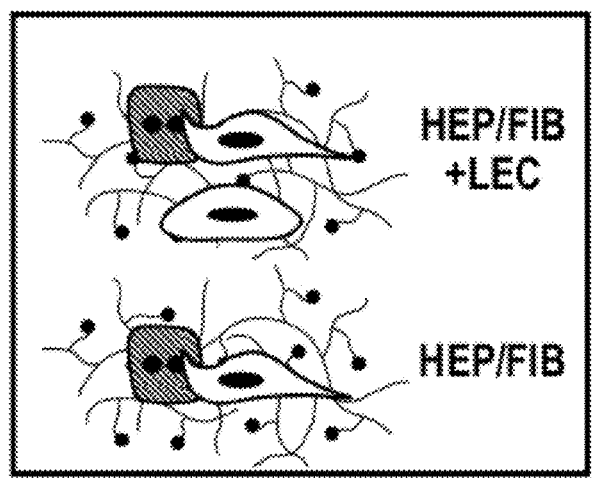

FIG. 1i: depicts the co-encapsulation of human liver endothelial cells (LEC) with HEP/FIB co-cultures within RGDS-derivitized PEG-DA hydrogels.

Figure 1J:
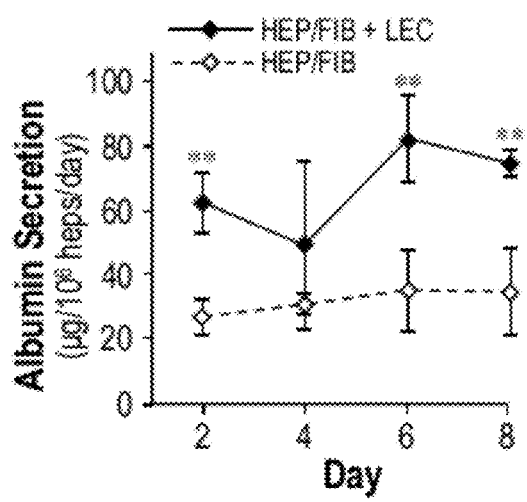

FIG. 1j: graphically depicts the assessment of albumin secretion over time from the co-encapsulated human liver endothelial cells (LEC) with HEP/FIB co-cultures within RGDS-derivitized PEG-DA hydrogels. *p<0.01, p<0.05, *p<0.001 for n=6 and SEM.

Figure 1K:
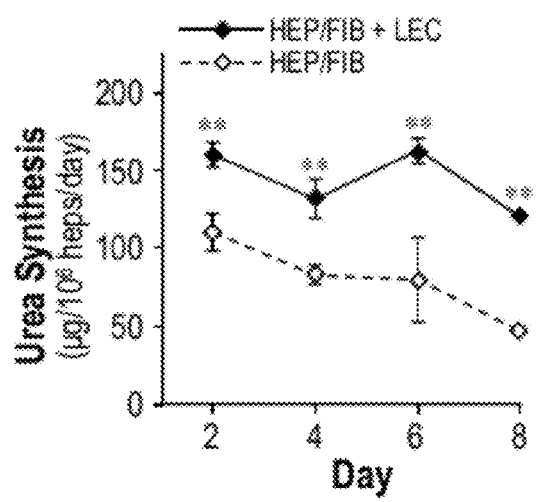

FIG. 1k: graphically depicts the assessment of urea synthesis over time by the co-encapsulated human liver endothelial cells (LEC) with HEP/FIB co-cultures within RGDS-derivitized PEG-DA hydrogels. *p<0.01, p<0.05, *p<0.001 for n=6 and SEM.

Figure 1L:
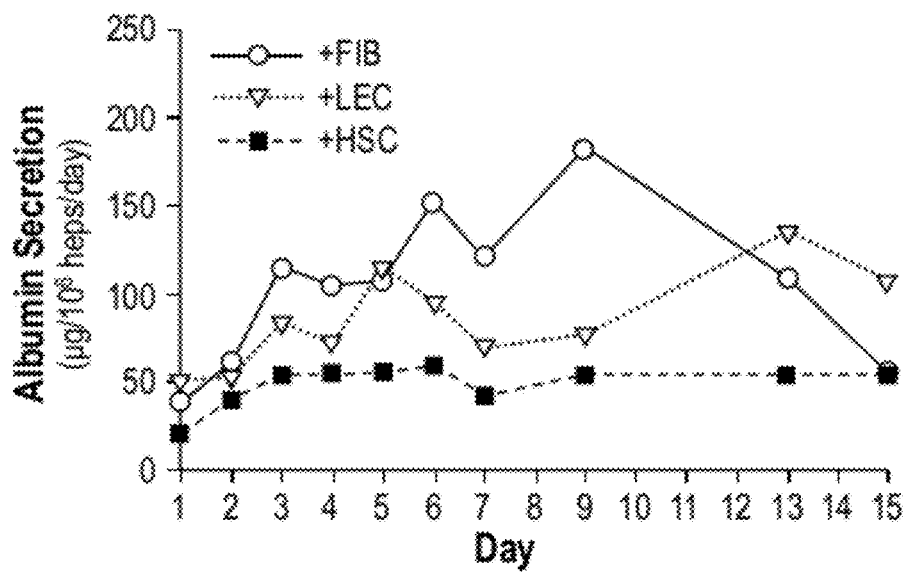

FIG. 1l: graphically depicts the functional optimization of rat liver HEP/FIB mimetics by co-encapsulation of additional fibroblasts (FIB), liver endothelial cell line (LEC), or hepatic stellate cell line (HSC) cells. HEP/FIB co-cultures ($8\times10^6$ hep/ml) were mixed with FIB, LEC, and HSC ($6\times10^6$ cells/ml), photo-encapsulated in PEG+RGDS hydrogels, and monitored for albumin secretion over 15 days.

Figure 1M:
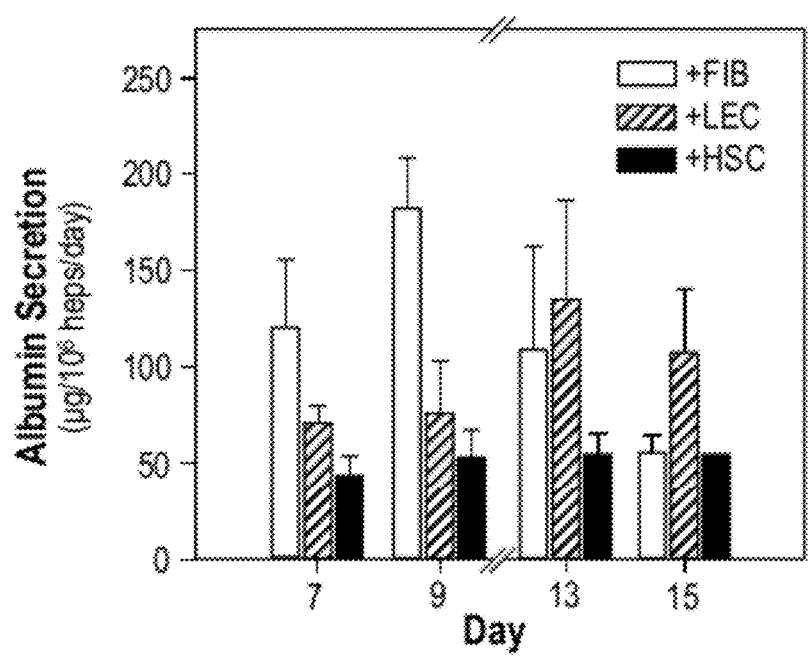

FIG. 1m: depicts the bar graph analysis of albumin secretion on days 7, 9, 13 and 15 post-encapsulation. n=3 per condition, with error bars representing SEM.

Figure 1N:
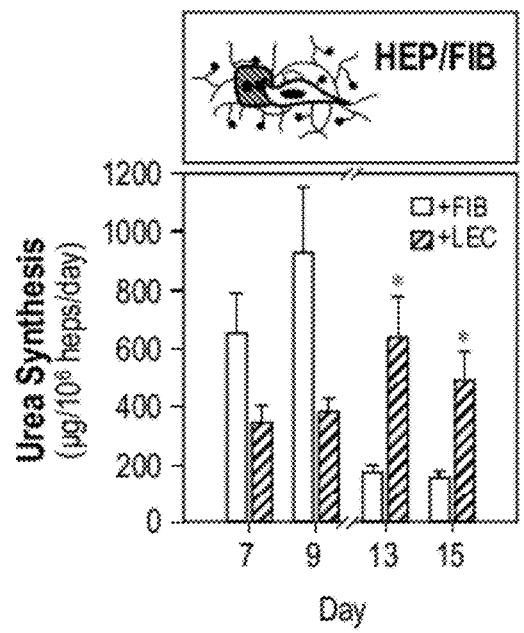

FIG. 1n: graphically depicts urea synthesis of liver mimetics made by co-encapsulating primary rat HEP/FIB co-cultures with additional liver endothelial cells (+LEC) or fibroblasts (+FIB), at ~1 or 2-weeks of culture. This demonstrates that the stabilizing effect of co-encapsulated liver endothelial cells (LEC) is dependent on HEP/FIB contact and may be via secretion of short-range soluble factors.

Figure 1O:
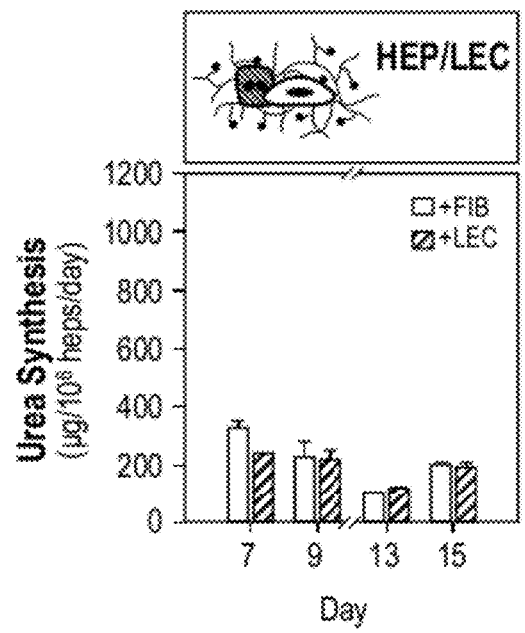

FIG. 1o: graphically depicts urea synthesis of mimetics made by co-encapsulating primary rat HEP/LEC co-cultures with additional +LEC or +FIB, at ~1 or 2-weeks of culture. This demonstrates that the stabilizing effect of co-encapsulated liver endothelial cells (LEC) is dependent on HEP/FIB contact and may be via secretion of short-range soluble factors.

Figure 1P:
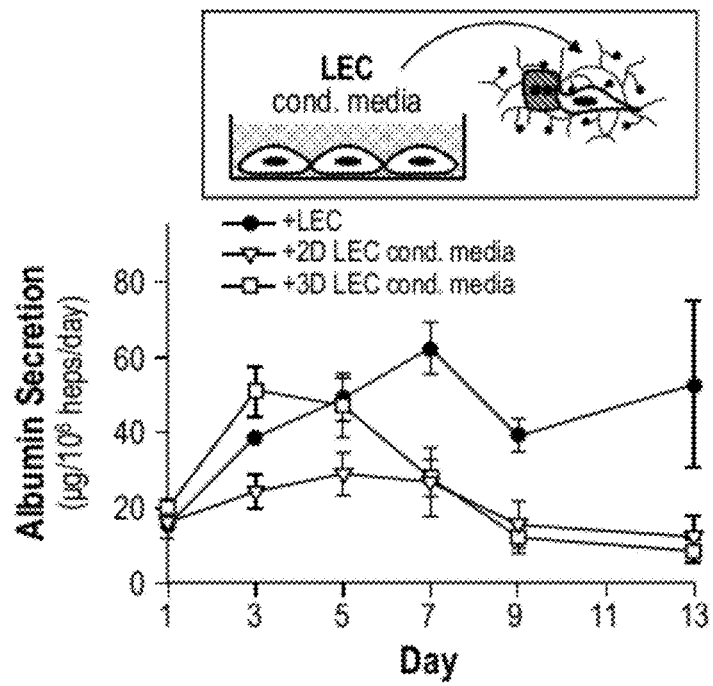

FIG. 1p: graphically depicts albumin secretion of rat HEP/FIB liver mimetics is not rescued by 2D or 3D LEC conditioned media. *p<0.05, p<0.01 *p<0.001 compared to control for n=4 and SEM. This demonstrates that the stabilizing effect of co-encapsulated liver endothelial cells (LEC) is dependent on HEP/FIB contact and may be via secretion of short-range soluble factors.

Figure 2A:
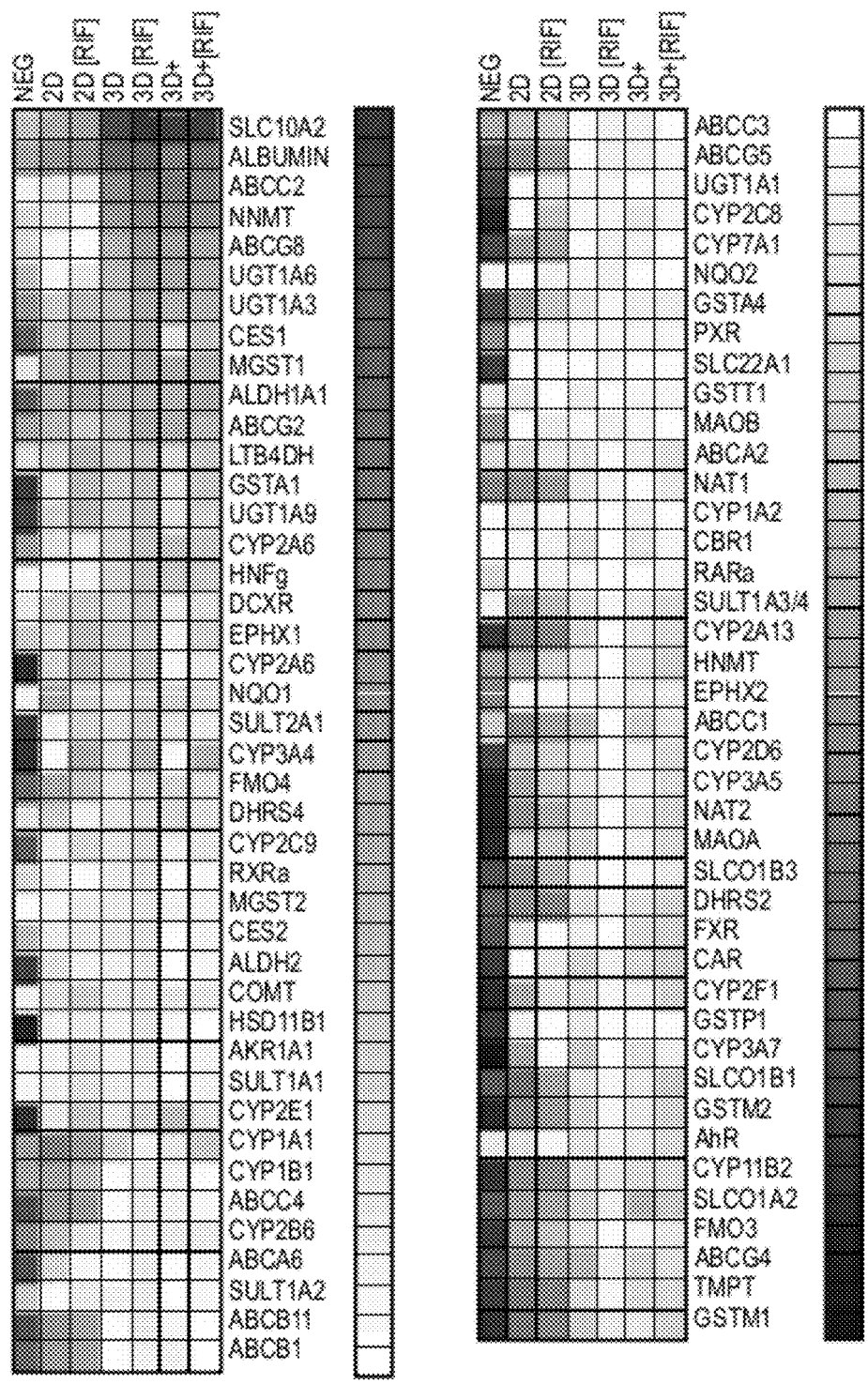

FIG. 2a: depicts the characterization of human liver mimetics for drug metabolism gene expression and functions, and graphically depicts the heat map display of Luminex multiplex PCR analysis for 83 human-specific drug metabolism genes and transcription factors. Columns are representative analyses of RNA extracted from 2D HEP/FIB cultures, 3D HEP/FIB mimetics and 3D HEP/FIB+LEC mimetics on day 10 post-encapsulation, for triplicate samples in two independent experiments. "Neg" are non-hepatic HeLa cell controls. Prior to RNA extraction, samples were either exposed to CYP450 inducer rifampin (25 µM daily for 3 days, labeled "[RIF]") or DMSO control.

Figure 2B:
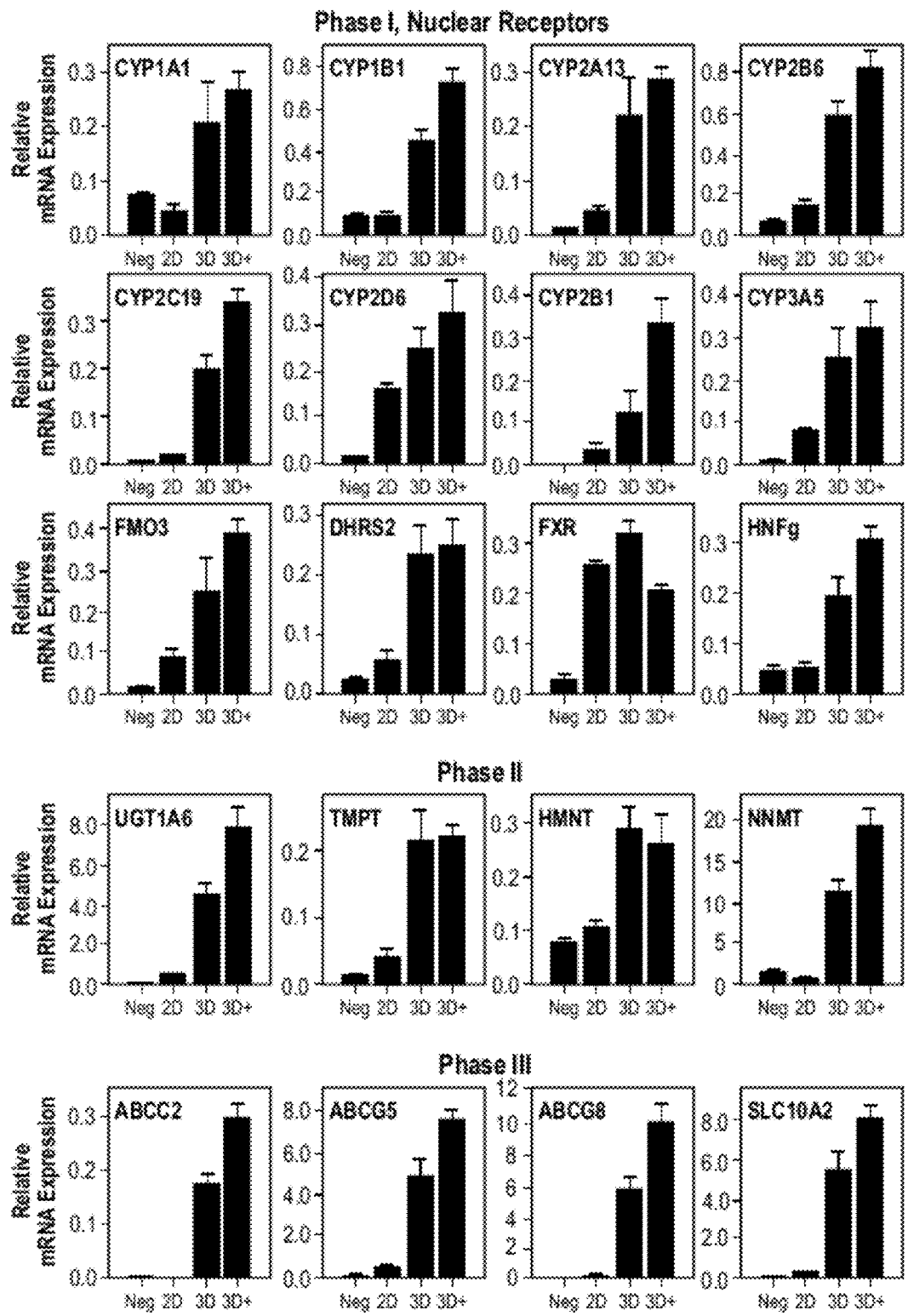

FIG. 2b: graphically depicts select gene sets comparing the relative mRNA expression of HeLa (Neg), 2D HEP/FIB (2D), 3D HEP/FIB (3D) or 3D HEP/FIB+LEC (3D+) for Phase I, nuclear receptors, Phase II and Phase III drug metabolism genes after DMSO exposure.

Figure 2C:
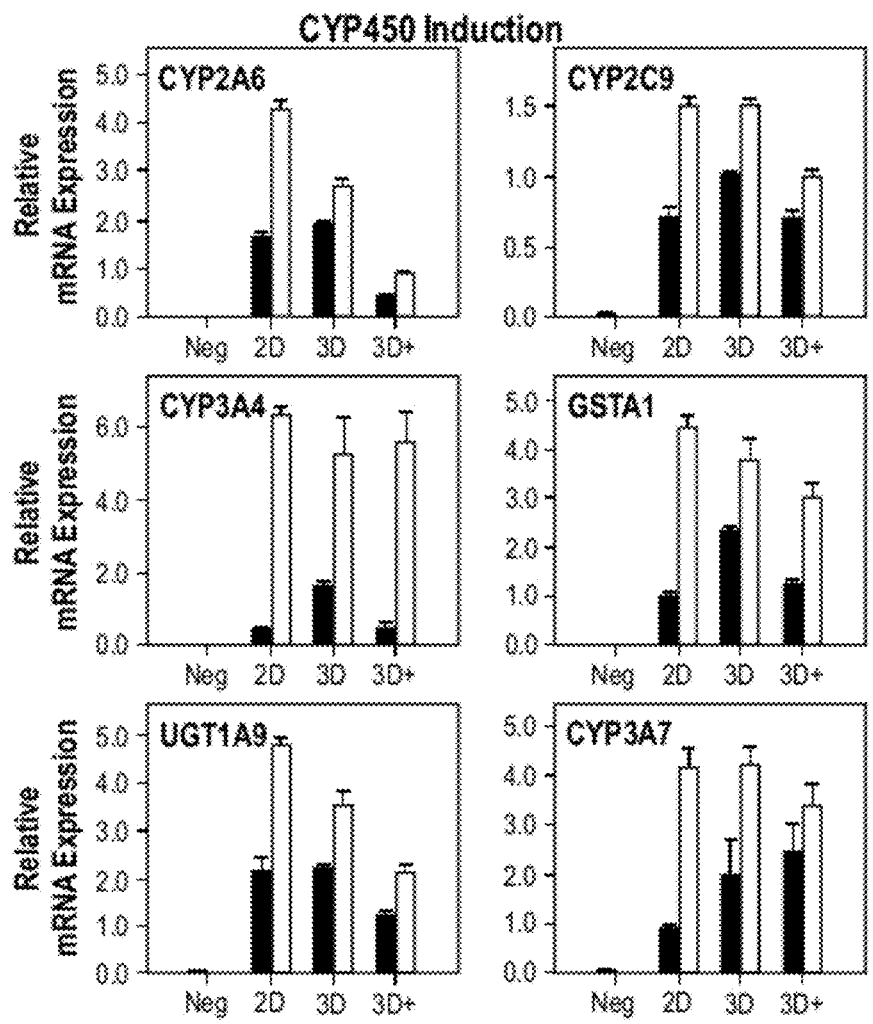

FIG. 2c: graphically depicts select gene sets comparing the relative mRNA expression of HeLa (Neg), 2D HEP/FIB (2D), 3D HEP/FIB (3D) or 3D HEP/FIB+LEC (3D+) for Phase I, nuclear receptors, Phase II and Phase III drug metabolism genes after DMSO exposure and compared to RIF exposure. Black bars represent DMSO-treated samples and white bars represent RIF-treated samples. mRNA expression is shown relative to average of control gene transferin.

Figure 2D:
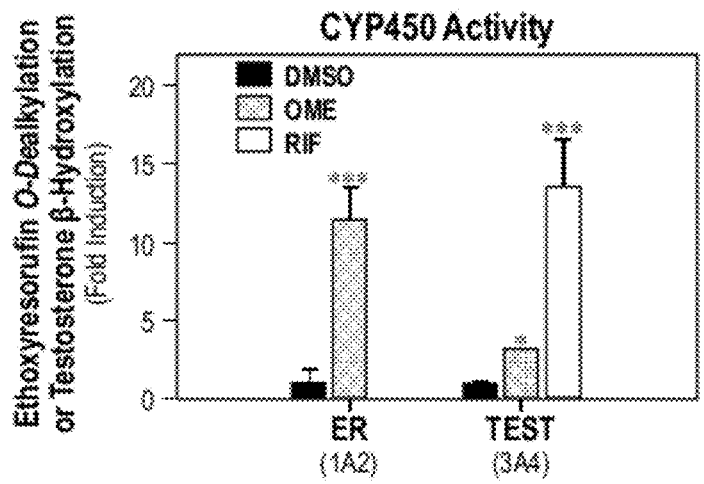

FIG. 2d: graphically depicts CYP450 activity, induction and drug interactions in day 6 human liver mimetics treated with clinical inducers omeprazole (OME, 40 µM) or rifampin (RIF, 25 µM) in vitro. Cultures were treated daily with inducers for 3 d before incubation with ethoxyresorufin (ER) or testosterone (TEST), conventional substrates for CYP1A2 and CYP3A4 respectively. Fold-induction of CYP450 activity was determined by normalization to DMSO control. By Student's T test, *p<0.01, ***p<0.001 for n=4 and SD.

Figure 2E:
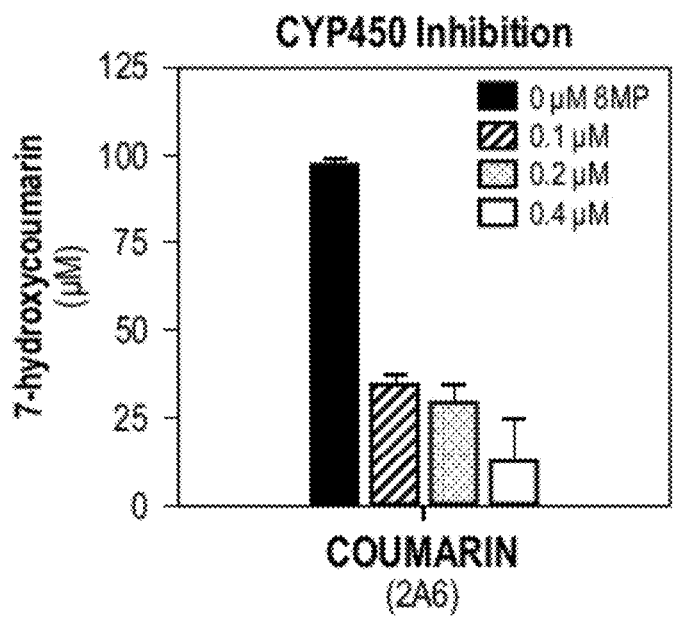

FIG. 2e: depicts the characterization of CYP450 inhibition in human liver mimetics. Human liver mimetics treated with the clinical CYP2A6 inhibitor 8-methoxypsoralen (8 MP) at 0, 0.1, 0.2, or 0.4 µM for 1 h before incubation with CYP2A6 substrate coumarin (100 uM for 2 h). 7-hydroxylation of coumarin to 7-hydroxycoumarin was measured by LC/MS/MS against a standard curve. *p<0.05 for n=2 and SEM.

Figure 2F:
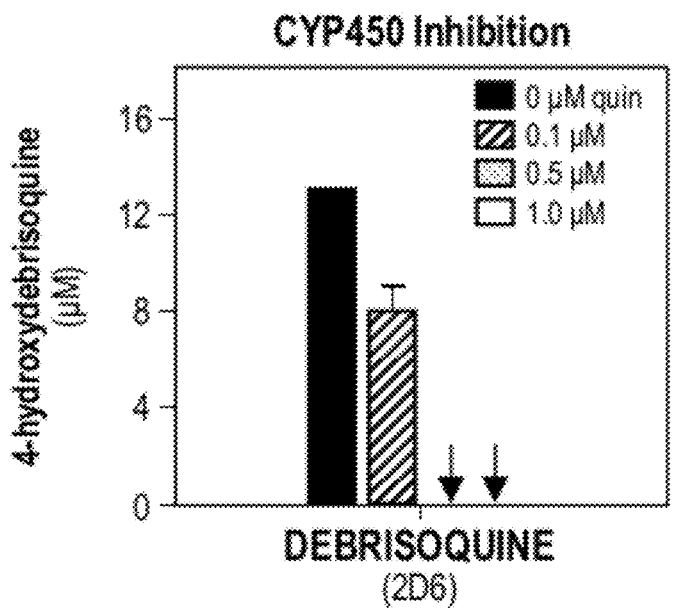

FIG. 2f: depicts the characterization of CYP450 inhibition in human liver mimetics. Human liver mimetics treated with the clinical CYP2D6 inhibitor quinidine (quin) at 0, 0.1, 0.5, or 1.0 µM for 1 h before incubation with CYP2D6 substrate debrisoquine (100 uM for 2 h). 4-hydroxylation of debrisoquine to 4-hydroxydebrisoquine was measured by LC/MS/MS against a standard curve. Arrows represent values that were below the LC/MS/MS limit of detection. *p<0.05 for n=2 and SEM.

Figure 2G:
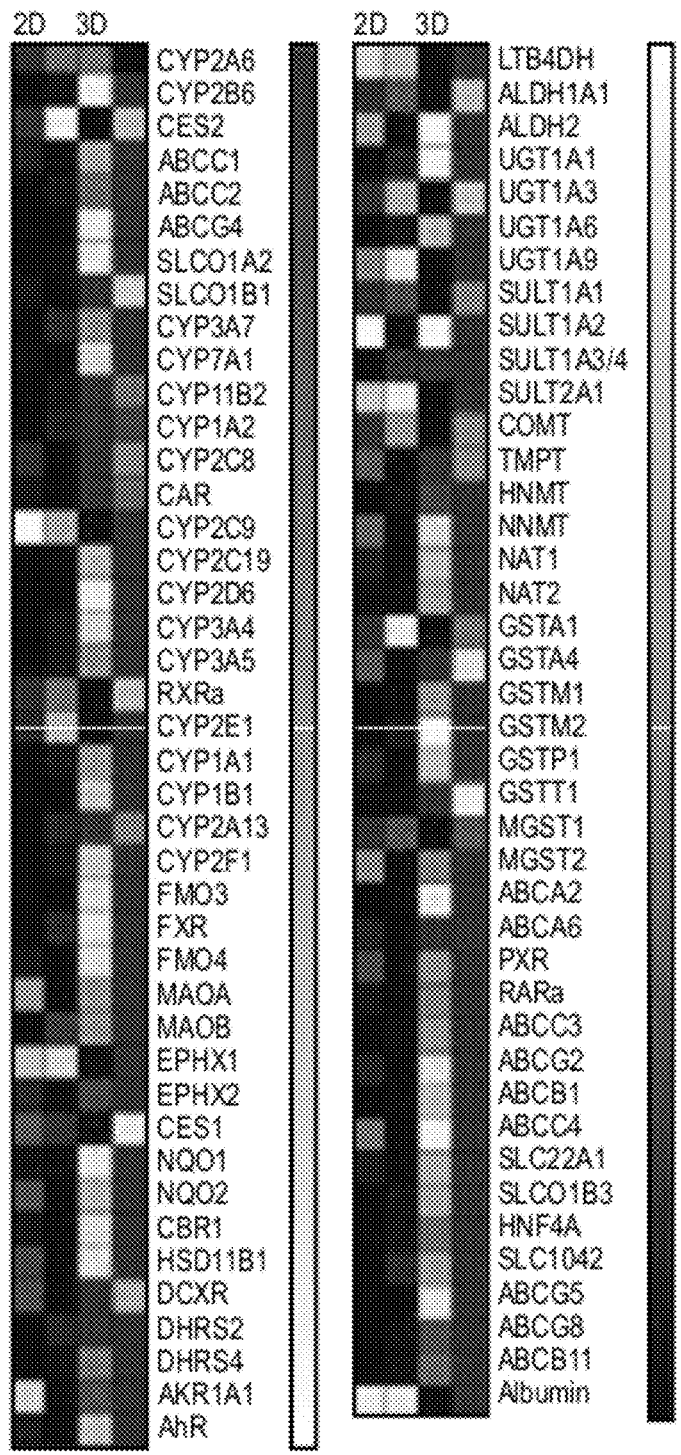
Figure 2G:
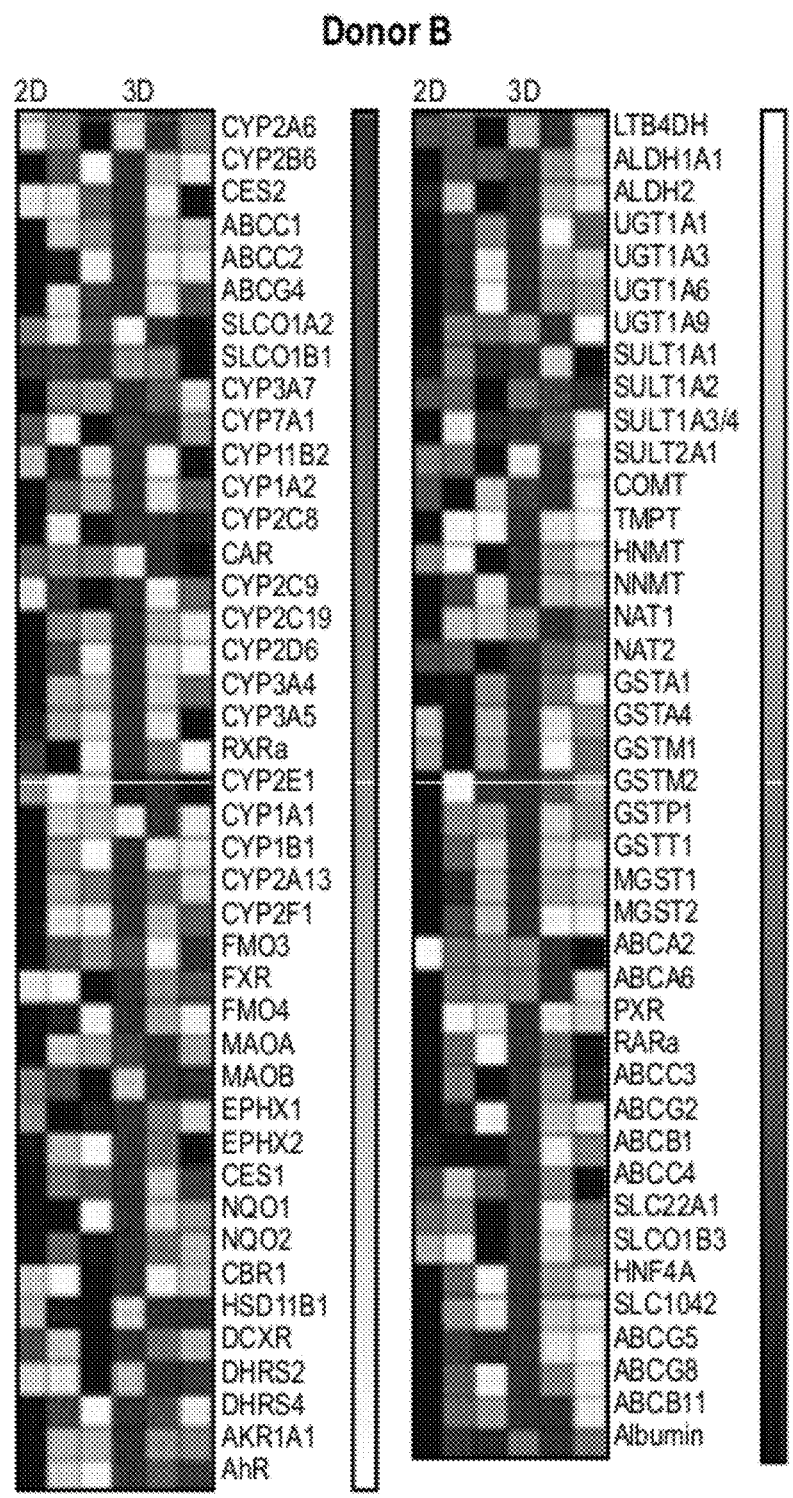

FIG. 2g: depicts characterization of HEALs for drug metabolism gene expression. Heat map displays of LMA-Luminex analysis for 83 human-specific drug metabolism genes and transcription factors, shown separately for independent experiments analyzing different hepatocyte donors (donor A or B). Columns represent replicate loadings of RNA extracted from 2D HEP/FIB cultures ("2D") or 3D HEP/FIB HEALs ("3D") on day 10 postencapsulation. mRNA expression is determined relative to average of control gene transferrin, and heat maps are row-normalized to distinguish relative 2D to 3D differences.

Figure 2H:
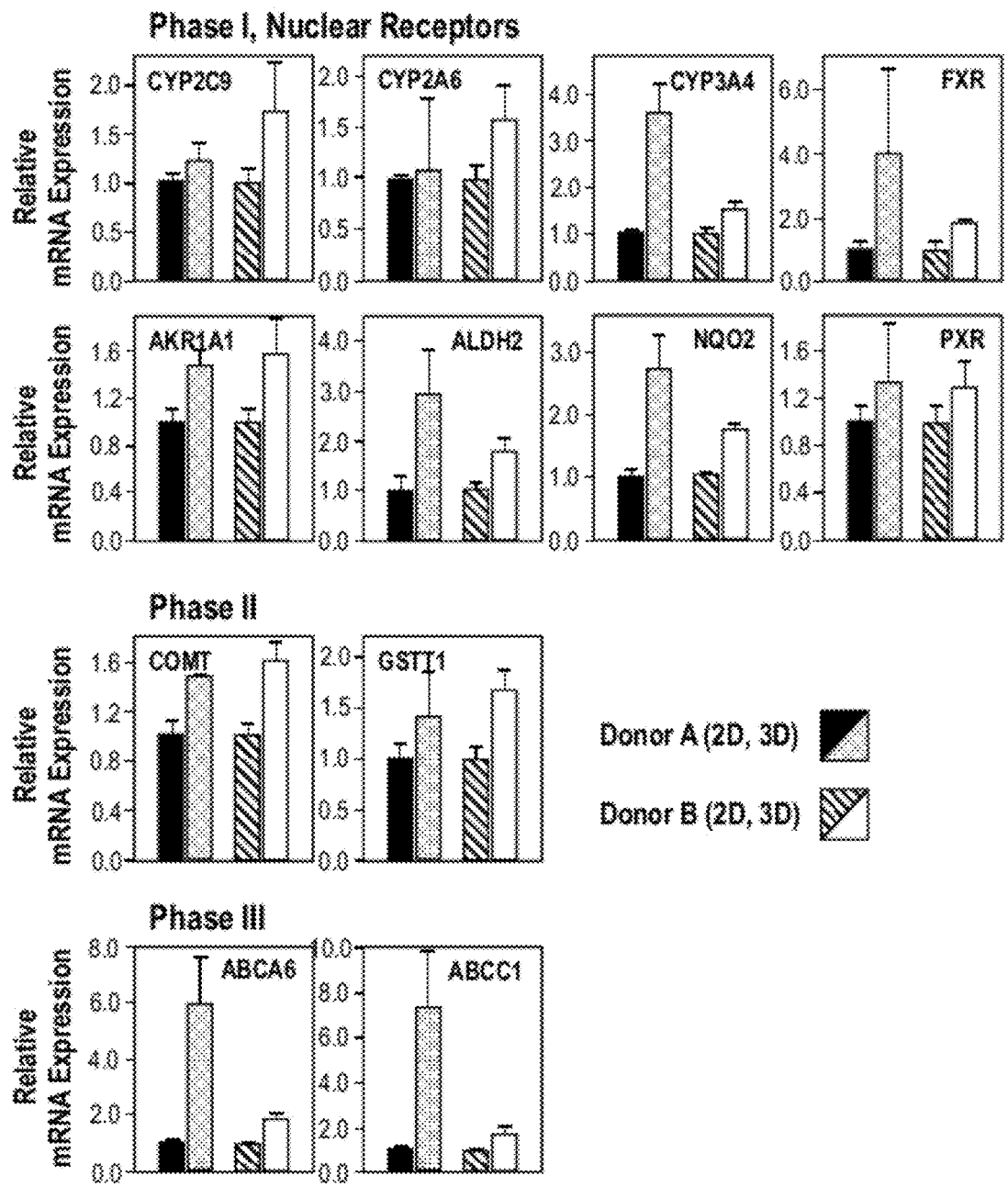

FIG. 2h: Select gene sets comparing the relative mRNA expression of 3D HEP/FIB HEALs (open bars), normalized to 2D HEP/FIB cultures (filled bars) for phase I, nuclear receptors, phase II, and phase III drug metabolism genes after DMSO exposure. Data represent the mean and SEM of Luminex-loaded replicates for donor A (black) and donor B (gray).

Figure 2I:
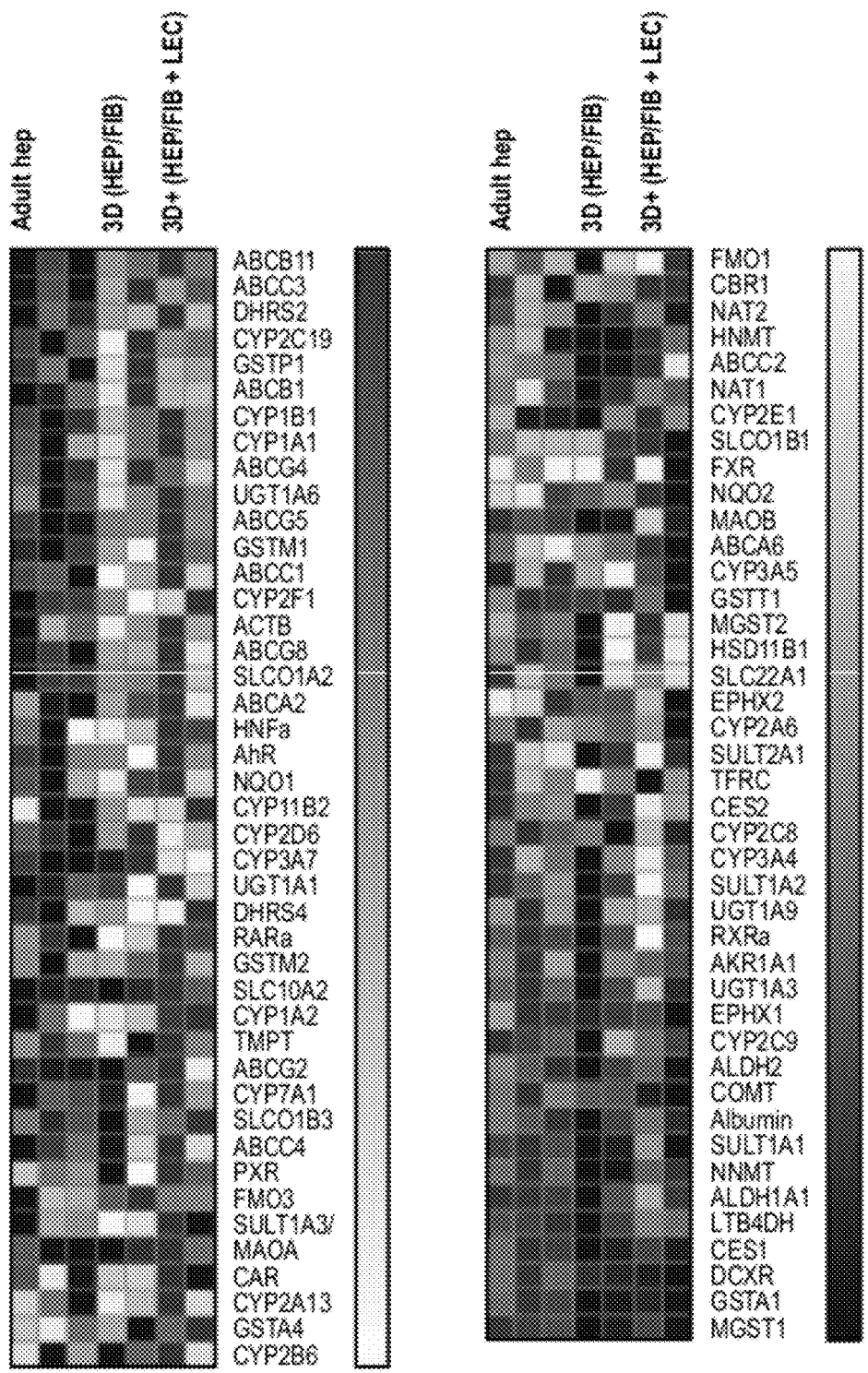

FIG. 2i: depicts comparative gene expression levels of 83 human-specific DME genes in adult liver samples ('Adult hep'), 3D HEP/FIB HEALs ('3D') and 3D HEP/FIB+LEC HEALS ('3D+') assessed in a single Luminex multiplex PCR assay and represented in heatmap display.

Figure 2J:
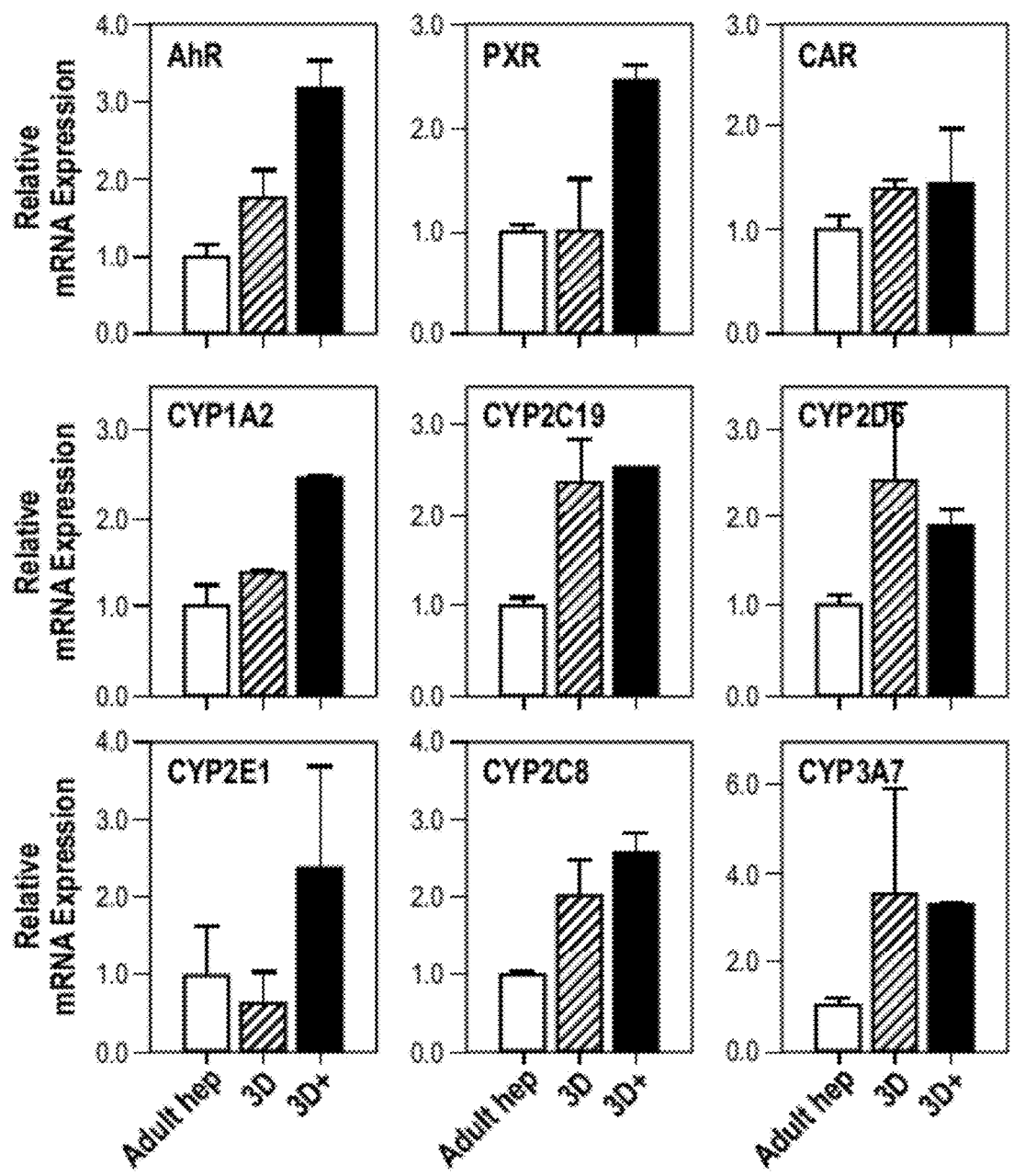

FIG. 2j: depicts expression of the CYP450 genes and their regulators, nuclear receptors AhR, PXR, and CAR and the CYPs responsible for metabolizing most clinical drugs in 3D and 3D+ HEALs (black bars) relative to the adult liver control (gray bars).

Figure 3A:
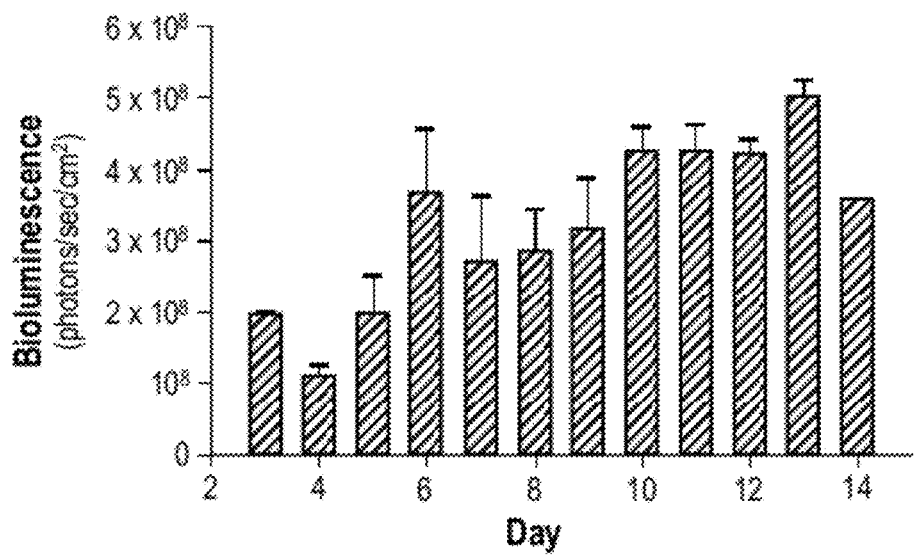

FIG. 3a: graphically depicts stable bioluminescence detection of firefly luciferase reporter-human liver mimetics in vitro. Hepatocyte/fibroblast cells co-cultivated for 7-10 days were transduced with lentivirus expressing firefly luciferase under the albumin promoter, and reporter liver mimetics made the following day by encapsulating transduced co-cultures in PEG-DA+RGDS hydrogels. Reporter liver mimetics were incubated briefly in 3 mg/ml luciferin/ PBS, and bioluminescence imaging was performed using the Xenogen IVIS with Living Systems software to collect peak luminescence flux over two weeks in vitro. Error bars represent SEM for n=3.

Figure 3B:
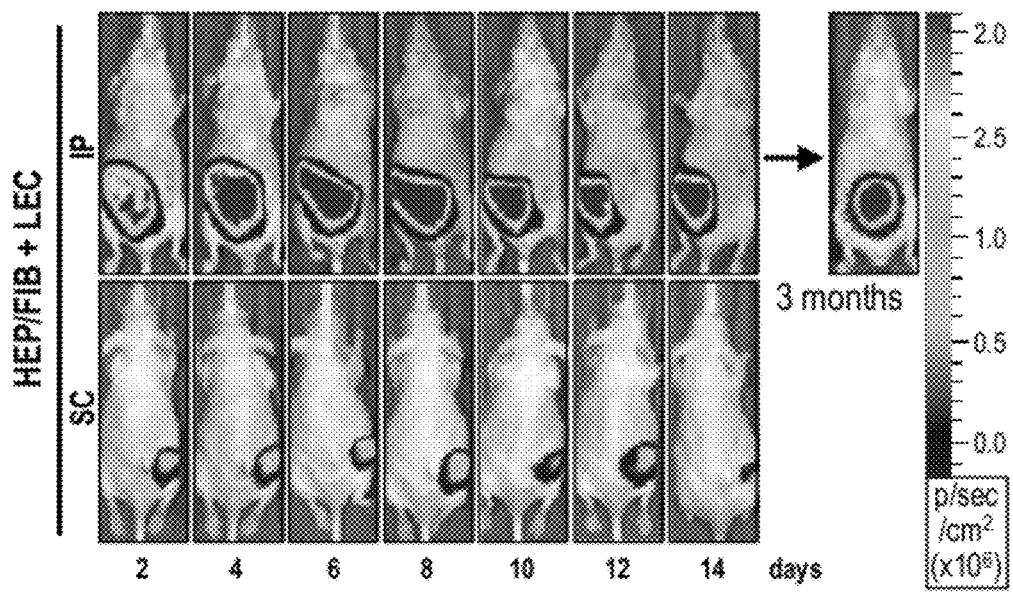

FIG. 3b: depicts in vivo bioluminescence imaging of humanized mice. Human liver mimetics were implanted at ectopic sites in the mice. HEP/FIB+LEC mimetics were fabricated using HEP/FIB co-cultures transduced by lentivirus to express luciferase under the human albumin promoter, prior to encapsulation.

Figure 3C:
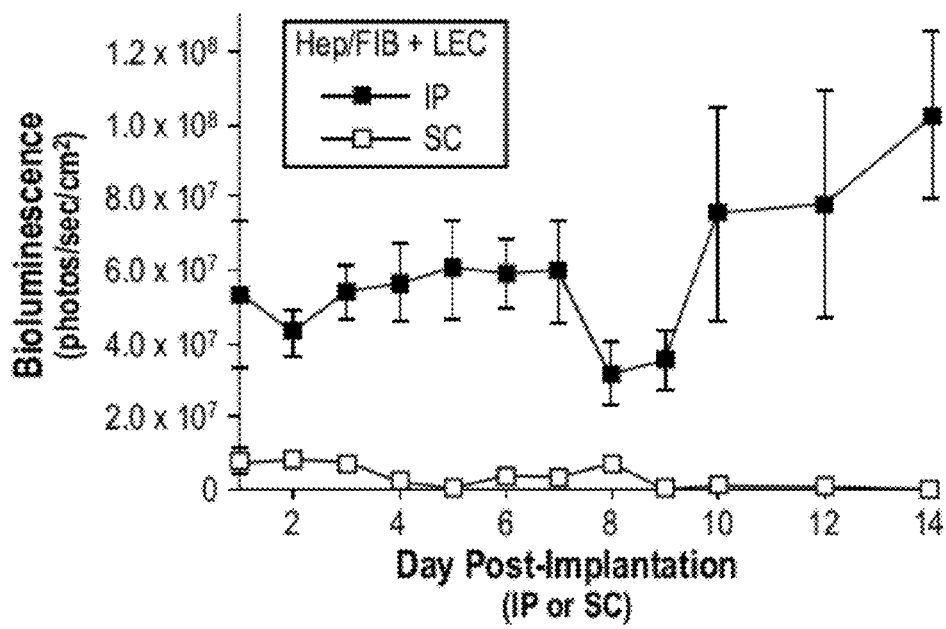

FIG. 3c: graphically depicts the quantitation of human liver mimetics implanted in the intraperitoneal cavity (IP) or subcutaneous space (SC) of athymic nude mice (n=8 for IP, n=3 for SC implants). HEP/FIB+LEC mimetics were fabricated using HEP/FIB co-cultures transduced by lentivirus to express luciferase under the human albumin promoter, prior to encapsulation.

Figure 3D:
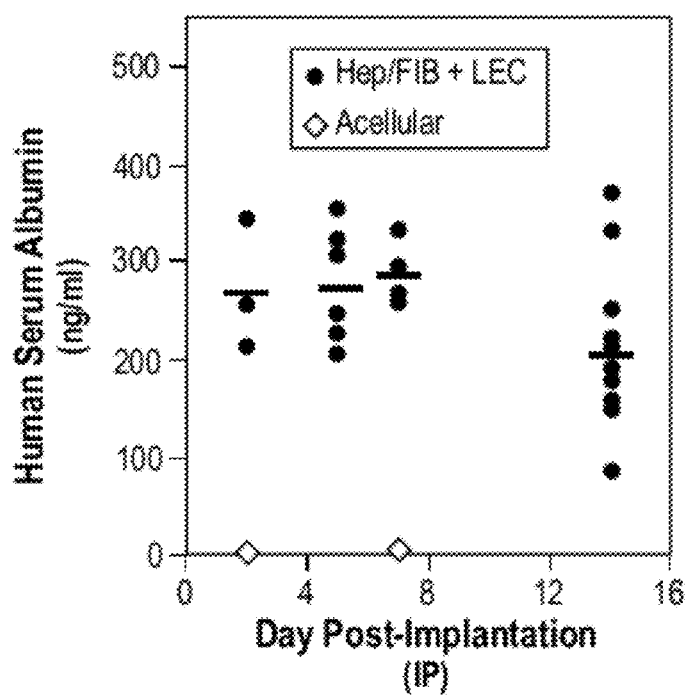

FIG. 3d: graphically depicts human serum albumin detected in mice humanized with IP liver mimetics. Red bars mark average human serum albumin levels at each timepoint for n=6 to 8 mice.

Figure 3E:
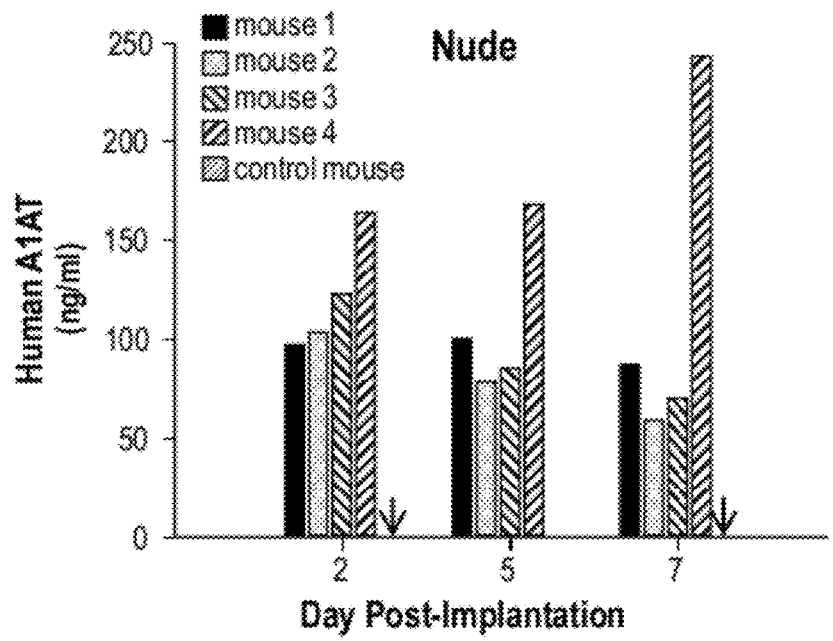
Figure 3F:
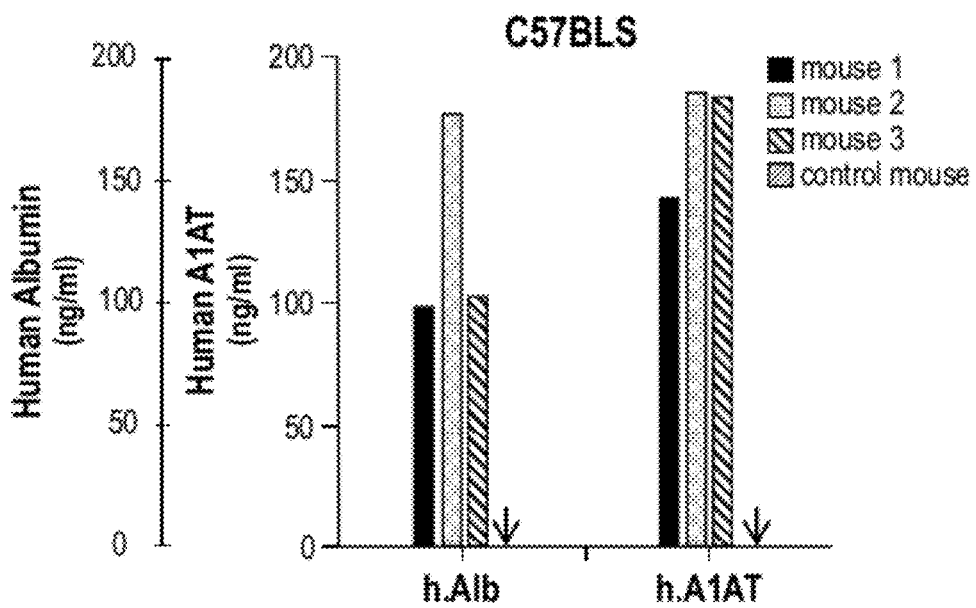

FIG. 3e: graphically depicts detection of human alpha-1-antityrpsin (A1AT) in serum of mice humanized with HEALs over time. Serum samples acquired on day 2, 5, and 7 after implantation in athymic nude mice were assayed for human A1AT by enzyme-linked immunosorbent assay. Plotted are n=4 mice per group, represented by individual bars (mouse 1, 2, 3, 4). Control mouse contains no implant; red arrows indicate that human A1AT was undetectable in these samples. FIG. 3f: depicts A1AT levels in similarly treated C57BL6 mice (immunocompetent mice) shown on day 2 post implantation.

Figure 3G:
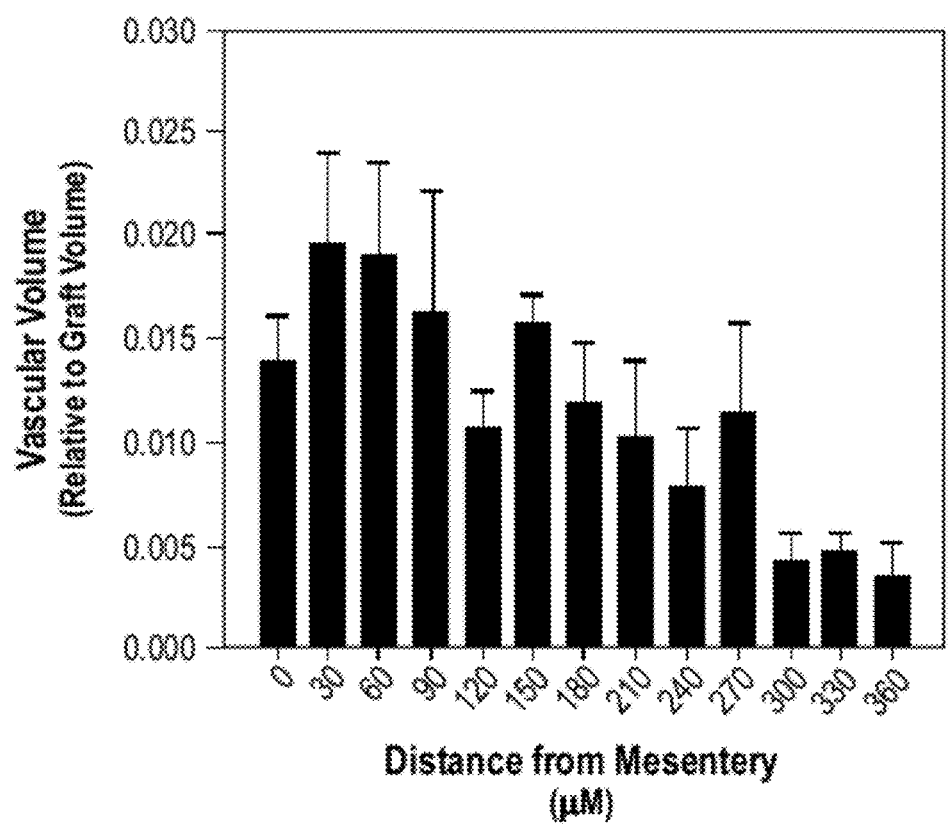

FIG. 3g: graphically depicts the quantification of vascular volume in extracted mimetic, based on 30 μm micro-CT slices from surface interfacing with host mesentery. The dashed line marks the expected opposite boundary surface of the liver mimetic based on its fabricated thickness of ~250 μm. Scale bars 5-mm, 2-mm, 5-mm.

Figure 4C:
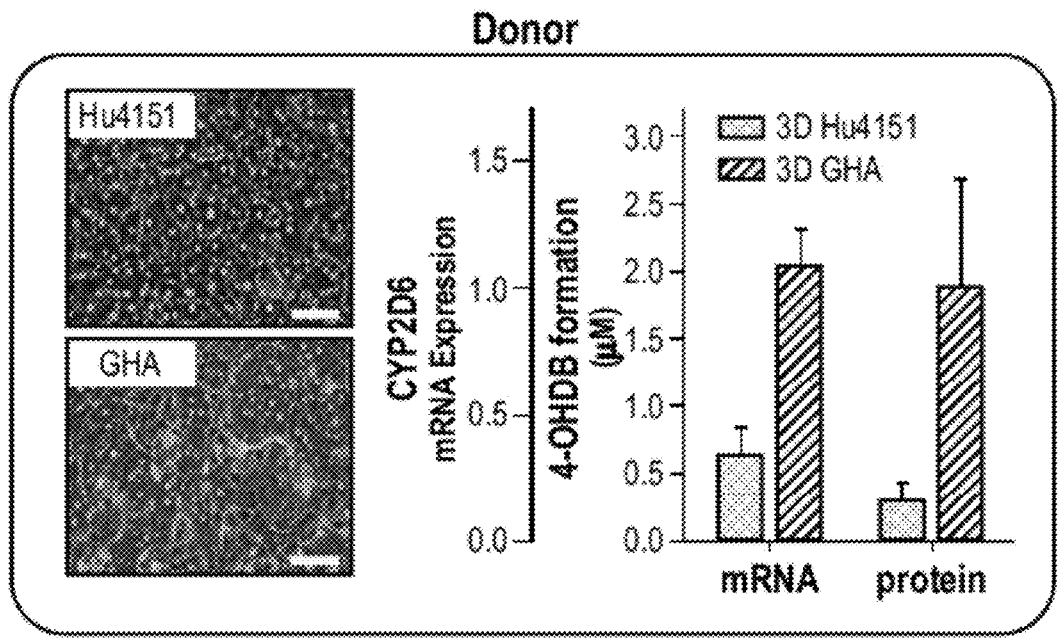
Figure 4C:
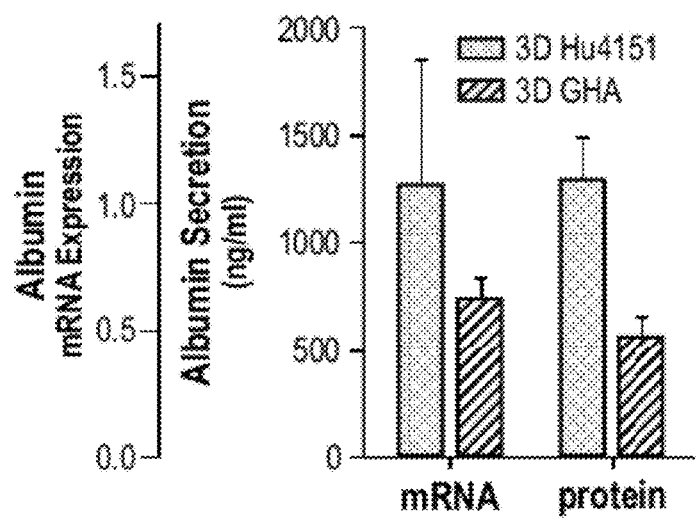

FIG. 4a: depicts representative micrographs of cryopreserved primary hepatocyte lots Hu4151 or GHA, co-cultivated with stromal fibroblasts for 7 days prior to 3D encapsulation. Scale bars 75 μm. (FIGS. 4a-d represent that humanized mice are modular for different donors or recipients, are amenable to drug dosing via multiple routes of administration, and are predictive of human drug metabolism, drug-drug interactions and toxicity).

FIG. 4b: graphically depicts the characterization of 3D Hu4151 or 3D GHA human liver mimetics for CYP2D6 mRNA expression by luminex PCR ('mRNA'), or CYP2D6 activity ('protein') by exposure to CYP2D6 substrate debrisoquine and quantification of debrisoquin hydroxylation.

FIG. 4c: graphically depicts the characterization of human liver mimetics made from different donors. Cryopreserved primary human hepatocyte lots Hu4151 and GHA were co-cultivated with fibroblasts (FIB), encapsulated with liver endothelial cells (LEC) in PEGDA+RGDS hydrogels and cultured in hepatocyte medium for 10 days. On day 10 post-encapsulation, total RNA was extracted from 3D Hu4151 or 3D GHA liver mimetics, and a luminex PCR assay was performed to quantify human albumin mRNA expression ('mRNA') relative to control gene transferin. Spent media sampled from cultured 3D Hu4151 or 3D GHA liver mimetics was also used to quantify human albumin secretion levels on day 2 post-encapsulation ('protein'). White bars represent 3D Hu4151 liver mimetics and striped bars represent 3D GHA liver mimetics. Error bars represent SEM for n=3.

Figure 4D:
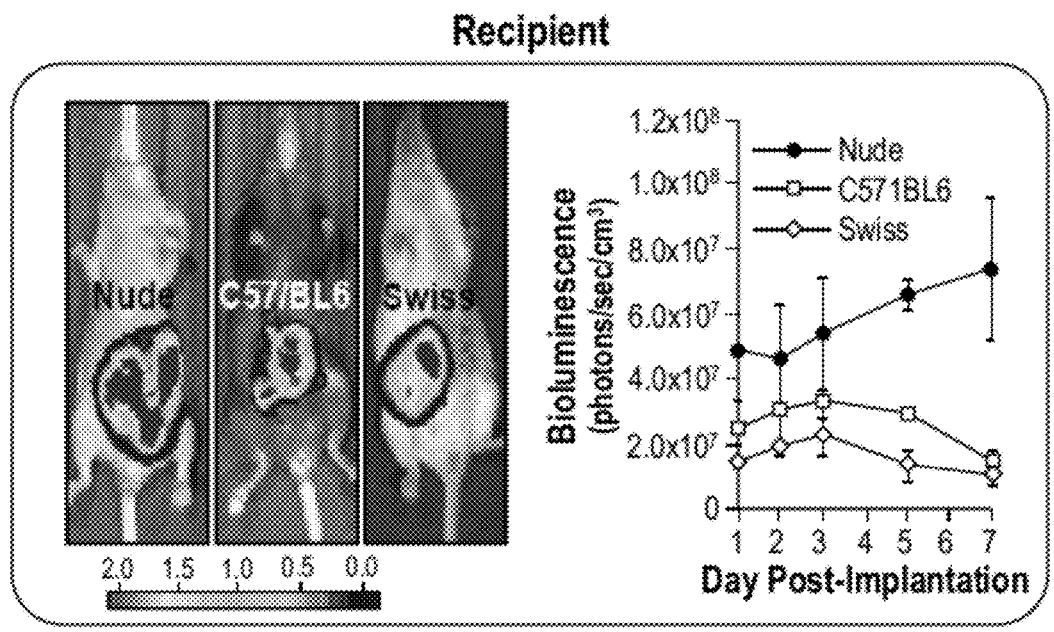

FIG. 4d: depicts in vivo bioluminescence imaging and quantitation of 3D Hu4151 human liver mimetics implanted in the intraperitoneal cavity of athymic nude, immune-competent C57/BL6 or immune-competent Swiss webster white mice. Shown are representative images acquired 3 d post-implantation.

Figure 4E:
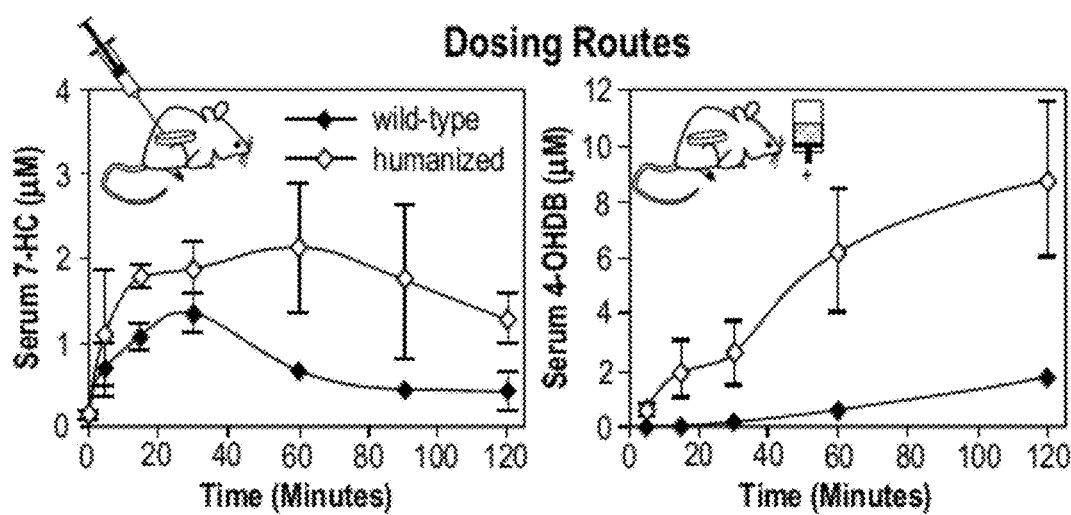

FIG. 4e: depicts the pharmacokinetic analysis of serum metabolite 7-hydroxycoumarin (7-HC) formation in humanized nude mice exposed to coumarin via i.p. injection (top), and serum metabolite 4-hydroxydebrisoquine (4-OHDB) formation in humanized C57/Bl6 mice exposure to debrisoquine via oral gavage (bottom).

Figure 4F:
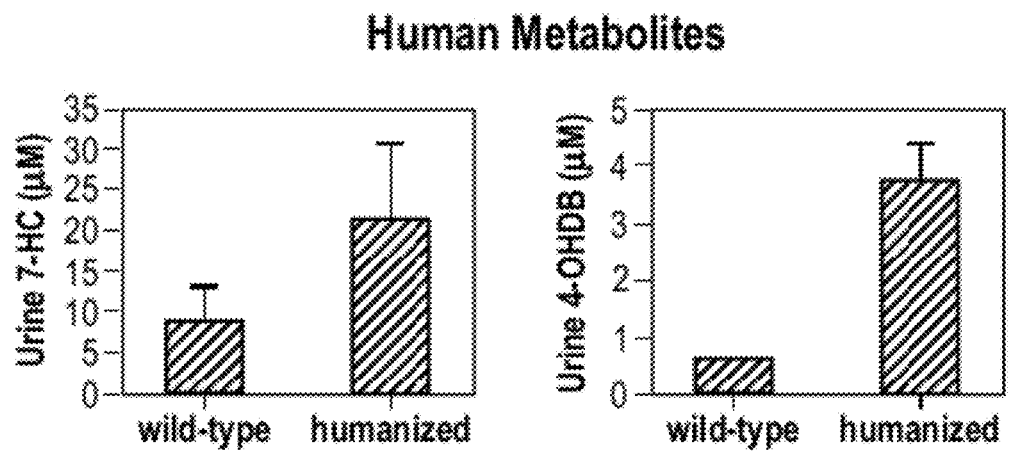

FIG. 4f: graphically depicts the detection of urinary metabolite excretion over 4 h in vivo.

Figure 4G:
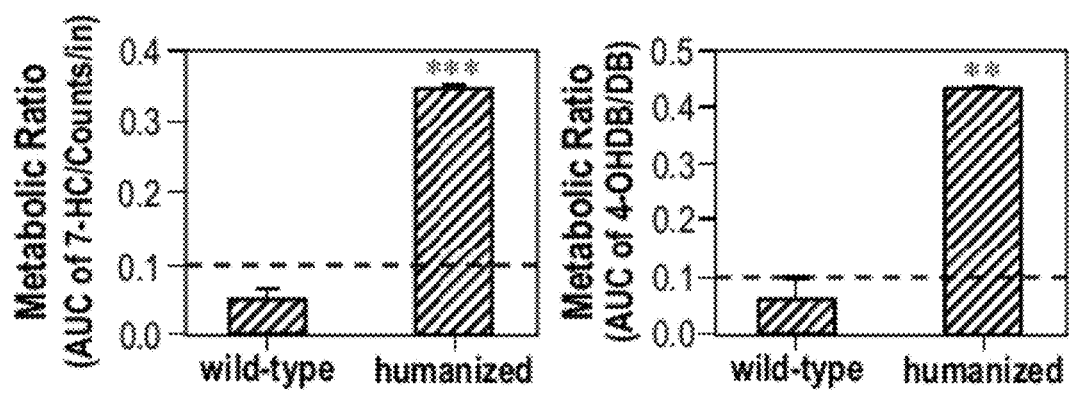

FIG. 4g: graphically depicts the identification of 'major' human metabolites in mice, based on calculation of the metabolic ratio (parent over metabolite exposure, based on the area under the curve (AUC)). The red dashed lines represent the lower threshold for classification as a 'major' human metabolite (0.1 or 10% AUC).

Figure 4H:
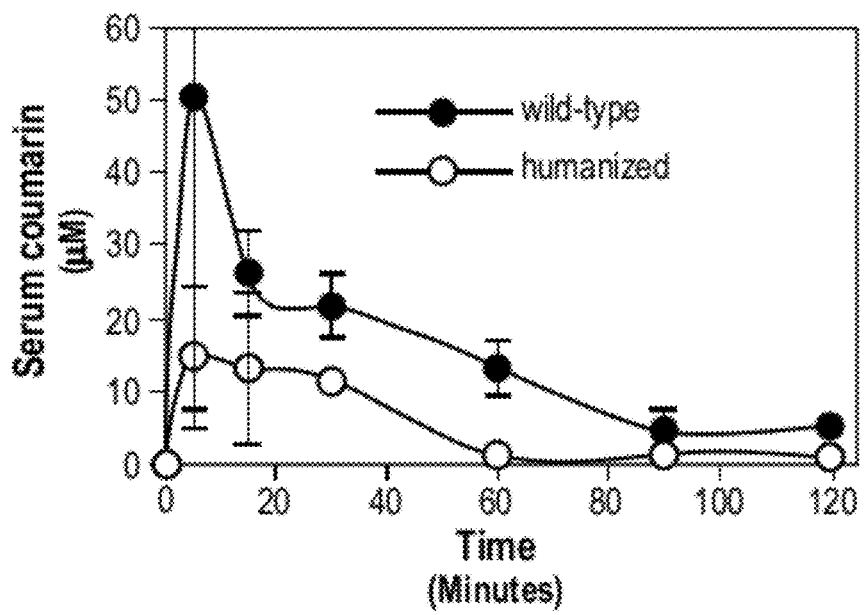

FIG. 4h: graphically depicts the pharmacokinetic analysis of the parent drug coumarin in humanized mice. Humanized mice established on a nude mouse background were administered coumarin at 80 mg/kg by intraperitoneal injection. Following drug administration, mice were bled by retro-orbital draw at specific timepoints, and drug concentration quantified by LC/MS/MS. Open circles represent humanized mice, and closed circles represent wild-type (no implant) mice. Error bars are SEM for n=3 mice per group.

Figure 4I:
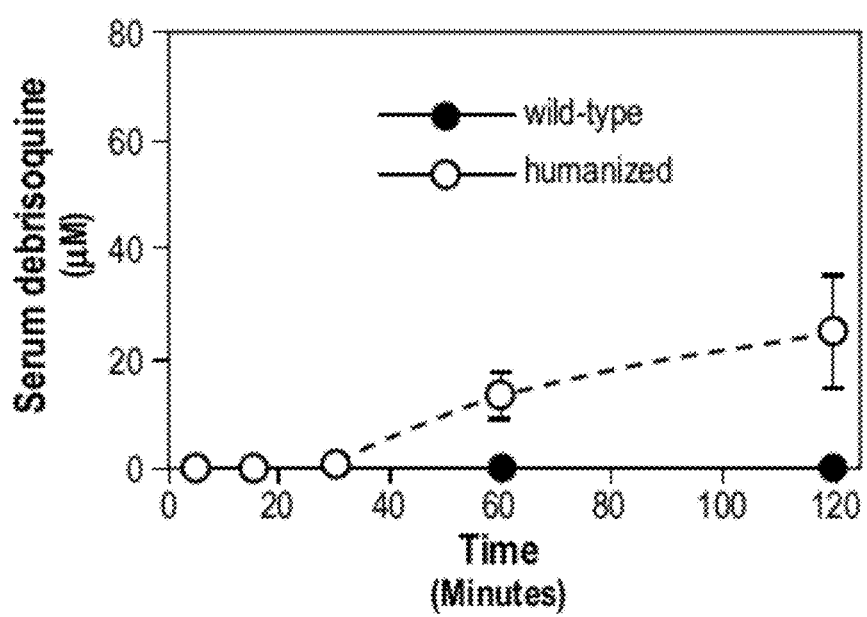

FIG. 4i: graphically depicts the pharmacokinetic analysis of the parent drug debrisoquine in humanized mice. Humanized mice established on a C57/Bl6 mouse background were administered debrisoquine at 2 mg/kg by oral gavage. Following drug administration, mice were bled by retro-orbital draw at specific timepoints, and drug concentration quantified by LC/MS/MS. Open circles represent humanized mice, and closed circles represent wild-type (no implant) mice. Error bars are SEM for n=3 mice per group.

Figure 5A:
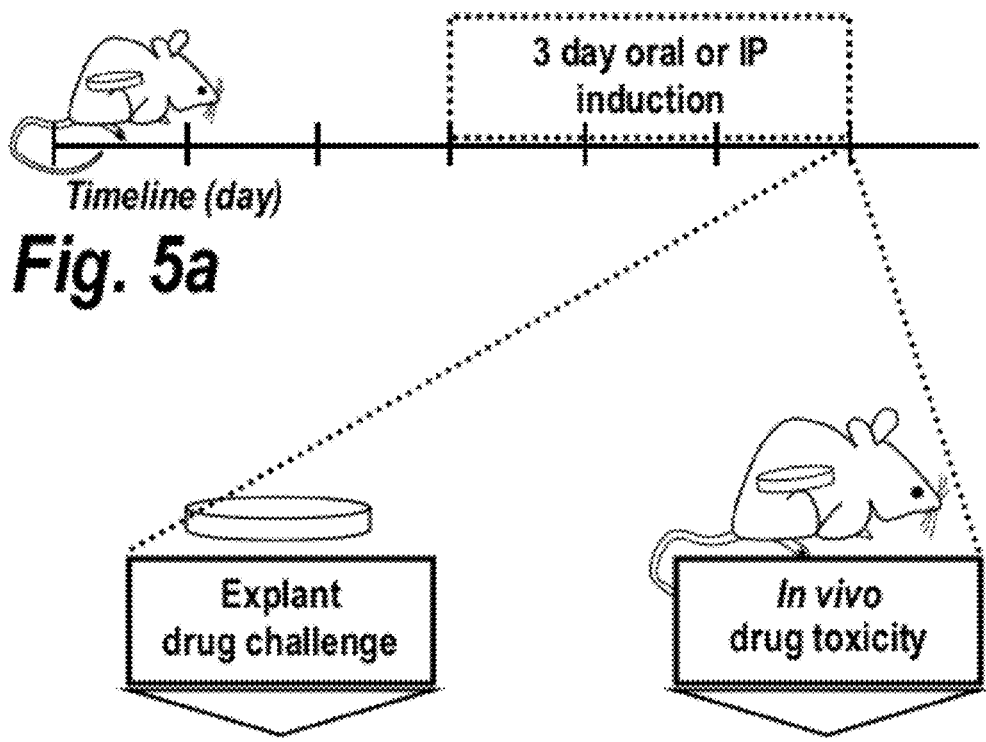

FIG. 5a: depicts a timeline of the drug-drug interaction study. Humanized mice (n=6 per group) were administered RIF (25 mg/kg) daily for 3 d before extraction of mimetic and incubation with CYP1A2 substrate ER or CYP3A4 substrate TEST ex vivo, or in vivo exposure to acetaminophen (APAP) and serum assessment of human hepatotoxicity.

Figure 5B:
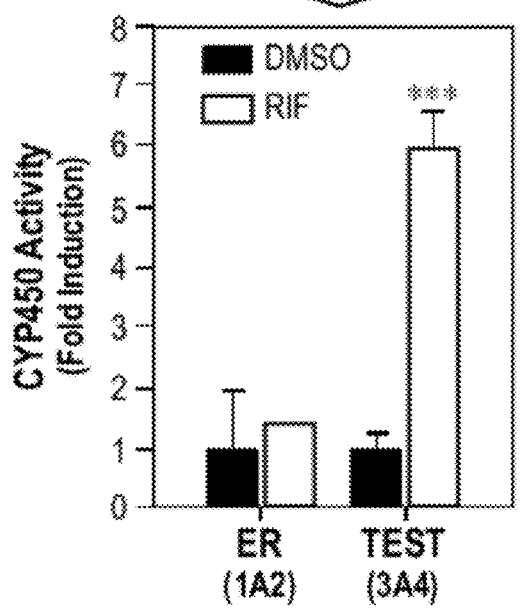

FIG. 5b: graphically depicts the extraction of mimetic and incubation with CYP1A2 substrate ER or CYP3A4 substrate TEST ex vivo. Fold-induction of CYP450 activity was determined by normalization to DMSO control. Human hepatotoxicity was determined by serum human albumin quantitation by ELISA. *p<0.01, p<0.05, *p<0.001 for n as indicated and SEM. Error bars are SEM for n=3 or greater.

Figure 5C:
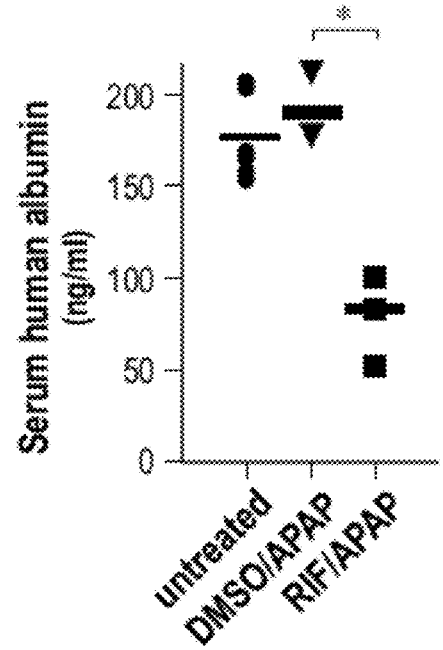

FIG. 5c: graphically depicts the in vivo exposure to acetaminophen (APAP) and serum assessment of human hepatotoxicity. *p<0.01, p<0.05, *p<0.001 for n as indicated and SEM. Error bars are SEM for n=3 or greater.

Figure 5D:
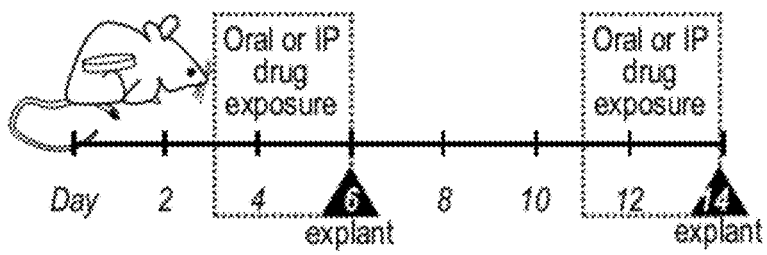

FIG. 5d: depicts a timeline of exposure to clinical inducer rifampin (RIF) in vivo, here administered at 20 mg/kg by intraperitoneal (IP) injection.

Figure 5E:
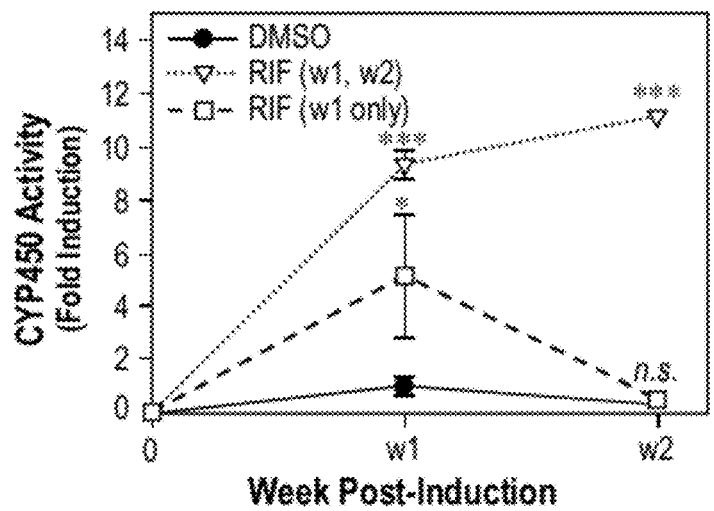

FIG. 5e: depicts the utility of humanized mice for predicting human drug responses; and graphically depicts the dynamics of CYP450 induction in mimetics exposed in vivo to IP-administered RIF over 1 or 2 weeks, with a washout period included in week 2 to determine if human liver mimetics were dynamically responsive to both the exposure and clearance of RIF. To assess CYP450 activity, humanized mice were administered RIF daily for 3 d before extraction of mimetic and incubation with 7-benzyloxy-4-trifluoromethylcoumarin (BFC) ex vivo. Fold-induction of CYP450 activity was determined by normalization to DMSO control. n.s. 'not significant', *p<0.01, p<0.05, *p<0.001 for n=6 mice per group and SEM.

Figure 5F:
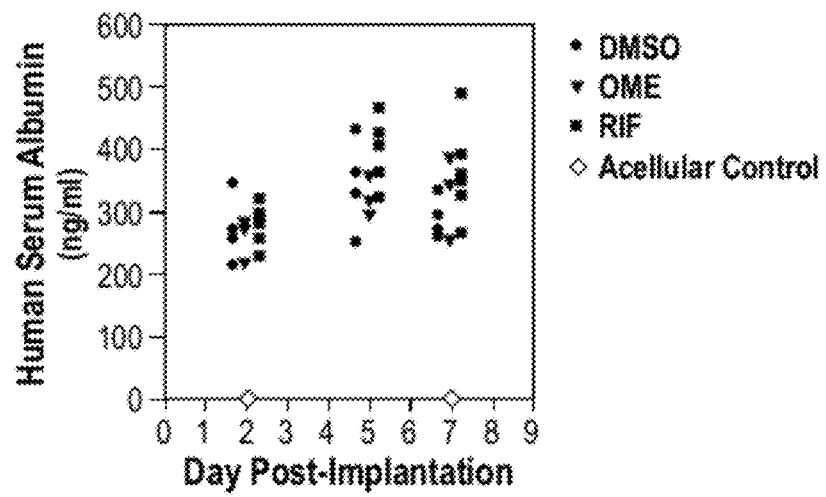

FIG. 5f: graphically depicts that human serum albumin from humanized mice is not affected by exposure to clinical drug inducers over time. Humanized mice were administered DMSO by intraperitoneal injection (circle), OME by oral gavage (40 µM, triangle), or RIF by intraperitoneal injection (25 µM, square), daily, at days 4-7 post-implantation. Blood was collected by retro-orbital draw on days 2, 5 and 7 days after implantation for drug-treated mice and control mice with acellular hydrogel intraperitoneal implantations. Red bars mark average human serum albumin levels at each timepoint for n=3-6 mice per condition.

Figure 5G:
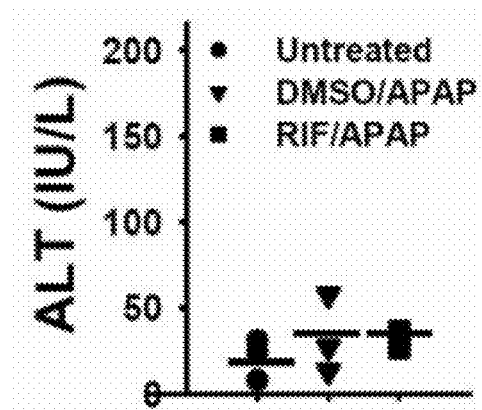

FIG. 5g: graphically depicts serum liver function tests. Humanized mice established for 7 d were exposed to no drug ('Untreated', circles) or inducer/drug combinations DMSO/APAP (triangles) or RIF/APAP (squares). Serum samples acquired at 4 h following APAP exposure were assayed for the liver damage marker alanine transaminase (ALT) using an endpoint colorimetric enzymatic assay.

Figure 5H:
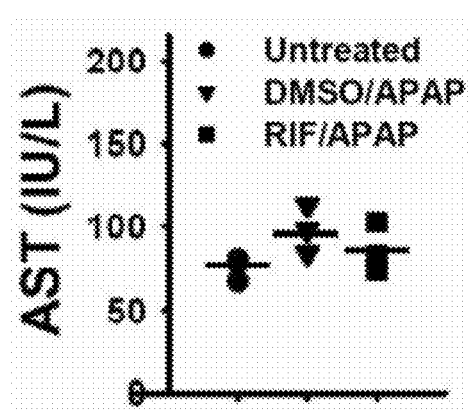

FIG. 5h: graphically depicts serum liver function tests. Humanized mice established for 7 d were exposed to no drug ('Untreated', circles) or inducer/drug combinations DMSO/APAP (triangles) or RIF/APAP (squares). Serum samples acquired at 4 h following APAP exposure were assayed for the liver damage markers aspartame transaminase (AST) using an endpoint colorimetric enzymatic assay. Shown are individual data points for n=3 mice per group, where black bars represent average values for each group.

Figure 5I:
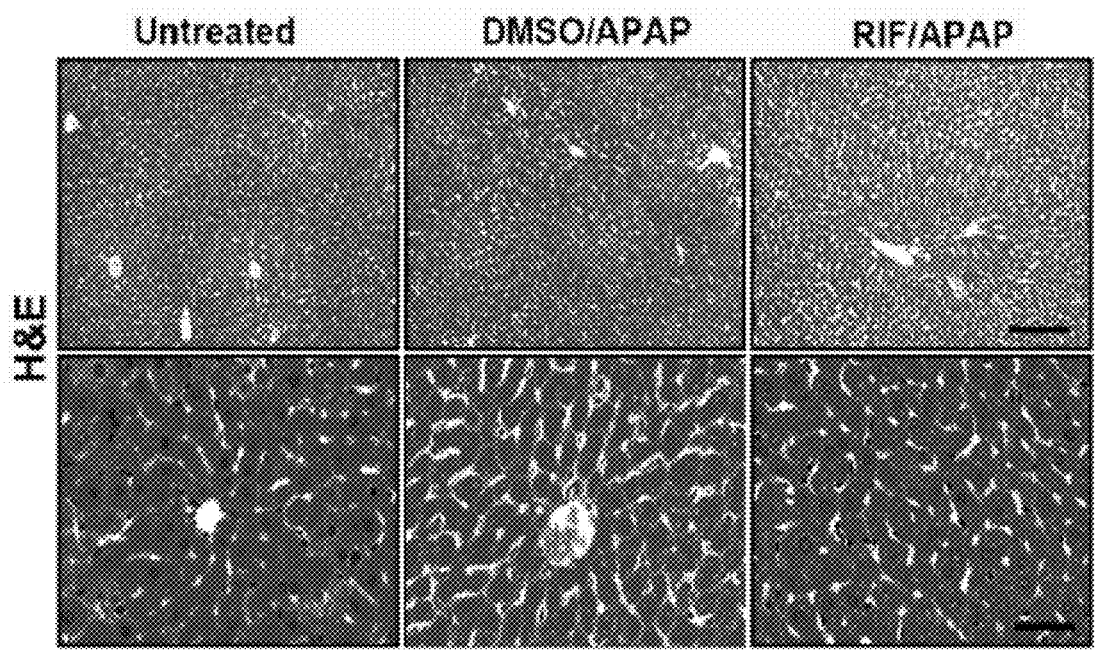

FIG. 5i: depicts liver histology for mice exposed to rifampin (RIF) and acetaminophen (APAP) combinations. Explanted livers were sectioned and stained with H&E. Shown are representative sections. Scale bars 270 µm (top) and 70 µm (bottom).

Figure 5J:
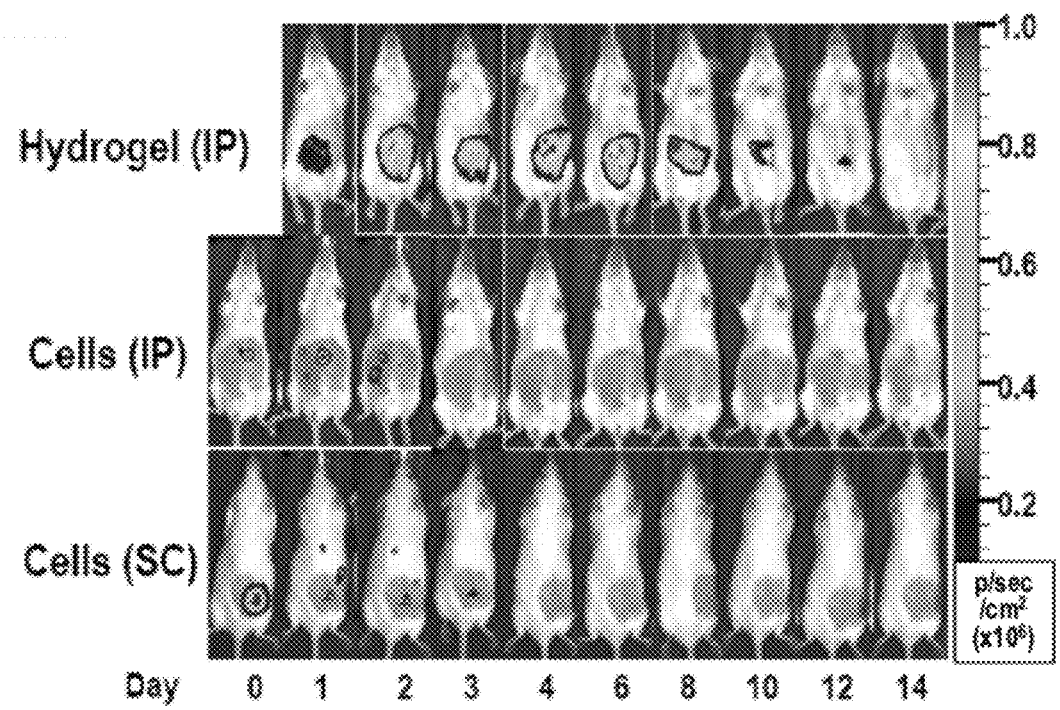

FIG. 5j: depicts the implantation of human liver mimetics and transplantation of human liver cells in immune-competent mice. Albumin-luciferase-reporter human HEP/FIB co-cultures were used for fabrication of liver mimetics implantation in the intraperitoneal cavity of Swiss Webster mice ('Hydrogel (IP)'), or for direct transplantation of ~1×10$^6$ hepatocytes in the intraperitoneal cavity ('Cells (IP)') or subcutaneous space ('Cells (SC)'). Implanted and transplanted mice were injected with 15 mg/ml luciferin/PBS solution, and bioluminescence imaging was performed using the Xenogen IVIS with Living Systems software to collect peak in vivo luminescence flux periodically over two weeks. Representative images are shown.

Figure 5K:
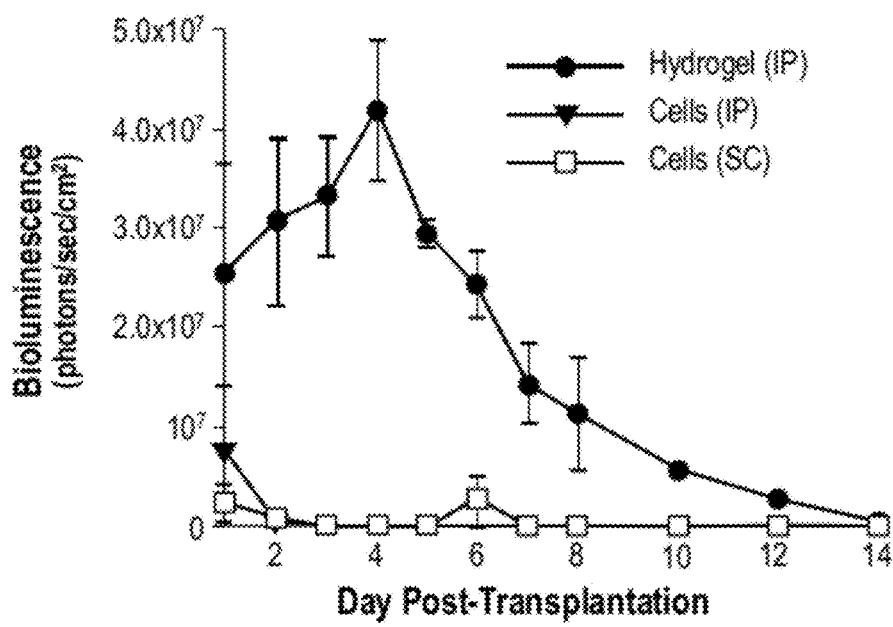

FIG. 5k: depicts the implantation of human liver mimetics and transplantation of human liver cells in immune-competent mice. Albumin-luciferase-reporter human HEP/FIB co-cultures were used for fabrication of liver mimetics implantation in the intraperitoneal cavity of Swiss Webster mice ('Hydrogel (IP)'), or for direct transplantation of ~1×10$^6$ hepatocytes in the intraperitoneal cavity ('Cells (IP)') or subcutaneous space ('Cells (SC)'). Implanted and transplanted mice were injected with 15 mg/ml luciferin/PBS solution, and bioluminescence imaging was performed using the Xenogen IVIS with Living Systems software to collect peak in vivo luminescence flux periodically over two weeks. Quantitation of bioluminescence images are shown for n=3 per group and error bars representing SEM.

Figure 6A:
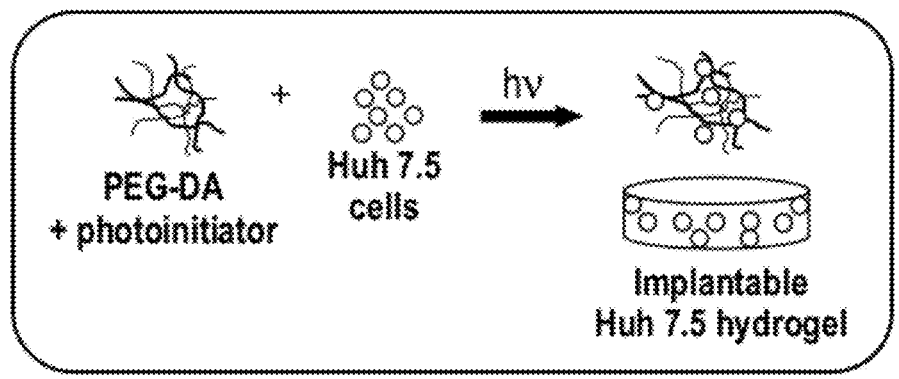

FIG. 6. Huh 7.5 constructs and implantation in nude mice. (A) Schematic depicting PEG-DA photoencapsulation of Huh 7.5 cells. (B) Viability assessment of 3D Huh 7.5 encapsulated in PEGDA (20 kDA, 10% w/v) at 6 hours and 5 days post-encapsulation, by the Live/Dead (Calcein AM/Ethidium Homodimer) stain. (C) Implantation of 3D Huh 7.5 constructs in athymic nude mice and measurement of human serum albumin indicates poor Huh 7.5 survival over time in vivo. *p<0.05 for n=4, Error bars: SEM.

FIG. 7 Engineering the PEG-DA microenvironment to improve 3D Huh 7.5 construct engraftment in nude mice. (A) Albumin secretion over time of Huh 7.5 encapsulated in PEG-DA (black squares), Huh 7.5 encapsulated in PEG-DA functionalized with 10 µmol/ml RGDS peptide (yellow triangles), or Huh 7.5/J2 fibroblast co-cultures encapsulated in PEG-DA with RGDS. (B) Left—Human serum albumin measured in nude mice following implantation of Huh 7.5 encapsulated in PEG-DA (black squares), Huh 7.5 encapsulated in PEG-DA with RGDS (yellow triangles), or Huh 7.5/J2 fibroblast co-cultures encapsulated in PEG-DA with RGDS. Right—Representative bioluminescence image of albumin promoter functions in nude mouse implanted with 3D Huh 7.5/J2+RGDS hydrogel. Huh 7.5 cells were pre-transduced with a lentivirus to express luciferase under the albumin promoter. n=4, and error bars represent SEM.

Figure 8:
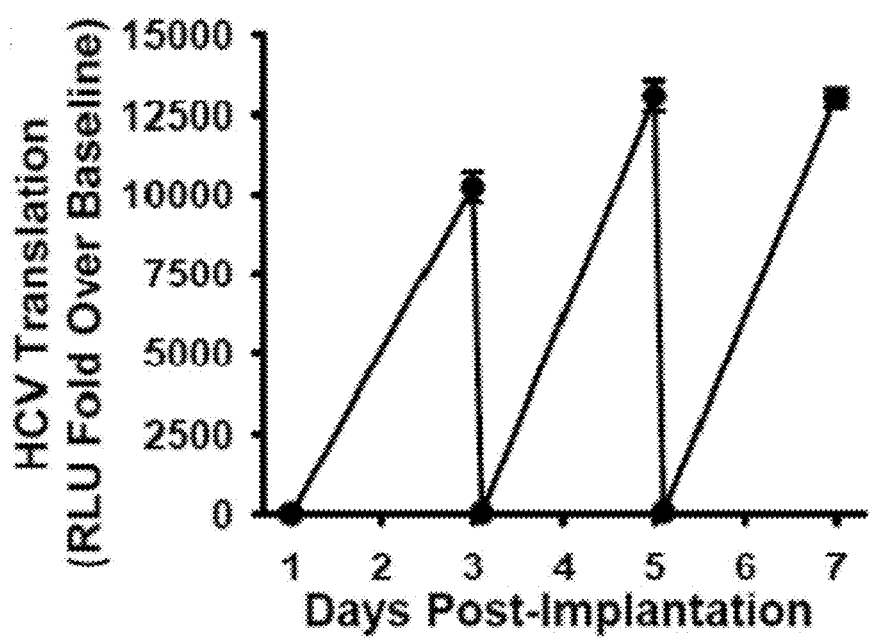

FIG. 8 HCV translation over time in 3D Huh 7.5 constructs infected with HCV-Gluc, a gaussia-luciferase expressing HCV reporter virus, in vitro. 3D Huh 7.5/J2+RGDS constructs were cultured for 4 d prior to inoculation with HCV-Gluc reporter virus (0.125 MOI, 24 h at 37 C). Starting at day 3 post-infection, media supernatant samples were taken every 48 and the media replaced with washing. Plot shows accumulated luciferase activity over time, including washed samples showing removal of residual Gluc protein.

Figure 9A:
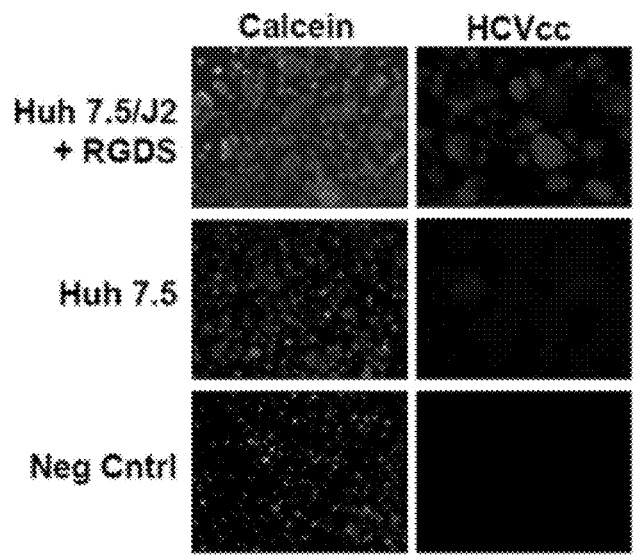

FIG. 9 Engineered 3D Huh 7.5 hydrogels infected with cell culture-derived HCV virus (HCVcc). (A) Epifluorescence images of representative day 7 Huh 7.5/J2+RGDS or Huh 7.5 hydrogels, stained with Calcein AM (green) on day 7 or infected with HCV-RFP reporter virus (red). Negative control hydrogels (Neg Cntrl) were Huh 7.5 hydrogels without HCV-RFP. (B) HCV copies detected by Q-PCR analysis of total RNA extracted from Huh 7.5/J2+RGDS, Huh 7.5 or Neg Cntrl hydrogels. n=4, error bars represent SEM.

Figure 10A:
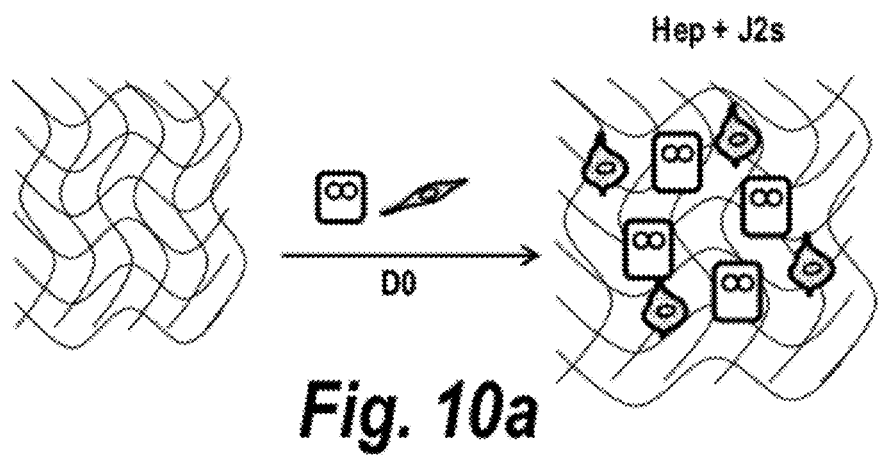
Figure 10B:
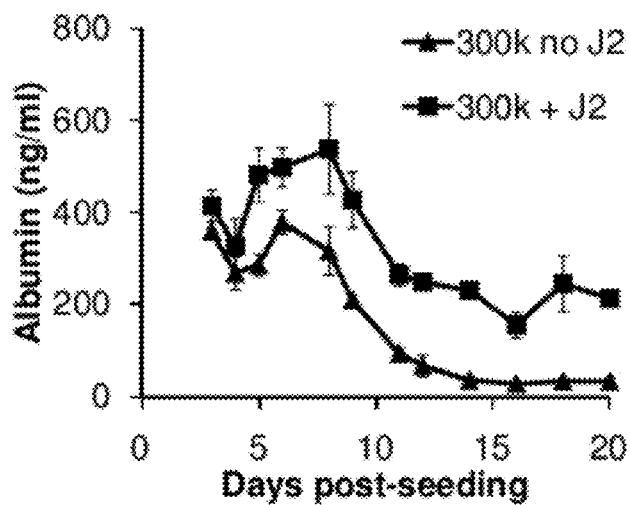
Figure 10C:
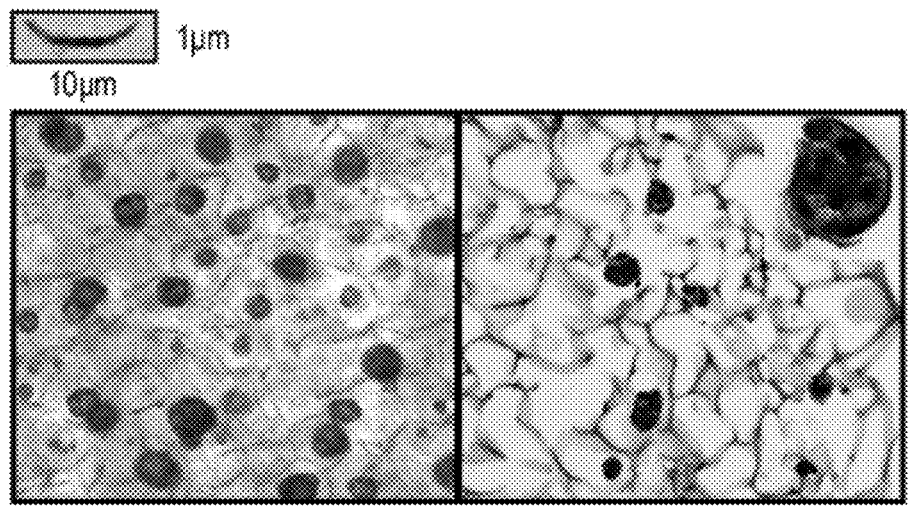

FIG. 10 depicts constructs comprising alginate (having a pore size sufficient to permit malaria sporozoite access) and hepatocytes/fibroblasts. FIG. 10a schematically depicts the constructs. FIG. 10b depicts albumin secretion by hepatocytes in the constructs. FIG. 10c depicts phase contrast imagine (left) and H&E staining (right) of the constructs.

FIG. 11: depicts in vitro infection of Alginate-encapsulated hepatoma or cocultured human hepatocytes by *P. berghei*-luciferase FIG. 12: depicts the response of Pb-luc-infected hepatoma aggregates in alginate to primaquine treatment.

DETAILED DESCRIPTION

To meet the demand for humanized animal, e.g., mouse, models with improved time-, labor- and cost-effectiveness, this invention presents an engineered human tissue amenable to facile manipulation, implantation and integration within a host animal, e.g., a non-injury mouse model. Tissue engineering—which typically combines cells, supporting biofactors, and biomaterial scaffolds towards restoring lost organ function in patients—has been applied towards generating cartilage, muscle and bone with moderate success (See e.g., Alsberg et al. (2002) Proc. Natl. Acad. Sci. USA. 99(19): p. 12025-30; and Griffith and Naughton (2002) Science 295(5557): p. 1009-14.). However, engineering certain tissue having advanced differentiated function, for example, hepatic tissue, continues to be particularly challenging due to the functional diversity, phenotypic instability and highly metabolic nature of transplanted cells (See e.g., Allen and Bhatia (2002) Tissue Eng. 8(5): p. 725-37; and Kulig and Vacanti (2004) Transpl. Immunol. 12(34):p. 303-10.). The present invention features a highly tunable hydrogel to promote the phenotypic stability of human cells (e.g., highly differentiated human cells) and also act as a delivery vehicle for implantation in vivo. Supporting biological and chemical cues are incorporated to pre-stabilize tissue-specific functions of primary cells, and facile implantation and in vivo integration of engineered tissues in a mouse model is demonstrated. This system offers significant advantages over currently available chimeric models because human cells are stable, highly functional and easily delivered in vivo without the need for genetic manipulation, engraftment or repopulation steps. This approach may be applied towards creating humanized animal models (e.g., rodent, for example, mouse, canine, for example, dog, primate, in particular, non-human primate, models, and the like) for a wide variety of human organ systems or organ diseases. Humanized animals having human tissue constructs comprising lung, kidney, nerve, heart, fat, bone, muscle, thymus, salivary gland, pancreas, adrenal, spleen, gall bladder, liver, thyroid, parayrhyroid, small intestine, uterus, ovary, bladder, skin, testes, prostate, or mammary gland cells, can envisioned featuring the technology of the instant invention.

In certain aspects, the invention features implantable human tissue construct, made of a biocompatible, polymer scaffold, e.g., a polyethylene (PEG) hydrogel, comprising a population of cells having a specific morphology, phenotype and/or highly differentiated function, and one or more biochemical factors supporting the specific morphology, phenotype and/or highly differentiated function. In exemplary embodiments, the specific morphology, phenotype and/or highly differentiated function is maintained for several weeks upon in vivo implantation into an animal. The one or more biochemical factors can include soluble factors supporting the specific morphology, phenotype and/or highly differentiated function and, optionally, further supporting cell viability. The one or more biochemical factors can include proteins, peptides, or other agents supporting adhesion of the cells to the polymer scaffold or hydrogel. In certain embodiments, the human tissue construct comprises at least one population of parenchymal cells having a specific morphology, phenotype and/or highly differentiated function. Exemplary cells include, but are not limited to hepatocytes, chondrocytes, adipocytes, myocytes, pancreatic cells, splenocytes, pancreatic islet cells, enterocytes, neurons, and other parenchymal cells described herein. The invention features use of normal (e.g., healthy) human cells, as well as diseased human cells (e.g., those harboring a genetic defect) for use in the constructs and/or animals of the invention.

In certain embodiments, the human tissue construct comprises at least one population of non-parenchymal cells, co-cultured in heterotypic contact with the parenchymal cells so as to support the specific morphology, phenotype and/or highly differentiated function and/or viability of the parenchymal cells. In other embodiments, the human tissue construct comprises at least one population of cells, optionally not in contact with the parenchymal cells (or parenchymal cell:non-parenchymal cell co-cultures), wherein the population further supports the morphology, phenotype, function and/or viability of the parenchymal cells (or co-cultures comprising same), for example, by secreting or producing factors, e.g., soluble factors, of biochemical cues that support said morphology, phenotype, function or viability. Co-encapsulated non-parenchymal cells can also have the dual function of supporting the differentiated morphology, phenotype and/or function of the parenchymal cells and effecting the host environment or microenvironment surrounding the implanted constructs. For example, non-parenchymal cells encapsulated in the constructs of the invention can secrete, e.g., growth factors and/or cytokines that promote vascularization of the constructs in vivo. Without being bound in theory, it is also contemplated that the non-parenchymal cells encapsulated in the constructs of the invention may play a role in recruiting, for example, inflammatory cells, thus mediating (e.g., promoting or deterring) interaction with the immune system of the host animal (e.g., a bidirectional interaction between the implanted construct and the surrounding environment.

It is also contemplated that certain parenchymal cells are amenable to culturing in the constructs on the invention absent a co-cultured non-parenchymal cell population, for example, where the parenchymal cells are encapsulated, or pre-treated (e.g., pre-cultured) in the presence of sufficient factors to stabilize said cells. For example, it is believed that parenchymal cells, for example, hepatocytes can be pre-treated or pre-cultured in the presence of a kinase inhibitor, e.g., a PI3K inhibitor, such that stabilization occurs. In such a manner, it is possible to mitigate, in certain embodiments, the need for non-parenchymal cells to some extent.

The skilled artisan will appreciate that various encapsulation formats are possible and that variation of the encapsulation format can be made to optimize the desired function of the construct. For example, in some embodiments, the parenchymal cells and one or more populations of non-parenchymal cells can be in contact, e.g., heterotypic contact between parenchymal cells and one or more populations of non-parenchymal cells, optionally with heterotypic contact between various populations of non-parenchymal cells. However, due to the soluble nature of certain biochemical cues secreted by the non-parenchymal cells, cell-cell contact is not necessarily required in the constructs of the invention.

Such constructs are particularly suited for implantation in an animal, e.g., a mouse, to produce a humanized animal having an engineered human tissue or HEAL. In such fashion, humanized animals are made having a host of uses, in particular, in pharmaceutical development and as animal models of disease.

In exemplary embodiments, the invention features polymer-based hydrogels made of synthetic or natural, cross-linkable polymers, for encapsulating parenchymal and non-parenchymal cells. In preferred embodiments, the invention features a photopolymerizable polyethylene glycol (PEG) hydrogel platform that is uniquely suited for building a functional implantable liver human tissue constructs due to the highly tunable chemical and architectural properties of these scaffolds. Polyethylene glycol (PEG) based hydrogels are ideal tissue engineering scaffolds because they are biocompatible, hydrophilic, and immunologically inert (See e.g., Nguyen and West (2002) Biomaterials 23(22): p. 4307-14; Peppas et al. (2002) Eur. J. Pharm. Biopharm. 50(1): p. 27-46; Albrecht et al. (2005) *Lab Chip* 5, 111-118; Albrecht et al. (2006) *Nat. Methods* 3, 369-375; Liu and Bhatia (2002) *Biomedical Microdevices* 4, 257-266; and Underhill et al. (2007) *Biomaterials* 28, 256-270). The photopolymerizable PEG used in certain embodiments of the invention, PEG-diacryate (PEGDA), is cross-linked rapidly by combining acrylate-end-modified monomers, photoinitiator and UV light. Other embodiments feature polymerizable PEG bearing non-photochemically polymerizable moieties. This process can be used to encapsulate cells and distribute them homogenously throughout the hydrogel scaffold.

In exemplary embodiments, the invention features the development and application of an implantable, tissue-engineered human liver construct, used to establish a humanized mouse model for the study of human liver biology in vivo. To make the humanized mouse, engineered human liver tissue is derived from human hepatocytes that are pre-stabilized in vitro then cultured within a customized polymer delivery scaffold disc and implanted, ectopically, in vivo. The liver has been of particular interest for humanization in mice, due primarily to the liver's role in xenobiotic metabolism and drug toxicity. In human patient clinical trials, drug-induced liver toxicity and adverse drug reactions cause about 50-60% of pharmacological candidates to fail in Phase I clinical trials (See e.g., Olson et al. (2000) Regul Toxicol Pharmacol 32(1): p. 56-67; and Xu et al. (2004) Chem. Biol. Interact. 150(1): p. 115-28.). This failure rate has been attributed to the poor predictive capacity of pre-clinical in vitro and in vivo drug screens: current animal toxicology models are limited by species-specific differences in drug metabolism pathways, while in vitro human toxicology models are difficult to stabilize in culture and cannot simulate physiologic multi-organ effects or treatment responses (See e.g., Brandon et al. (2003) Toxicol Appl Pharmacol 189(3): p. 233-46; and Wienkers and Heath (2005) Nat. Rev. Drug. Discov. 4(10): p. 825-33.).

Unlike existing models, the present invention features a tissue-engineered human liver construct implanted in the mouse, which is optimized to retain hepatocyte morphology, phenotype and differentiated functions normally lost when hepatocytes are isolated from the human body. The invention features a highly tunable, synthetic (polyethylene glycol, PEG) hydrogel system that has been optimized and adapted to photo-encapsulate homogenous distributions of hepatocyte:stromal cell co-cultures within defined structural features. The engineered human liver mimetics exhibiting stable liver functions are established in ~1 week in vitro and implanted in vivo. Using the engineered constructs of the invention avoids any requirement for repopulation of the mouse liver in order to rescue the mouse from liver failure. Accordingly, in vivo studies can be performed readily, and species-specificity confirmed systemically (i.e. using human-specific drug substrates), or for the first time, on a per construct basis (i.e. upon explanting liver tissues). Using non-invasive imaging techniques, it has been demonstrated that human liver constructs function in mice for >4 weeks, integrate with host vasculature, and faithfully predict human drug metabolism activity and gene expression (e.g., human cytochrome P450-mediated drug responses and human-specific metabolite formation.) It has further been demonstrated that the human liver constructs of the invention can be reproducibly and chronically infected with virus (e.g., HCV) both in vivo and in vitro, modeling infectious disease.

Current methods for studying human liver functions in vivo are limited to insufficient humanization, or to breeding and surgical complications, lengthy cell engraftment and expansion times, and low repopulation efficiency. The technologies of the instant invention enable the skilled artisan to effectively screen human liver responses to pharmacologic drugs in vivo without relying on the genetics, breeding or surgical expertise required by current art. The current invention is therefore uniquely scalable and amenable to manu-facturing processes in pharmaceutical industry or academia. In addition, this invention has new capabilities not feasible with art-described cell transplantation or hepatic tissue engineering methods. Engineered human constructs may be used to create humanized mice from immune-competent or diseased hosts, as PEG polymers have been utilized previously for immunoisolation of transplanted pancreatic islet cells (Cruise et al. (1999) *Cell Transplantation* 8, 293-306 and Cruise et al. (1998) *Biomaterials* 19, 1287-1294). Engineered liver constructs are amenable to metabolic and/or toxicology testing, anti-viral compound testing, end the like. Engineered liver constructs are also conducive to multiplexing, whereby hepatocytes from different liver donors may be simultaneously implanted and compared in the same host animal. Only in this tissue-engineered humanized mouse model can both the liver tissue and host background be so readily exchanged, tested and compared. Accordingly, this technology can dramatically improve drug and/or drug safety testing and potentially transform in vivo human liver research.

So that the invention may be more readily understood, certain terms are first defined.

As used herein, the term "co-culture" refers to a collection of cells cultured in a manner such that more than one population of cells are in association with each other. Co-cultures can made such that cells exhibit heterotypic interactions (i.e., interaction between cells of populations of different cell types), homotypic interactions (i.e., interaction between cells of the same cell types) or co-cultured to exhibit a specific and/or controlled combination of heterotypic and homotypic interactions between cells.

As used herein, the term "encapsulation" refers to the confinement of a cell or population of cells within a material, in particular, within a biocompatible polymeric scaffold or hydrogel. The term "co-encapsulation" refers to encapsulation of more than one cell or cell type or population or populations of cells within the material, e.g., the polymeric scaffold or hydrogel.

As used herein, the term "biochemical factor" or "biochemical cue" refers to an agent of a chemical nature having a biological activity, for example, on a cell or in a tissue. Exemplary biochemical factors or cues include, but are not limited to growth factors, cytokines, nutrients, oxygen, proteins, polypeptides and peptides, for example, adhesion-promoting proteins, polypeptides and peptides, and the like. Exemplary adhesion-promoting peptides include those derived from the extracellular matrix (ECM) of a cell or tissue, including, but not limited to collagen-derived peptides, laminin-derived peptides, fibronectin-derived peptides (e.g., the RGD-peptides), and the like. Biochemical factors or biochemical cues can be utilized in the constructs of the invention to stabilize parenchymal cell populations and/or to differentiate or maintain parenchymal cell populations, e.g., precursor or progenitor cell populations.

Co-cultures can be maintained in vitro or can be included in engineered tissue constructs of the invention, maintained in vitro and/or implanted in vivo. For example, the instant inventors have established critical biological and chemical parameters for stabilizing hepatocyte functions in PEG hydrogel constructs (See e.g., Liu Tsang (2007) Faseb. J. 21(3): p. 790-801; and Underhill et al. (2007) 28(2): p. 256-70.). In particular, the inventors co-culture hepatocytes with supporting nonparenchymal cell types (e.g., fibroblasts) in vitro within PEG polymer networks (See e.g., Bhatia et al. (1999) Faseb. J. 13(14): p. 1883-900; Khetani and Bhatia (2008) Nat. Biotechnol. 26(1): p. 120-6; and Khetani et al. (2004) Hepatology 40(3): p. 545-54.). Co-cultivation of hepatocytes with non-parenchymal fibroblast cells prior to encapsulation improves hepatocyte survival compared to hepatocytes alone, with hepatocytes alone surviving only a day, versus co-cultured hepatocytes surviving (and synthesizing urea) out past 5 days. This demonstrates the importance of cell-cell interactions in promoting hepatocellular viability and functions in a 3D context. The microenvironment within in the PEG-based hydrogels is further tuned to exploit the importance of facilitate cell:matrix interactions within implantable constructs by conjugating to the polymer backbone peptides derived from extracellular-matrix molecules. In particular, tethered RGDS from fibronectin improves encapsulated hepatocellular functions (albumin secretion, urea synthesis) compared to PEG alone or a negative control peptide RGES. The geometry of the construct is further optimized to provide thick layers of encapsulated hepatocytes adequate nutrient and diffused $O_2$ supply. Specifically, a stereolithography-based photopatterning technique is used to control light exposure to cell-polymer solutions and thereby fabricate intricate cell-hydrogel architectures (See e.g., Liu and Bhatia (2002) Biomedical Microdevices 4(4): p. 257-266; and Liu Tsang (2007) Faseb. J. 21(3): p. 790-801.). It has been demonstrated that introduction of perfusion channels using a single-layer hexagonal branching pattern (e.g., 500 µm thick branches) significantly improves diffusive transport of oxygen and nutrients to photoencapsulated hepatocytes. In particular, it has been shown that mitochondrial activity of cells is uniformly stained in the hexagonal patterned construct compared to the unpatterned construct, which experiences diffusive transport limitations to innermost cells.

As used herein, the term "hydrogel" refers to a network of polymer chains that are hydrophilic in nature, such that the material absorbs a high volume of water or other aqueous solution. Hydrogels can include, for example, at least 70% v/v water, at least 80% v/v water, at least 90% v/v water, at least 95%, 96%, 97%, 98% and even 99% or greater v/v water (or other aqueous solution). Hydrogels can comprise natural or synthetic polymers, the polymeric network often featuring a high degree of crosslinking. Hydrogels also possess a degree of flexibility very similar to natural tissue, due to their significant water content. Hydrogel are particularly useful in tissue engineering applications of the invention as scaffolds for culturing cells. In preferred embodiments of the invention, the hydrogels are made of biocompatible polymers. Hydrogels of the invention are preferably non-biodegradable to facilitate explant of construct comprised thereof. At least one unexpected feature of the invention is that nondegradable hydrogels (scaffolds) become sufficiently vascularized upon implantation of the constructs of the invention to facilitate long-term survival of the constructs as deliver oxygen, nutrients and drugs (e.g., test drugs) to the constructs implanted in vivo.

As used here, the term "parenchymal cells" refers to cells of, or derived from, the parenchyma of an organ or gland, e.g., a mammalian organ or gland. The parenchyma of an organ or gland is the functional tissue of the organ or gland, as distinguished from surrounding or supporting or connective tissue. As such, parenchymal cells are attributed with carrying out the particular function, or functions, of the organ or gland, often referred to in the art as "tissue-specific" function. Parenchymal cells include, but are not limited to, hepatocytes, pancreatic cells (alpha, beta, gamma, delta), myocytes, e.g., smooth muscle cells, cardiac myocytes, and the like, enterocytes, renal epithelial cells and other kidney cells, brain cell (neurons, astrocytes, glia cells), respiratory epithelial cells, stem cells, and blood cells (e.g., erythrocytes and lymphocytes), adult and embryonic stem cells, blood-brain barrier cells, adipocytes, splenocytes, osteoblasts, osteoclasts, and other parenchymal cell types known in the art.

Because parenchymal cells are responsible for tissue-specific function, parenchymal cells express or secrete certain tissue specific markers. In the liver, for example, liver tissue specific proteins include, but are not limited to, albumin, fibrinogen, transferrin, and cytokeratin 19. The functional activity of a particular parenchymal cell can vary with the type of non-parenchymal cell included within constructs of the invention. For example, the quantity and rate of expression of albumin by hepatocytes in co-culture can vary between the type of fibroblast cell line used in a construct of the invention.

Certain precursor cells can also be included as "parenchymal cells", in particular, if they are committed to becoming the more differentiated cells described above, for example, liver progenitor cells, oval cells, adipocytes, osteoblasts, osteoclasts, myoblasts, stem cells (e.g., embryonic stem cells, hematopoietic stem cells, mesenchymal stem cells, endothelial stem cells, fetal stem cells, induced pluripotent stem cells, commonly abbreviated as iPS cells or iPSCs, and the like.) In some embodiments stem cells can be encapsulated and/or implanted under specified conditions such that they are induced to differentiate into a desired parenchymal cell type, for example, in the construct and/or in vivo. It is also contemplated that differentiated parenchymal cells derived from a distinct differentiated parenchymal cells, e.g., neuron-derived hepatocytes, can be used in the constructs of the invention. It is also contemplated that parenchymal cells derived from cell lines can be used in the methodologies of the invention.

The term "non-parenchymal cells" as used herein, refers to the cells of or derived from the tissue surrounding or supporting aprenchymal tissue in an organ or gland, for example, in a mammalian (e.g., human) organ or gland, or the connective tissue of such an organ or gland. Exemplary non-parenchymal cells include, but are not limited to, stromal cells (e.g., fibroblasts), endothelial cells, stellate cells, cholangiocytes (bile duct cells), Kupffer cells, pit cells, and the like. The choice of non-parenchymal cells used in the constructs of the invention will depend upon the parenchymal cell types used. For example, a variety of both liver and non-liver derived non-parenchymal cells have been reported to induce hepatic function in co-culture. Furthermore, induction has been reported by non-parenchymal cells (both primary and immortalized) derived from a different species than the primary hepatocytes, suggesting possible conservation of underlying mechanisms. The ready availability and ease of culture of immortalized cells, including immortalized non-human cells (e.g., murine fibroblasts) has led to a resurgence of interest in their influence on parenchymal cell (e.g., hepatocyte) functions for applications in tissue engineering.

As used herein, the term "hepatocellular function" refers to a function or activity of a hepatic cell (e.g., a hepatocyte) characteristic of, or specific to, the function of liver parenchymal cells, e.g., liver-specific function. Hepatocellular functions include, but are not limited to albumin secretion, urea production, liver-specific transcription factor activity, metabolism, e.g., drug metabolism. In certain exemplary embodiments, the hepatocellular function is drug metabolism, for example, the enzymatic activity of human Phase I detoxification enzymes (e.g., cytochrome P450 activity), human Phase II conjugating enzymes, human Phase III transporters, and the like. For example coumarin 7-hydroxylation is a human-specific process mediated by human Phase I metabolic enzymes, e.g., CYP2A6 or CYP2A2, in response to know substrates and/or inducers.

Maintenance of hepatocellular function can result from maintaining the desired morphology, cell-cell contact, environmental biochemical cues, adhesion, and the like, and within constructs of the invention, can further result from promoting sufficient vascularization and oxygen and nutrient transport to the implanted construct.

As used herein, the term "ectopic" means occurring in an abnormal position or place. Accordingly, "implantation at an ectopic site" means implantation at an abnormal site or at a site displaced from the normal site. Exemplary ectopic sites of implantation include, but are not limited to the intraperitoneal space and ventral subcutaneous space. Ectopic sites of implantation can also be within an organ, i.e., an organ different than that of the source cells of the construct being implanted (e.g., implanting a human liver construct into the spleen of an animal). Ectopic sites of implantation can also include other body cavities capable of housing a construct of the invention. In some embodiments, ectopic sites include, for example, lymph nodes. At least one unexpected feature of the invention is that constructs implanted at ectopic sites in the humanized animals of the invention survive and maintain differentiated function for significant periods of time. This is in contrast to the art-recognized belief that implantation at an orthotopic site is required to provide trophic factors necessary to support viability (e.g., trophic factors from the gut necessary to support viability in transplanted hepatocyte systems). The term "ectopic" and "heterotropic" can be used interchangeably herein.

As used herein, the term "infection" refers to the colonization of a host tissue (e.g., a tissue construct of the invention) by a parasitic species, for example, a virus, prion, bacteria, protozoa, parasite, viriod, etc. Infection can include reproduction of the infecting agent. As used herein, the term "infectious disease" a disease resulting from the infection, presence and/or growth of an infectious agent, e.g., pathogen, in a host tissue or organism. As used herein the term "pathogen" or "infectious agent" is an agent, for example, a virus, prion, bacteria, protozoa, parasite, viriod, etc., that causes infection (e.g., in a tissue or organism) and/or disease (e.g., in an organism).

As used herein and in the appended claims, the singular forms "a," "and," and "the" include plural referents unless the context clearly dictates otherwise. Thus, for example, reference to "a cellular island" includes a plurality of such cellular islands and reference to "the cell" includes reference to one or more cells known to those skilled in the art, and so forth.

I. Cell Sources

Parenchymal cells can be obtained from a variety of sources including, but not limited to, liver, skin, pancreas, neuronal tissue, muscle, and the like. Parenchymal cells can be obtained from parenchymal tissue using any one of a host of art-described methods for isolating cells from a biological sample, e.g., a human biological sample. Parenchymal cells. e.g., human parenchymal cells, can be obtained by biopsy or from cadaver tissue. In certain embodiments, parenchymal cells are derived from lung, kidney, nerve, heart, fat, bone, muscle, thymus, salivary gland, pancreas, adrenal, spleen, gall bladder, liver, thyroid, parathyroid, small intestine, uterus, ovary, bladder, skin, testes, prostate, or mammary gland.

In exemplary aspects, the invention employs constructs containing human parenchymal cells optimized to maintain the appropriate morphology, phenotype and cellular function conducive to use in the methods of the invention. Primary human parenchymal cells can be isolated and/or pre-cultured under conditions optimized to ensure that the parenchymal cells of choice (e.g., hepatocytes) initially have the desired morphology, phenotype and cellular function and, thus, are poised to maintain said morphology, phenotype and/or function in the constructs, and in vivo upon implantation to create the humanized animals of the invention Cells useful in the methods of the disclosure are available from a number of sources including commercial sources. For example, hepatocytes may be isolated by conventional methods (Berry and Friend, 1969, J. Cell Biol. 43:506-520) which can be adapted for human liver biopsy or autopsy material. In general, cells may be obtained by perfusion methods or other methods known in the art, such as those described in U.S. Pat. Pub. No. 20060270032.

Parenchymal and non-parenchymal cell types that can be used in the above-described constructs include, but are not limited to, hepatocytes, pancreatic cells (alpha, beta, gamma, delta), myocytes, enterocytes, renal epithelial cells and other kidney cells, brain cell (neurons, astrocytes, glia), respiratory epithelium, stem cells, and blood cells (e.g., erythrocytes and lymphocytes), adult and embryonic stem cells, blood-brain barrier cells, and other parenchymal cell types known in the art, fibroblasts, endothelial cells, and other non-parenchymal cell types known in the art.

Typically, in practicing the methods of the disclosure, the cells are mammalian cells, although the cells may be from two different species (e.g., humans, mice, rats, primates, pigs, and the like). The cells can be primary cells, or they may be derived from an established cell-line. Cells can be from multiple donor types, can be progenitor cells (e.g., liver progenitor cells), tumor cells, immortalized cell lines, and the like. In preferred embodiments, the cells are freshly isolated cells (for example, encapsulated within 24 hours of isolation), e.g., freshly isolated hepatocytes from cadaveric donor livers. Although any combination of cell types that promotes maintenance of differentiated function of the parenchymal cells can be used in the methods and constructs of the invention (e.g., parenchymal and one or more populations of non-parenchymal cells, e.g., stromal cells), exemplary combinations of cells for producing the constructs include, without limitation: (a) human hepatocytes (e.g., primary hepatocytes) and fibroblasts; (b) hepatocytes and fibroblasts and endothelial cells; and (c) human hepatocytes and more than one population of fibroblasts. Other exemplary combinations include, without limitation, (a) human hepatocytes (e.g., primary hepatocytes) and fibroblasts (e.g., normal or transformed fibroblasts, including, for example, non-human transformed fibroblasts); (b) hepatocytes and at least one other cell type, particularly liver cells, such as Kupffer cells, Ito cells, endothelial cells, and biliary ductal cells; and (c) stem cells (e.g., liver progenitor cells, oval cells, hematopoietic stem cells, embryonic stem cells, and the like) and a non-parenchymal cell population, for example, stromal cells (e.g., fibroblasts). In some embodiments, combinations of hepatocytes, liver cells, and liver precursor cells may be used. In some embodiments it may be desirable to include immune cells in the constructs, e.g., Kupffer cells, macrophages, B-cells, dendridic cells, etc.

Hepatocytes which may be cultured in the co-culture system as described herein may be from any source known in the art, e.g., primary hepatocytes, progenitor-derived, ES-derived, induced pluripotent stem cells (iPS-derived), etc. Hepatocytes useful with the present invention may be produced by the methods described in Takashi Aoi et al., Science 321 (5889): 699-702; U.S. Pat. Nos. 5,030,105; 4,914,032; 6,017,760; 5,112,757; 6,506,574; 7,186,553; 5,521,076; 5,942,436; 5,580,776; 6,458,589; 5,532,156; 5,869,243; 5,529,920; 6,136,600; 5,665,589; 5,759,765; 6,004,810; U.S. patent application Ser. Nos. 11/663; 11/334, 392; 11/732,797; 10/810,311; and PCT application PCT/JP2006/306783, all of which are incorporated herein by reference in their entirety.

Further cell types which may be cultured in the constructs of the invention include pancreatic cells (alpha, beta, gamma, delta), enterocytes, renal epithelial cells, astrocytes, muscle cells, brain cells, neurons, glia cells, respiratory epithelial cells, lymphocytes, erythrocytes, blood-brain barrier cells, kidney cells, cancer cells, normal or transformed fibroblasts, liver progenitor cells, oval cells, adipocytes, osteoblasts, osteoclasts, myoblasts, beta-pancreatic islets cells, stem cells (e.g., embryonic stem cells, hematopoietic stem cells, mesenchymal stem cells, endothelial stem cells, etc.), cells described in U.S. patent application Ser. No. 10/547,057 paragraphs 0066-0075, which is incorporated herein by reference, myocytes, keratinocytes, and indeed any cell type that adheres to a substrate.

It is understood that constructs of the invention may contain parenchymal cells with one, or two or more types of non-parenchymal cells such as, for example, stromal cells, endothelial cells, stellate cells, cholangiocytes (bile duct cells), Kupffer cells, pit cells, etc. In some embodiments, the parenchymal cells (e.g., hepatocytes) cultured in heterotypic contact with a first population of non-parenchymal cells and a second population of non-parenchymal cells are mixed and distributed around the co-cultured parenchymal cells. In some embodiments, the cell culture may contain at least one non-parenchymal cell population. In certain embodiments, the cell culture may contain more than one non-parenchymal cell population. One of skill in the art will appreciate that particular patterns of non-parenchymal cells surrounding the parenchymal cells may be desired in some cases, e.g., when it is desired to mimic certain in vivo environments. It is understood that any support or accessory cells may be included in the constructs of the invention.

In exemplary embodiments of the invention, supporting or accessory non-parenchymal cells can serve to enhance vascular recruitment to the constructs of the invention. For example, non-parenchymal cells can be selected for encapsulation in the constructs of the invention based on their ability to secrete one or more pro-angiogenic factors. Exemplary pro-angiogenic factors include, but are not limited to vascular endothelial growth factor (VEGF), including isoforms A, B, C, and D, basic fibroblast growth factor (bFGF), interleukin-6 (IL-6), and other inflammatory cytokines, tumor necrosis factor alpha (TNFα), hepatocyte growth factor (HGF) and the like. Non-parenchymal cells can be selected that secret such factors, or can be engineered (e.g., recombinantly engineered) to secrete such factors.

Without being bound in theory, it is also contemplated that one or more soluble factors could be included in a construct of the invention, for example, in drug delivery vehicle (e.g., encapsulated in a drug delivery particle, for example, a time-released delivery particle.)

In certain embodiments, the constructs are engineered to include one or more adherence materials to facilitate maintenance of the desired phenotype of the encapsulated cells. The term "adherence material" is a material incorporated into a construct of the invention to which a cell or microorganism has some affinity, such as a binding agent. The material can be incorporated, for example, into a hydrogel prior to seeding with parenchymal and/or non-parenchymal cells. The material and a cell or microorganism interact through any means including, for example, electrostatic or hydrophobic interactions, covalent binding or ionic attachment. The material may include, but is not limited to, antibodies, proteins, peptides, nucleic acids, peptide aptamers, nucleic acid aptamers, sugars, proteoglycans, or cellular receptors.

The type of adherence material(s) (e.g., ECM materials, sugars, proteoglycans etc.) will be determined, in part, by the cell type or types to be cultured. ECM molecules found in the parenchymal cell's native microenvironment are useful in maintaining the function of both primary cells, and precursor cells and/or cell lines. For example, hepatocytes are known to bind to collagen. Therefore, collagen is well suited to facilitate binding of hepatocytes. The liver has heterogeneous staining for collagen I, collagen III, collagen IV, laminin, and fibronectin. Hepatocytes also display integrins $\beta1$, $\beta2$, $\alpha1$, $\alpha2$, $\alpha5$, and the nonintegrin fibronectin receptor Agp110 in vivo. Cultured rat hepatocytes display integrins $\alpha1$, $\alpha3$, $\alpha5$, $\beta1$, and $\alpha6\mu1$, and their expression is modulated by the culture conditions.

Without being bound in theory, it is believed that optimal construct performance results from a combination of appropriate heterotypic contacts, for example, between parenchymal cells and at least one population of non-parenchymal cells and soluble biochemical cues (e.g., supporting parenchymal cell phenotype and function and, optionally, additionally promoting vaccularization.) Parenchymal cell stabilizing cues and proangiogenic cues can come from the same, or from different populations of non-parenchymal cells. Additional stabilizing cues can include, for example, certain cell-surface molecules, cadherins, receptor ligands, and the like (see, in particular, Khetani et al. 2004, Hepatology 40(3): 545-554, the content of which is hereby incorporated by reference.

II. Methods of Making Constructs—Encapsulation

Tissue engineering techniques combining scaffolds and cells have been previously used to deliver hepatocytes in vivo; however, prior work has focused on the long-term treatment of liver disease and has been challenged by the high metabolic needs of primary hepatocytes. In particular, previous work using biodegradable polymer scaffolds for hepatocyte delivery has focused on acellular scaffolds, which have proven to be limited in assuring homogenous seeding, achieving high engraftment efficiency and maintaining the hepatocyte phenotype (Kaufmann et al. (1997) Cell Transplant 6, 463-468; and Kneser et al. (1999) J. Biomed. Mater Res. 47, 494-503). Indeed, hepatocytes transplanted into rats on such biodegradable polymer matrices were still found to be inferior to liver grafts of equivalent liver mass in compensating for metabolic deficiencies (Uyama et al. (2001) Transplantation 71, 1226-1231). Tissue engineers have also struggled with challenges in vascularizing and oxygenating transplanted hepatic tissues. Researchers have also relied on surgical techniques, namely a combination of portacaval shunt surgery and partial hepatectomy, to supply implanted tissues with portal-supplied nutrients, however, this approach requires several technical surgical steps. Recently, pre-vascularization of therapeutic hepatocyte transplantation sites has been pursued to facilitate transplant integration (Levenberg et al. (2005) Nat. Biotechnol. 23, 879-884; Ohashi et al. (2005) Hepatology 41, 132-140; Stevens et al. (2005) PNAS 102, 11450-11455; Yokoyama et al. (2006) Am. J. Transplant 6, 50-59; and Soto-Gutierrez et al. (2006) Nat. Biotechnol. 24, 1412-1419). Despite moderate success using this strategy for therapeutic liver tissue engineering applications, pre-vascularization protocols add additional surgical steps and time (weeks), and have not been applied to the stabilization of primary human hepatocytes in mice.

The fabrication of 3-dimensional scaffolds that mimic the in vivo cellular microenvironment is of fundamental importance to the success of tissue-engineered constructs. Both scaffold chemistry and architecture can influence the fate of function of engrafted cells. While several methods have been developed to control scaffold architecture, each method has intrinsic limits related to resolution, necessary infrastructure or versatility.

The present invention provides a method for the fabrication of tissue, liver mimetics (constructs) comprising functioning hepatocytes by patterning hepatocellular cultures within 3-dimensional polymeric hydrogel scaffolds. Unlike methods described above requiring surgical steps to provide portal-supplied nutrients, the constructs of the invention are engineered to have sufficient nutrient supply upon encapsulation and for sufficient time prior to vascularization in vivo. The constructs of the invention require, likewise, require no pre-vascularizaion to meet the high metabolic needs of the implanted tissue constructs. These requirements are overcome using the constructs of the invention which comprise pre-populated scaffolds and are engineered to be vasculature-promoting. The degree of vacularization can be determined according to any art-recognized methodology, including counting vessels/area microscopically, measuring vessel volume, e.g., through a plane or section of a construct, etc. (see e.g., FIGS. 3g and 3h and the Working Examples describing same. Degree of vascularization can be established for a certain set of culture and/or construct parameters experimentally and can be presumed to be the same for subsequent cultures/constructs made in the same fashion (i.e., there is no need to explant constructs once an optimized set of culture/encapsulation techniques is determined for a particular model system.) In certain embodiments, constructs take on the order of a few days to vascularize, e.g., 2, 3, 4, or 5 days.

Biopolymers suitable for use with the invention include any polymer that is gellable in situ, i.e., one that does not require chemicals or conditions (e.g., temperature, pH) that are not cytocompatible. Preferably, polymers of the invention are synthetic or natural biopolymers (i.e., are biocompatible.) This includes both stable and biodegradable biopolymers. Biodegradable polymers are useful, for example, where proliferation of one or more populations of the encapsulated cells is desired. Non-biodegradable polymers are useful, for example, when encapsulating cell lines, e.g., immortalized cell lines. In particular, it has been surprisingly found that use of non-biodegradable biomaterials enhances engraftment and inhibits overgrowth of immortalized cell lines, when used in the constructs of the invention. Non-biodegradable materials include, for example, PEGs (e.g., PEG-DA), their derivatives, and other synthetics. Biodegradable materials include, for example, synthetic materials that have degradable or cleavable components, or natural materials (e.g., collagen, alginate, fibrin, etc).

Polymers that can be used in the methods of the invention include, but are not limited to, PEG hydrogels, poly(lactic-co-glycolic acid) (PLGA), hydroxyethyl methacrylate (HEMA), gelatin, fibrin, matrigel, alginate, agarose, polysaccharides, collagen, hyaluronic acid (HA), peptide-based self-assembling gels, thermo-responsive poly(NIPAAm). A number of biopolymers are known to those skilled in the art (Bryant and Anseth, 2001; Mann et al., 2001; and Peppas et al., 2000; all incorporated by reference).

Polymers of the invention are preferably crosslinked, for example, ionically crosslinked. In certain embodiments, the method involves the use of polymers in which polymerization can be promoted photochemically (i.e., photocrosslinked), by exposure to an appropriate wavelength of light (i.e., photopolymerizable) or a polymer which is weakened or rendered soluble by light exposure or other stimulus. Although some of the polymers listed above are not inherently light sensitive (e.g. collagen, HA), they may be made light sensitive by the addition of acrylate or other photosensitive groups.

In certain embodiments, the method utilizes a photoinitiator. A photoinitiator is a molecule that is capable of promoting polymerization of hydrogels upon exposure to an appropriate wavelength of light as defined by the reactive groups on the molecule. In the context of the invention, photoinitiators are cytocompatible. A number of photoinitiators are known that can be used with different wavelengths of light. For example, 2,2-dimethoxy-2-phenyl-acetophenone, HPK 1-hydroxycyclohexyl-phenyl ketone and Irgacure 2959 (hydroxyl-1-[4-(hydroxyethoxy)phenyl]-2-methyl-1propanone) are all activated with UV light (365 nm). Other crosslinking agents activated by wavelengths of light that are cytocompatible (e.g. blue light) can also be used with the method of the invention.

In other embodiments, the method involves the use of polymers bearing non-photochemically polymerizable moieties. In certain embodiments, the non-photochemically polymerizable moieties are Michael acceptors. Non-limiting examples of such Michael acceptor moieties include $\alpha,\beta$-unsaturated ketones, esters, amides, sulfones, sulfoxides, phosphonates. Additional non-limiting examples of Michael acceptors include quinines and vinyl pyridines. In one embodiment, the polymerization of Michael acceptors is promoted by a nucleophile. Suitable nucleophiles include, but are not limited to thiols, amines, alcohols and molecules possessing thiol, amine and alcohol moieties. In certain embodiments, the invention features use of thermally cross-linked polymers.

In still other embodiments, patterned cells of the invention are localized in specified locations that may occur in repeating structures within 3-dimensional biopolymer rather than being randomly localized throughout 3-dimensional slab of biopolymer, on the surface of a regularly or irregularly shaped 3-dimensional scaffold, or patterned on a 2-dimensional support (e.g. on a glass slide). The cells can be patterned by locating the cells within specific regions of relatively homogeneous slabs of biopolymers (resolution up to about 5 microns) or by creating patterned biopolymer scaffolds of defined patterns wherein the living cells are contained within the hydrogel (resolution up to about 100 microns). Patterning is performed without direct, mechanical manipulation or physical contact and without relying on active cellular processes such as adhesion of the cells.

Relatively homogeneous slab of biopolymer refers to a polymerized biopolymer scaffold that is approximately the same thickness throughout and is essentially the same shape of the casting or DEP chamber in which it was polymerized.

Patterned biopolymer scaffold refers to a biopolymer scaffold that is of a substantially different shape than the casting or DEP chamber in which it was polymerized. The pattern could be in the form of shapes (e.g. circles, stars, triangles) or a mesh or other form. In one embodiment, the biopolymer is patterned to mimic in vivo tissue architecture, such as branching structures.

The methods of the present invention can be used for the production of any of a number of patterns in single or multiple layers including geometric shapes or a repeating series of dots with the features in various sizes. Alternatively, multilayer biopolymer gels can be generated using a single mask turned in various orientations. The formation of high resolution patterned cells in 3-dimensions can be achieved by methods other than photopolymerization, such that the limitations of the method are overcome.

Stereolithography via photopatterning may be used to introduce perfusion channels, thus significantly improving diffusive transport of oxygen and nutrients to photoencapsulated hepatocytes. In one embodiment, the perfusion channel consists of a single-layer hexagonal branching pattern. Other methods familiar to the skilled artisan can also be used to improve porosity/perfusion of the constructs of the invention including, but not limited to photopatterning, particle leaching, sacrificial layers, cell-mediated degradation, molding and the like, particularly when fabricating macroporous hydrogels.

Cells may be patterned within the hydrogel by selective polymerization of the biopolymer or by patterning of the cells using an electrical field or both. Theoretically a single cell can be patterned by locating it in a specific position within a biopolymer; however, it is preferred that a plurality of cells, at least 10, preferably at least 20, more preferably at least 100, most preferably at least 500 cells, are patterned. Patterning does not require localization of all cells to a single, discrete location within the biopolymer. Cells can be localized, in lines one or two or many cells wide, or in multiple small clusters throughout a relatively homogeneous biopolymer scaffold (e.g. approximately 20,000 clusters of 10 cells each in a single scaffold). The 3-dimensional patterning can also include patterning of cells or other particles in a single plane by DEP as the cells are contained in a three dimensional scaffold. The cell patterning methods of the invention, can also be used for patterning of organelles, liposomes, beads and other particles.

Cell organization can be controlled by photopatterning of the hydrogel structure. The photopolymerizable nature of acrylate-based PEG hydrogels enables the adaptation of photolithographic techniques to generate patterned hydrogel networks. In this process, patterned masks printed on transparencies act to localize the UV exposure of the prepolymer solution, and thus, dictate the structure of the resultant hydrogel.

In certain embodiments, hepatocellular hydrogel constructs with defined cellular configurations may be prepared by photopatterning PEG hydrogels containing primary hepatocytes and fibroblasts, resulting in a hydrogel network consisting of 3D hepatocyte 'islands' surrounded by regions containing encapsulated fibroblasts. Further control of cell orientation within these patterned domains may be achieved utilizing dielectrophoretic patterning techniques. Dielectrophoresis (DEP) can be used alone for patterning of cells in relatively homogeneous slabs of hydrogel or in conjunction with the photopolymerization method. The methods allow for the formation of three dimensional scaffolds from hundreds of microns to tens of centimeters in length and width, and tens of microns to hundreds of microns in height. A resolution of up to 100 microns in the photopolymerization method and possible single cell resolution (10 micron) in the DEP method is achievable. Photopolymerization apparatus, DEP apparatus, and other methods to produce the 3-dimensional co-cultures of the invention are described in U.S. patent application Ser. No. 11/035,394, which is incorporated herein by reference.

Without being bound in theory, it is believed that the role of the biomaterial facilitates cell survival, persistence at the site, stabilization of mature cells, and the like, as well as providing mechanical support for proliferation and/or regeneration, and a template for vascularization.

In exemplary embodiments, the biopolymers may additionally contain any of a number of growth factors, adhesion molecules, degradation sites or bioactive agents to enhance cell viability or for any of a number of other reasons. Such molecules are well known to those skilled in the art.

In certain embodiments, cells are encapsulated at a concentration or density of about $0.1 \times 10^6$/ml to about $100 \times 10^6$/ml, or about $0.1 \times 10^6$/ml to about $20 \times 10^6$/ml preferably about $0.5 \times 10^6$/ml, 1, 2, 5, 10 or $15 \times 10^6$/ml. In certain embodiments, non-parenchymal cells of a non-parenchymal cell population cell type are encapsulated at a ratio (as compared to parenchymal cells) of about 0.1:1, 0.5:1, 1:1, 1.5:1, 2:1, 3:1, 5:1 or 10:1. In some embodiments, the above values or ranges are at the time of encapsulation. In some embodiments, the above values or ranges are at a time following encapsulation or implantation, e.g., at about 1, 2, 5, 12, 24, 36, 48, 72, 96 or more hours after encapsulation or implantation, i.e., the cells, e.g., the parenchymal cells and/or one or more non-parenchymal cell populations are encapsulated at a lower concentration or density and proliferate to achieve the indicated concentration or density after a certain time in culture or in vivo.

Primary hepatocytes representing the full complement of liver functions and drug metabolism pathways are ideal cells for building implantable human liver mimetics but are challenging to maintain upon isolation. The survival and function of primary hepatocytes within PEG hydrogels is recognized to be highly dependent on microenvironmental factors, including the interactions of hepatocyte-nonparenchymal cell with stromal fibroblasts. In one experiment, co-cultivation of hepatocytes with fibroblasts (HEP/FIB) for one-week followed by encapsulation in PEG-DA at a $8\times10^6$ hep/ml final density (~$0.5\times10^6$ total encapsulated hepatocytes) sustained hepatocyte functions, albumin secretion and urea synthesis, whereas hepatocytes encapsulated at the same density alone (HEP) declined over two to four days of culture.

Human liver-derived non-parenchymal cells have been reported to induce the differentiation of mouse embryonic stem cells to hepatocytes via secreted soluble signals (Soto-Gutierrez, A. et al. Nature Biotechnology 24, (2006) 1412-1419). In one experiment cells from human liver non-parenchymal cell lines were mixed together with HEP/FIB clusters prior to photo-encapsulation, entrapping HEP/FIB clusters near, but not in contact with, the added non-parenchymal cells. Co-encapsulation of the TMNK-1 human liver endothelial cell line (LEC), with HEP/FIB was optimally beneficial to hepatocellular functions, while co-encapsulation of additional FIB was moderately and transiently beneficial, and the human liver TWNT-1 hepatic stellate cell (HSC) line did not improve hepatocyte functions over HEP/FIB only control. It was found that the stabilizing effect of co-embedded LECs was conserved between human and rat HEP/FIB co-cultures but could not be reproduced without initial co-cultivation with FIB, or with conditioned medium from cultured LEC. Collectively, these studies suggest that, while FIB likely provide critical spatiotemporal adhesive cues to help stabilize primary hepatocytes after isolation, co-embedded LEC may further improve encapsulated hepatocyte functions through secretion of short-range or rapidly turned over soluble factors.

PEG hydrogels, due to their resistance to non-specific protein adsorption, are generally non-adhesive and do not support cell attachment. Incorporation of adhesive peptides into hydrogel networks enhances adhesion and modulates function for a wide range of cell types. Specifically, the presence of the RGDS peptide within PEG hydrogel enhances hepatocyte function.

The tunability of PEG scaffold chemistry allows manipulation of cell-matrix interactions of encapsulated human hepatocytes in vitro. NHS ester chemistry may be used to conjugate RGDS, or the negative control RGES peptide, to acrylate PEG monomers. In one experiment, incorporation of said functionalized monomers within the hydrogel network improved encapsulated HEP/FIB synthetic and secretory functions by two- to three-fold compared to RGES controls cultured over one week in vitro. [Other conjugation chemistries are well-know in the art and interchangeable with the NHS chemistries exemplified herein.]

In one aspect, the present invention provides a method of making an implantable human liver tissue construct, comprising obtaining a co-culture comprising a population of human hepatocytes and a population of non-parenchymal cells supporting hepatocellular viability and function; and encapsulating the co-culture in a biocompatible, hydrogel scaffold, derivatized with one or more cell-adhesive peptides, wherein the populations of cells are homogeneously distributed in the hydrogel in a manner permitting contact between the hepatocytes and the non-parenchymal cells.

In one embodiment of the method, the hydrogel is photopolymerized polyethylene glycol (PEG) hydrogel. In another embodiment of the method, the photopolymerized polyethylene glycol (PEG) hydrogel is a polyethylene glycol-diacrylate (PEG-DA) hydrogel. In still another embodiment of the method, the non-parenchymal cells are stromal cells. In a particular embodiment, the stromal cells are fibroblasts. In another embodiment of the method, the hydrogel contains about $8\times10^6$ hepatocytes/ml. In yet another embodiment of the method, the hydrogel contains about $24\times10^6$ fibroblasts/ml (e.g., at the time of encapsulation).

The above methods may further comprise a population of human liver-derived non-parenchymal cells, wherein the population of liver-derived non-parenchymal cells is distributed in the hydrogel in manner preventing contact with the co-cultured hepatocytes:non-parenchymal cells. In one embodiment, the human liver-derived non-parenchymal cells are human liver endothelial cells (LECs). In another embodiment, the hydrogel contains about $6\times10^6$ LECs/ml (e.g., at the time of encapsulation. In yet another embodiment, the LECs are TMNK-1 cells. In certain embodiments of the above methods, the construct has a diameter of about 20 mm and a thickness of about 250 μm, the construct comprising about $0.5\times10^6$ human hepatocytes. In certain embodiments, the constructs are discs having a diameter of about 5-50 mm, preferably about 10-30 mm, for example, about 15, 20 or 25 mm in diameter and a thickness of about 50-1000 μm, 100-500 μm, 200 μm, 250 μm or 300 μm. In certain embodiments, where making a humanized animal, the construct can have a amount of hydrogel of about 2 ml hydrogel/kg animal. In certain embodiments, where making a humanized mouse, the construct can have a volume of about 40 to 75 μl.

The hydrogel may be polymerized homogeneously or through a mask to result in selective photopolymerization and patterning of the biopolymer. In another embodiment, other ways of photopatterning are used including, but not limited to, shining light through an emulsion mask, and also including shining light in a pattern through a digital pattern generator or scanning a laser in a pattern as in stereolithography or using a hologram. In certain embodiments of the above methods, the hydrogel comprises perfusion channels supporting diffusive transport of oxygen and/or nutrients. In other embodiments of the above methods, the scaffold is biodegradable. Photopatterning allows thicker constructs of to be utilized due to increased nutrient and/or oxygen transport to encapsulated cells.

In certain embodiments of the above methods, the cell-adhesive peptide is an extracellular matrix- (ECM-) derived peptide. In one embodiment, the ECM-derived peptide is an RGDS peptide. In one particular embodiment, the RGDS peptide is covalently attached to a component of the hydrogel. In another particular embodiment, the RGDS peptide is covalently attached to an acrylate PEG monomer polymerized in the hydrogel. ECM-derived peptides can be included, for example, at a concentration of about 1-100 μM/ml, for example, at a concentration of about 2-100 μM/ml or about 5-100 μM/ml.

Soluble factors can be included at about 1-1000 ng/ml and, in some embodiments, can be included at up to, for example, 100 μg/ml. Soluble factors can be added or released (e.g., drug delivery means) or can be secreted by supporting cells to achieve the desired concentration, for example, at a specified time after encapsulation or implantation.

In exemplary embodiments, constructs of the invention for use in a mouse have, for example, a size of about 50 to about 1000 μm diameter (micro-spheres, spheres, sphericals and the like), or have a thickness of about 50 to about 1000 μm and a diameter of about 5 to 50 mm (spheres, discs, and the like), or have a thickness of about 50 to about 100 μm and a width and/or depth of about 5 to about 50 mm (squares, rectangles, ovals, etc.). The aforementioned parameters can easily be scaled according to animal size by the skilled artisan. In other exemplary embodiments, construct size is determined according to animal body cavity (e.g., peritoneum, subcutaneous space, intraorgan voids) size, for example, as a % volume or "volumetric density". When considering volume of construct per volume of a given cavity, for example, implant size can range from about 0.001 to about 10%, 20%, 30%, 40%, 50% of body cavity. In exemplary embodiments, implants can be microtissues or larger sized discs, and cavities can be peritoneum or subcutaneous space of any animal species.

In exemplary embodiments, constructs can include about 0.1 to about $5\times10^6$, about 0.2 to about $2\times10^6$, about 0.5 to about $1.5\times10^6$, (e.g., about, $0.5\times10^6$, $0.6\times10^6$, $0.7\times10^6$, $0.8\times10^6$, $0.9\times10^6$, $1.0\times10^6$, $1.1\times10^6$, $1.2\times10^6$, $1.3\times10^6$, $1.4\times10^6$ or $1.5\times10^6$ parenchymal cells/ml. In exemplary embodiments, constructs can include about 1 to about $50\times10^6$, about 2 to about $20\times10^6$, about 5 to about $15\times10^6$, (e.g., about, $5\times10^6$, $6\times10^6$, $7\times10^6$, $8\times10^6$, $9\times10^6$, $10\times10^6$, $11\times10^6$, $12\times10^6$, $13\times10^6$, $14\times10^6$ or $15\times10^6$ parenchymal cells/ml.

Without being bound in theory, it is also contemplated that sufficiently highly functioning parenchymal cells can be encapsulated without nonparenchymal cells, for example, if stabilized or pre-stabilized with appropriate biochemical cues.

In certain embodiments of the above methods, the construct remains viable for at least three, four, six, eight or twelve weeks upon in vivo implantation.

In certain embodiments of the above methods, one or more of the populations of cell are engineered to express a reporter protein.

IV. Humanized Animals Having Engineered Human Tissues

The art describes a growing interest in "humanized" mouse models as tools for the study, treatment and prevention of human disease (Lassnig et al. (2005) Transgenic Res. 14, 803-806; Legrand et al. (2009) Cell Host Microbe 6, 5-9; and Shultz et al. (2007) Nat. Rev. Immunol. 7, 118-130). The instant invention features the following improvements over art-recognized models.

Humanized Animals—Human Liver Models

Current methods for studying human liver functions in vivo are limited to insufficient humanization, or to breeding and surgical complications, lengthy cell engraftment and expansion times, and low repopulation efficiency. In one approach, transgenic mice are genetically engineered to express a single human gene of interest (i.e. a particular CYP3A or 2B isoenzyme, which participates with its isoenzymes in metabolizing approximately 65-80% of clinical drugs; or a human nuclear receptor such as hPXR or SXR, transcription factors which regulate CYPs) (See e.g., Xie and Evans (2002) Drug Discov. Today 7(9): p. 509-15.). However, the utility of these transgenic mice models have been limited to studying drug response profiles and transcriptional regulation of only single drug-metabolizing genes.

More recently, researchers have pursued nearly complete liver humanization in mice using liver-injury mouse models which are permissive to the survival and expansion of injected hepatocytes. The patent literature describes technology for humanizing mice by transplanting cells (i.e. human hepatocytes) into animal models exhibiting severe liver injuries and deficient immune systems. In these mice, the injury is necessary to provide a survival and growth advantage to unstable primary cells. Liver injury can be induced by overexpressing hepatotoxicity genes, such as the urokinase-type plasminogen activator transgene (U.S. Pat. No. 8,199,847, U.S. Pat. No. 7,273,963, U.S. Pat. No. 6,995,299, U.S. Pat. No. 6,864,402; and U.S. Pat. No. 6,509,514), or by tolerizing animals in utero against human or primate hepatocytes (U.S. Pat. No. 7,626,075 and U.S. Pat. No. 7,498,479). Either case requires substantial genetic and surgical skill, and ultimately limits the physiologic relevance of humanized liver mice for research applications in additional disease and immunity settings.

In the scientific literature, Tateno et al. first described the use of liver-injury, immune-deficient mice for human hepatocyte reconstitution in 2004 (Tateno et al. (2004) Am. J. Pathol. 165, 901-912). Human hepatocytes intrasplenically injected into transgenic urokinase-type plasminogen activator overexpressing mice (uPA+/+/SCID) had a selective advantage to 'home' to the damaged host liver, engraft, and repopulate up to 80% of the mouse liver. These mice have been widely characterized since then and had success in modeling select human-type metabolic responses to drugs (Katoh et al. (2005) Xenobiotica 35, 863-875; Katoh and Yokoi (2007) Drug Metab. Rev. 39, 145-157; Okumura et al. (2007) Toxicol. Sci. 97, 533-538; Lootens et al. (2009) Drug Metab. Dispos. 37, 2367-2374; Pozo et al. (2009) Drug Metab. Dispos. 37, 2153-2162; and Lootens et al. (2009) Clin. Chem. 55, 1783-1793), liver-stage development of the human malaria parasite (Morosan et al. (2006) J. Infect. Dis. 193, 996-1004), and hepatitis B and C infection (Ohashi et al. (2000) Nat. Med. 6, 327-331; Tsuge et al. (2005) Hepatology 42, 1046-1054; and Turrini et al. (2006) Transplant Proc. 38, 1181-1184). However, widespread use of the model has been hindered by several limitations: the uPA+/+/SCID mice are notoriously difficult to breed, and they have a very narrow window of time for transplantation before hepatotoxicity becomes lethal (~2 weeks); therefore, timing transplantation with freshly isolated human hepatocytes is logistically prohibitive. Using this model, however in this model only 39-70% of mice were engrafted with human hepatocytes, and of those engrafted only 16-20% were sufficiently repopulated.

Azuma et. al. generated an alternative liver-injury model (Fah–/–/Rag2–/–/Il2rg–/– mice) whereby immune-deficient mice lacking the fumarylacetoacetate hydrolase (Fah) gene develop liver disease upon removal of a protective drug (Azuma et al. (2007) Nat. Biotechnol. 25, 903-910). This mouse model provides a more flexible window of time in which to introduce human hepatocytes and was demonstrated to enable expansion human hepatocytes in vivo over several passages. Yet animals still required pretreatment with a urokinase-expressing adenovirus for human hepatocytes to efficiently engraft and repopulate the mouse liver and only 16.3% of mice injected were highly repopulated with 30-90% human hepatocytes. Despite very recent technical advances improving the repopulation efficiency of the Fah–/– model (Bissig et al. (2007) PNAS 104, 20507-20511; and Bissig et al. (2010) J. Clin. Invest. 120, 924-930), both liver-injury models demand several weeks to several months establishment time, and are inherently variable in their degree of humanization. Thus, a new model which mitigates the need for growth/repopulation stimuli—and which can be generated rapidly and reproducibly among diverse animal backgrounds would significantly advance the utility of humanized mouse models for liver biology applications.

Cell-culture models based on human hepatoma cells[86] and primary human hepatocytes[56] have recently permitted the study of the HCV life cycle in vitro. The hepatitis C virus (HCV) is a blood-borne pathogen afflicting more than 170 million people worldwide and causing serious risk for chronic liver disease, cirrhosis and progression to hepatocellular carcinoma[85]. Current treatments to fight HCV infection are ineffective and difficult to tolerate, and no vaccine for HCV exists. Despite advances in the development of cell culture models for the study of virus (e.g., HCV) infection, the precise mechanisms of HCV infectivity, host cell response, and pathogenesis have yet to be fully elucidated. While researchers continue to study how viral and host properties contribute to HCV entry, replication, persistence and clearance in vitro, in vivo animal models are needed to study viral pathogenesis in a physiologic setting and critical to the development of novel vaccines and therapies[87,88].

Due to the strict human tropism of the hepatitis C virus, and the preference for rodent models over non-human primates for their improved cost, reproducibility and ethical constraints, much effort has been put towards small humanized mouse model development[10,46,89-91]. To date, humanized mice for HCV applications have been generated via transgenic or combined transgenic/transplantation approaches. In the former approach, the conditional expression of proteins from the HCV genome[92,93] or human-specific host entry factors[94] in transgenic mice have enabled limited studies on the cytopathic effects and molecular mechanisms of HCV entry. However, the latter approach of transplanting HCV-infectible human cells into mice has vastly improved the physiologic relevance of small animal models and been useful for the validation of anti-viral therapeutics. An early demonstration of the combined transgenic/transplantation approach used patient-derived HCV-infected liver fragments, or ex vivo infected liver fragments, inserted under the kidney capsule of severely immune-deficient mice. The so-called 'trimera' model exhibited viremia of ~$3\times10^4$ copies/mL, which could be reduced by treating animals with inhibitors of the HCV internal ribosomal entry site (IRES) or monoclonal anti-HCV envelope E2 protein antibodies[95,96]. More recently, human liver chimeric mice transplanted with primary human hepatocytes have advanced the field's ability to study diverse human hepatotrophic infections dynamically in vivo. For example, the urokinase plasminogen activator overexpression (uPA$^{+/+}$/SCID) model was found to be susceptible to infection by *Plasmodium falciparum*[9], hepatitis B virus[18,97-99], and hepatitis C virus[99-102], with the latter responding to anti-HCV therapies IFN 2b, and protease inhibitor BILN-2061[102]. The FAH$^{-/-}$ mouse model has since enabled higher human hepatocyte chimerism and more facile production of humanized mice compared to the uPA$^{+/+}$/SCID model[46]. FAH$^{-/-}$ humanized mice infected with HCV have been reported to exhibit $8.15\times10^8$ copies/mL serum viremia and further shown utility in testing combinations of pegylated-interferon and Debio 025, an HCV inhibitor targeting host cyclophilin A[98].

Despite the promise of small animal mouse models for HCV infection, the current transgenic/transplantation approach is limited as described above, e.g., host mice with liver injury and/or immune-deficiency, the unstable nature of isolated human hepatocytes, cell engraftment inefficiencies, and variability, e.g. in repopulation over time. The humanized animal models of the invention address the challenges in transgenic/transplantation methods in several enabling ways, discussed above. The ability to stabilize the human hepatocyte phenotype prior to implantation, in particular, mitigates the requirement for precisely timed transplantation procedures, and broadens the utility of alternative primary human sources such as the Huh 7.5 human hepatoma cell line, which is highly permissive to HCV in vitro but prone to necrosis as tumors form and overgrow in vivo. The conditions can be further optimized for implanting 3D human hepatoma constructs in mice without liver injury, identifying an accessible ectopic site for implant engraftment and stable in vivo functions (human protein secretion). The working examples demonstrate the utility of 3D human hepatoma constructs for HCV infection in vitro and in vivo. The findings show that mice can be implanted with 3D human hepatoma constructs and that these constructs can be transiently infected with HCV, and that constructs infected prior to implantation can be used for longer term study of HCV pathogenesis in vivo and therapy development. Ultimately, these advances enable the study of HCV infection in the setting of in vivo immunity, or humanized immunity, as well as more rapid and cost-efficient screening of anti-HCV preventative and therapeutic regiments.

Through the studies, described herein, in particular in the working examples presented infra, survival and liver-specific functions of engineered rat or human liver tissues has been demonstrated using a platform that supports liver functions and in vivo. Mice implanted with these tissue constructs are excellent models of human tissue-specific, e.g., liver-specific, function. Thus, mice with human liver constructs can be generated without the cost and labor inefficiencies inherent to performing mouse genetics, inducing liver-injury, awaiting hepatocyte engraftment and repopulation, and assessing degree of humanization. The invention is readily applicable to any routine experimental animal, including but not limited to rodents (rats, mice and the like), canines, primates, in particular, non-human primates (e.g., macaques, chimpanzees, baboons), rabbits, and the like. This invention will aid researchers in both academia and pharmaceutical industries in the study of human liver biology in vivo.

The humanized mice of invention are established via tissue engineering, whereby engineered liver constructs are fabricated by pre-stabilizing primary hepatocytes within biomaterial scaffolds, prior to implantation in mice. In this manner, mice can be readily generated readily for drug metabolism screening purposes and more practically extended to the hands of non-expert researchers. Humanized mice with tissue-engineered livers can also, for the first time, be generated on immune-competent and non-injury backgrounds, including potentially a broad array of relevant disease backgrounds, to allow the study of diseases such as pathogen infection (e.g., HCV, HIV, malaria, and the like), co-diseases such as HCV/HIV, or pathogenesis of infection to carcinoma.

Accordingly, in certain embodiments, provided herein is a method of making a humanized animal comprising human liver tissue, the method comprising implanting the construct any one of the preceding embodiments ectopically in the animal. In one embodiment, the animal is a mouse. In another embodiment, the construct is implanted in intraperitoneal (IP) space. In still another embodiment, the construct in implanted in the subcutaneous space.

V. Uses

The constructs of the invention are useful in a number of different methods as set forth in more detail below.

In the methods of the invention, test drugs may be administered by any desired route, e.g., orally or parenterally. In one embodiment, test drugs are administered interperitoneally.

In one aspect, the methods of the invention are used to investigate how the human liver will metabolize a test drug. For example, a test drug or compound is administered to an animal comprising a construct of the invention and the effect of the test drug on one or more liver enzymes or the products of metabolism of the drug can be tested.

In one embodiment, the effect of the test drug or compound on the level of expression of a liver enzyme is measured using techniques well known in the art. For example, the ability of a test compound to induce an enzyme in the cytochrome P450 mixed function oxidase system (i.e., the effect of the drug on one or more CYPs) can be tested. Exemplary enzymes that are important in drug metabolism include e.g., CYP2A6 and CYP2D6. Other liver human enzymes that can be tested include Phase I detoxification enzymes, Phase II conjugating enzymes, Phase II transporters, transcription factors, and albumin. Examples include: CYP3A4, CYP2C9, CYP3A7, GSTA1, UGT1A9, EPHX1. Levels of CYPs 3A4, 1A2, 2D6, 2E1, and the 2C isoforms can also be tested.

Expression of liver enzymes can be measured, e.g., by standard methods for detecting mRNA expression levels (e.g., using PCR) or protein levels (e.g., Western blot).

In one embodiment, the level of expression of a gene in a humanized animal of the invention can be compared to an appropriate control, e.g., an enzyme level in an animal that has not been treated with the test drug, in an animal that has been treated with a known inducer of liver enzymes, or in an animal that has been treated with the test drug, but which has not been implanted with a construct of the invention. Other suitable controls will be apparent to those of ordinary skill in the art.

In another embodiment, the effect of a test drug or compound on liver enzyme activity is measured using standard methods. For example, catalytic activity of liver enzymes may be measured by quantitating the metabolism of a "probe" drug known to be metabolized by the enzyme of interest. For example, an increase in the conversion of coumarin to 7-hydroxycoumarin (the primary metabolite in humans) signals an induction in CYP2A6. Similarly, an increase in the conversion of debrisoquine to 4-hydroxydebrisoquine indicates an increase in the catalytic activity of CYP2D6. In performing these assays, the ratio of the unmetabolized (or parent) drug and the metabolite can be measured, i.e., the levels of the starting drug and the metabolized drug can be compared.

In another embodiment, the methods of the invention can be used to determine a drug response pathway, i.e., what enzymes are upregulated in response to the test drug and what metabolites are produced in human cells exposed to a test drug.

As will be understood by those of skill in the art, levels of starting drugs and/or metabolites may be measured in any appropriate body tissue or fluid. In one embodiment, plasma levels or urine levels of drugs are measured.

In one embodiment, the level of activity of a human liver enzyme in a humanized animal of the invention can be compared to an appropriate control, e.g., with enzyme activity levels from an animal that has not been treated with the test drug, from an animal that has been treated with a known inducer of liver enzymes, or from an animal that has been treated with the test drug, but which has not been implanted with a construct of the invention. In another embodiment, the ability of a known inhibitor of the activity of the enzyme can be tested in a confirmatory assay. Other suitable controls will be apparent to those of ordinary skill in the art.

In another embodiment, the human metabolites of a test drug can be identified using an animal bearing a construct of the invention. As shown in the instant examples, humanized animals of the invention have been used to identify "major" human metabolites of several drugs. As used herein, the term "major human metabolites" is defined as embracing metabolites having a metabolic ratio of greater than (>) 0.1 (the same definition used by the FDA). When one or more metabolites which are known to be toxic to humans are identified, the assay identifies the test drug as one having potential toxicity in humans. These methods enable the detection of human metabolites prior to clinical testing in man.

In performing the methods of the invention, a test drug may be administered over a set time period, e.g., testing can be done immediately after administration, after a suitable period of time post administration, or after multiple administrations of the test drug. In one embodiment, the effects of a drug on enzyme levels, enzyme activity, or metabolite formation can be assayed after administration and again as time passes, thereby obtaining information regarding the toxicity and/or metabolism of the drug over time.

In another embodiment, the methods of the invention can be performed at varying doses of test drug. Varying the dose can be used to identify preferred dosing regimes for a test drug or doses of a test drug that may be toxic.

In another aspect, the methods of the invention can be used to test interactions between drugs, "drug-drug" interactions. Such interactions may occur when one CYP450-inducing or -inhibiting drug alters the therapeutic or toxic effect of a second drug.

In one embodiment, the interaction between the first drug and the second drug can be measured by administering both drugs (e.g., simultaneously or sequentially) to an animal bearing a construct of the invention. As set forth above, the effect of both drugs can be measured by determining the effect of both drugs (or the effect of the second drug after priming with the first drug) on induction of liver enzymes or on liver enzyme activity. The metabolites formed as the drugs are metabolized can also be measured.

In another embodiment, one drug can be administered to a humanized animal of the invention, and the effect of the second drug can be assayed in vitro on a construct explanted from that same animal. Accordingly, in one embodiment, the invention pertains to a method for assaying drug-drug interaction, comprising administering a first test drug to the humanized animal of the invention, exposing a second test drug the construct following explant from the humanized animal, determining the effect of the second test drug on the expression and/or activity of one or more liver enzymes, wherein a change in the expression and/or activity of the one or more liver enzymes, relative to a suitable control (e.g., an animal exposed to only one drug), identifies the first test drug as potentially interacting with the second test drug.

In yet another aspect, the humanized mice of the invention can be used as a model system to study infection, in particular, infection by human liver-trophic pathogens. As used herein, the phrase "human liver-trophic pathogen" refers to a pathogen (e.g., virus or parasite) that specifically infects human liver. The humanized mice of the invention are particularly suited to the study of human liver-trophic pathogens as they are capable of infecting the liver tissue constructs of the invention but to not, in exemplary embodiments, infect the host mouse liver. Exemplary human liver-trophic pathogens include, but are not limited to, Hepatitis C virus (HCV), HIV, virus serotypes of the genus *Flavivirus*, and malaria parasites such as *Plasmodium falciparum, Plasmodium vivax, Plasmodium ovale*, and *Plasmodium malariae*.

Other Exemplary human liver-trophic pathogens include, but are not limited to HCV of all genotypes, other *flaviviruses*, the primate-infecting plasmodia (*vivax, simium,*

*simiovale, cynomolgi, knowlesi, gonderi, malariae, ovale, falciparum*), and the rodent-infecting pathogens (*berghei, yoelii, chabaudi*).

The constructs and animals of the present invention are suitable for modelling a wide range of viral and non-viral infectious diseases. In preferred embodiments, the infectious diseases are diseases which infect liver cells or exist in the liver during a portion of their infection or life cycle. Information is provided below for several preferred infectious diseases, although this is not to be considered a limiting group. The methods and compositions of the invention may be applied generally to, for example, all hepatitis viruses (e.g., hepatitis C virus (HCV)), virus serotypes of the genus *Flavivirus*, and malaria parasites such as *Plasmodium falciparum, Plasmodium vivax, Plasmodium ovale*, and *Plasmodium malariae*.

Dengue fever is an acute infectious disease caused by dengue virus, and is classified based on its clinical characteristics into classical dengue fever (CDF), which has a good prognosis, dengue hemorrhagic syndrome (DHF), which shows the tendency of hemorrhage, and dengue shock syndrome (DSS), which is the most severe form of the disease and is characterized by shock (Yoshihiro Hirabayashi, "Infectious disease syndrome I Ryoikibetsu Shokogun Shirizu No. 23", 1999, pp. 145-149; Sabin, A. B., American Journal of Tropical Medicine and Hygiene, 1952, Vol. 2, pp. 30-50; Cohen, S. N. et al., Journal of Pediatrics, 1966, Vol. 68, pp. 448-456; Nimmannitya, S. et al., American Journal of Tropical Medicine and Hygiene, 1969, pp. 954-971).

Dengue virus, which is the pathogen of dengue fever, is about 40 to 60 nm in diameter and has an envelope. It has an about 11 kb positive single-stranded RNA, and belongs to the Flaviviridae family together with yellow fever virus, Japanese encephalitis virus and the like in terms of virology. In addition, it is known that dengue virus is classified into 4 serotypes (type 1 to type 4) based on the crossing-over of infection-neutralizing antibodies (Westaway, E. G. et al., Intervirology, 1985, Vol. 24, pp. 183-192; Chambers, T. J. et al., Annual Reviews Microbiology, 1990, Vol. 44, pp. 649-688).

The dengue virus vectors in nature are Aedine mosquitoes. Among them, *Aedes aegypti* mosquitoes which widely inhabit tropical areas become major carrying mosquitoes (Bancroft, T. L. Australasian Medical Gazette, 1906, Vol. 25, pp. 17-18).

Malaria is caused primarily by infection of one of four species of protozoa of the genus *Plasmodium*. The four species include: *Plasmodium vivax, Plasmodium malariae, Plasmodium falciparum* and *Plasmodium ovale*. Of these, *Plasmodium falciparum* produces the most pathogenic of the malarias and often results in death.

In malaria, the disease is such that infection followed by recovery does not confer meaningful protection to the individual despite a significant antibody response to several of the parasite proteins.

In the life cycle of the malaria parasite, a human becomes infected with malaria from the bite of a female *Anopheles* mosquito. The mosquito inserts its probe into a host and in so doing, injects a sporozoite form of *Plasmodium falciparum*, present in the saliva of the mosquito. The sporozoites which have been injected into the human host are cleared into a number of host tissue cells, including liver parenchyma cells (hepatocytes) and macrophages. This phase is known as the exoerythrocytic cycle because at this point in the life cycle the organism has not yet entered red blood cells. After entering hepatocytes, sporozoites undergo a transformation into trophozoites, which incubate and undergo schizogony, rupture and liberate tissue merozoites. This process takes approximately 7-10 days and, depending upon species, may repeat itself several times, during which time the host feels no effects. In *Plasmodium falciparum*, this repetition does not occur. After the incubation period, the liver or other tissue cells burst open (or bleb out) to release numerous merozoites into the bloodstream.

Shortly thereafter, certain of these blood borne merozoites invade red blood cells, where they enter the erythrocytic phase of the life cycle. Within the red blood cells, young plasmodia have a red nucleus and a ring-shaped, blue cytoplasm. The *plasmodium* divides into merozoites, which may break out of the red blood cell, enter other erythrocytes and repeat the multiplication process. This period lasts approximately 48 hours.

During this same 48 hour period of the erythrocytic cycle, male and female gametocytes are formed in the red blood cells. These gametocytes also burst out of the red blood cells along with the merozoites. It is during this period that the human host experiences the symptoms associated with malaria. The merozoites which burst forth from the red blood cells live for only a few hours in the bloodstream. The gametocytes live for several days or more in the host's bloodstream.

The gametocytes are capable of mating only in the mosquito. Thus, in order for *Plasmodium falciparium* to produce sporozoites for infecting a second human host, a mosquito must first bite a human host carrying gametocytes. These gametocytes mature into macrogametes, mate in the mosquito's stomach and produce a zygote. The zygote (ookinete) is active and moves through the stomach or the midgut wall. Under the lining of the gut, the ookinete becomes rounded and forms a cyst called an oocyst, in which hundreds of sporozoites develop. Sporozoites thereafter invade the entire mosquito and many of them enter the salivary glands where they are in a favorable position to infect the next host when the mosquito feeds on its blood. The life cycle thereafter simply repeats itself in another human host.

HCV is an enveloped positive strand RNA virus in the Flaviviridae family. The single strand HCV RNA genome is approximately 9600 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature nonstructural proteins (NS2, NS3, NS4A, NS4B, NS5A, and NS5B) is effected by two viral proteases. The first one, cleaves at the NS2/NS3 junction (henceforth referred to as NS2-3 protease); the second one is a serine protease contained within the N-terminal region of NS3 (NS3 protease) and mediates all the subsequent cleavages downstream of NS3, both in cis, at the NS3/NS4A cleavage site, and in trans, for the remaining NS4A/NS4B, NS4B/NS5A, NS5A/NS5B sites. The NS4A protein appears to serve multiple functions, acting as a cofactor for the NS3 protease and possibly assisting in the membrane localization of NS3 and other viral replicase components. The complex formation of the NS3 protease with NS4A seems necessary to the processing events, enhancing the proteolytic efficiency at all of the sites. The NS3 protein also exhibits nucleoside triphosphatase and RNA helicase activities. NS5B is a RNA-dependent RNA polymerase that is involved in the replication of HCV. For a review of HCV, see Houghton, "Chapter 32, Hepatitis C Viruses," in: Fields Virology, 3rd ed., Fields et al. eds., pp 1035-1058, 1996, Lippincott-Raven Publishers, Philadelphia, Pa.; Moradpour et al. Nat Rev Microbiol. 2007 5(6):453-63; and Knipe et al. Field's Virology. 5th Edition. 2007. ISBN-10:0781760607, ISBN-13: 9780781760607 which are all incorporated herein by reference.

The HCV virus must infect liver cells in order to carry out its life cycle. After attachment of the viral envelope to receptors on cell membrane, the envelope fuses to the cellular membrane, thereby releasing the viral protein core into the target cell cytosol. After dissolution or breaking open of the protein coat, the viral RNA is released and employs the cell's ribosomes to create viral proteins. The NS proteins first direct synthesis of an antisense copy of the viral RNA, which serves as a template for the production of nascent plus sense viral RNA. Structural proteins and nascent plus sense viral RNA, in cooperation with certain NS proteins, assemble into progeny viralvirus particles. These particles proceed membrane through the secretory pathway where they are eventually released out of the cell.

In exemplary embodiments, constructs of the invention are infected with human liver-trophic pathogen prior to ectopic implantation in the host animal, e.g., mouse. In other embodiments, constructs of the invention are infected with human liver-trophic pathogen after ectopic implantation in the host animal, e.g., mouse. In yet other embodiments, constructs of the invention are infected with human liver-trophic pathogen both before and after ectopic implantation in the host animal, e.g., mouse. Exemplary constructs feature parenchymal cells, optionally supported by suitable non-parenchymal cells. Exemplary parenchymal cells include primary hepatocytes and hepatocyte cell lines (e.g., hapatoma cell lines.) Exemplary non-parenchymal cells include fibroblast cells, as well as other liver-associated non-parenchymal cells, as described in detail herein.

Constructs infected with human liver-trophic pathogens, and humanized animals, e.g., mice, implanted ectopically with same, are well suited for assays (e.g., screening assays) for potential anti-pathogen (e.g., anti-viral or anti-parasitic) drugs. Characterization of lead compounds in drug development (e.g., anti-viral drug development or anti-parasitic drug development) can be further achieved using the constructs and model animals of the invention.

In exemplary embodiments, the constructs and/or systems of the invention may be used to screen a wide variety of compounds, such as small molecules, antibodies, peptides, nucleic acid-based agents and the like, to identify agents that modify or inhibit viral or parasitic infection, replication, etc. In a exemplary embodiment these results may be assessed by observation of reporter gene fluorescence in a cell or in the media (e.g., when a reporter gene is released into the cytosol from the mitochondria upon viral infection.) This may be observed as fluorescence in the cell or cytosol by microscopy or automated optical readout).

VII. Commercial Application

Commercial interest in human hepatocyte culture has grown tremendously in recent years, in part owing to an increasing appreciation of species-specific differences among liver functions in humans and laboratory research animals. To better predict human liver toxicity and to reduce the number of post-market drug withdrawals and failures in clinical trials, pharmaceutical companies are turning to human hepatocyte culture for high-throughput screening early in the drug development pipeline.

Nevertheless, in vitro human liver tissues cannot be used to study dosing regimes, routes of administration, multi-organ toxicity, or dynamic responses to drugs over time. The recent emergence and continued development of humanized liver mice in the literature have highlighted a growing interest in new in vivo models of human liver. In vivo models of the human liver are meant to address a critical gap in the study of drug pharmacokinetics and treatment of human liver pathologies, and to complement existing pharmacological screens. However, current chimeric mouse model technology has not yet been implemented in commercial settings, nor have they been amenable to widespread applications, because they require enormous technical skill and are too time-consuming and costly to generate (~6 weeks, ~$1 k/mouse).

This invention provides for rapid and robust generation of humanized liver models by using stabilizing biomaterial scaffold devices to integrate human hepatocytes in vivo (~2 weeks, ~$100/mouse). Thus, an immediate commercial application of this technology is to validate drug safety, efficacy and dosing details using humanized mice prior to Phase I clinical trials, in which early patient exposure has the potential to be dangerous as well as costly. An added commercial benefit of this invention for drug toxicity screening is the ability to perform higher throughput and multiplexed testing on engineered tissues derived from multiple patients. Accordingly, this technology allows researchers to efficiently study in mice the interindividual variability that causes variable drug pharmacokinetics, efficacy and toxicity among patients. While current chimeric mouse models are touted for this purpose, this technology of the instant invention can minimize reagents and animals, sample processing, and overall labor, to greatly enhance economic gains within the drug development pipeline.

Humanized liver mouse models are also useful for the study and treatment of human liver pathologies, including such widespread diseases as hepatitis and malaria. By allowing viral life cycles and pathogenesis to develop in a humanized, systemic setting, this invention may lead to the identification and development of novel therapeutic compounds along with specific treatment regimes. Finally, tissue-engineered in vivo toxicology and pathology liver models can also be used to better predict human responses to environmental toxins, or chemical and biowarfare agents, as they provide a mechanism to control physiologic dosing and administration routes, as well as to observe the systemic, multi-organ effects of exposed toxins.

The foregoing disclosure teaches to those of skill in the art the aspects of the invention including how to make and use the invention. This invention is further illustrated by the following examples which should not be construed as limiting. The contents of all references, patents and published applications cited throughout this application, are incorporated herein by reference.

EXAMPLES

In the past, primary hepatocytes have proven particularly challenging to maintain and implant via biomaterials due to their unstable phenotype, variable engraftment efficiencies and high metabolic needs. Microfabrication tools have been developed and adapted to encapsulate cells in tunable, photopolymerizable polymer hydrogels (polyethylene glycol-diacrylate, PEG-DA) and critical chemical and biological factors for maintaining encapsulated primary rat hepatocyte functions in vitro have been identified. The instant invention demonstrates the development of a human liver 'mimetic,' explores its implantation in various laboratory mouse models, and provides an in vivo human drug metabolism model with broad capabilities.

Example 1

Materials and Methods

Fabrication and Culture of Implantable Liver Mimetics.

Liver mimetics were fabricated using a hydrogel polymerization apparatus. In brief, cellular pre-polymer solution was loaded into a 20-mm diameter, 250 mm-thick silicone spacer, and the solution exposed to UV light from a spot curing system with collimating lens (320-390 nm, 10 mW/cm$^2$, 20-30 s; EXFO Lite). Pre-polymer solution comprised of polyethylene glycol diacrylate (PEGDA 20 kDa at 10% w/v; Laysan Bio, Inc.), 0.1% w/v Irgacure 2959 photoinitiator, and 15 mmol/ml acrylate-PEG-peptide monomers. Acrylate-PEG-peptide monomers were synthesized by conjugating RGDS or RGES to acrylate-PEG-N-hydroxysuccinimide (3.4 kDa) at a 1:1 molar ratio in 50 mM sodium bicarbonate buffer (pH 8.5). Reactions were dialyzed overnight against 1000 kDa MWCO cellulose ester membrane and lyophilized for long-term storage at −80° C. Hepatocyte/fibroblast co-cultures were encapsulated at a final concentration of 8×10$^6$ hepatocytes/ml pre-polymer, in the absence or presence of an additional 6×10$^6$ liver endothelial cells (LEC)/ml of pre-polymer.

Implantation and Assessment of Liver Mimetics.

NCR nude/nude mice were anesthetized using 2.5% Isoflurane with 100% oxygen flow at 1.0 liter/min, pre-injected with analgesic buprenorphine (0.1 mg/kg), and skin prepped using Betadine/isopropanol. Implants were placed in the subcutaneous or peritoneal cavity following a 1 cm incision made in the skin, abdominal wall and/or peritoneum. The abdominal wall was closed with silk sutures and the skin closed with sutures or staples. Mice were monitored for return to normal activity. For non-invasive functional monitoring of implanted liver mimetics, hepatocyte/fibroblast co-cultures were transduced with a packaged lentivirus expressing firefly luciferase under the human albumin promoter (TRIP-ALB-Fluc, 1:5 dilution), in a solution with 4 mg/ml polybrene, 20 mM HEPES and hepatocyte medium, prior to encapsulation and implantation. Mice administered 250 ml of 15 mg/ml D-Luciferin/PBS solution by i.p. injection were imaged using the IVIS Spectrum system and Living Image software. Blood obtained via retro-orbital blood draw, and serum was separated by centrifugation at 1200 g for 10 minutes and serum stored at −20° C. for biochemical or pharmacological analyses. Animals were sacrificed for necropsy and implant retrieval by $CO_2$ euthanization or cardiac puncture with cervical dislocation.

Vascular Perfusion and Micro-CT Imaging.

Mice under isoflurane anesthesia were treated with intracardiac perfusions of 10 U/ml of heparin, 4 mg/L papaverin and 1 g/L adenosine vasodilation agents, 2% (v/v) PFA in PBS fixative solution, and Microfil silicon contrast reagent (yellow) prepared according to manufacturer's instructions. MicroCT scans of whole mice or extracted liver mimetics were obtained using the explore Locus MicroCT platform. Scan parameters were 0.021 mm voxel size, 400 views, 2000 ms exposure time, 80 kV photon energy, and 450 mA current. Scans were analyzed using GE Microview and Osirix rending software programs.

Biochemical Assays.

Human albumin in serum or media samples was quantified by enzyme-linked immunosorbant assay performed using goat anti-human albumin antibody, horseradish peroxidase detection, and 3,3',5,5'-tetramethylbenzidine development. Urea was measured by acid- and heat-catalyzed detection of diacetylmonoxime conversion to a colorimetric product. Alanine aminotransfer (ALT) and aspartate aminotransfer (AST) enzymatic levels were detected with clinical kits based on colorimetric endpoint methods.

Cytochrome-P450 Studies.

All chemicals were purchased from Sigma. For induction studies, in vitro liver mimetics were treated daily for 3 d with CYP450 inducers 20 mM rifampin (RIF) or 50 mM omeprazole (OME) in media (stocks <0.1% DMSO). Mice were injected i.p. daily for 3 d with 25 mg/kg RIF/saline solution, or gavaged p.o. daily for 3 d with 10 mg/kg OME/water solution. For inhibition studies, 1 h prior to substrate incubation, CYP450 inhibitors 8' methoxypsoralen (8 MP, 0.1 mM), or quinidine (quin, 0.5 mM) were incubated with liver mimetics at various concentrations. Mimetics were then incubated with CYP450 substrates: 7-benzyloxy-4-trifluoromethylcoumarin (BFC, 50 mM), ethoxyresorufin (ER, 5 mM) with 10 mM dicumarol, testosterone (TEST, 200 mM), coumarin (100 mM) or debrisoquine (DB, 100 mM), for 2 h at 37° C. with 5% $CO_2$. Reactions were stopped by collection of mimetic supernatants. Glucuronidase/sulfatase-mediated Phase II metabolites from coumarin or debrisoquine reactions were hydrolyzed by incubating supernatant with b-glucuronidase/arylsulfatase for 2 h at 37° C. The metabolites of BFC (7-hydroxy-4-trifluoromethylcoumarin, 7-HFC), ER (ethoxyresorufin-O-dealkylation), and coumarin (7-hydroxycoumarin, 7-HC) were quantified using a fluorescence microplate reader and standard curve at the following wavelengths: 410/510, 530/590, 355/560 ex/emm, respectively. Substrates and metabolites of TEST (6b-hydroxytestosterone, 6b-HTS), coumarin (7-hydroxycoumarin, 7-HC), and debrisoquine (4-hydroxydebrisoquine, 4-HDB) in supernatant or serum were quantified using liquid chromatography/mass spectrometry. BFC is metabolized by multiple CYP450 isoforms, ER is metabolized by CYP1A2 to ethoxyresorufin-O-dealkylation, TEST is metabolized by human CYP3A4 to 6b-HTS, coumarin is metabolized by human CYP2A6 to 7-HC, and DB is metabolized by human CYP2D6 to 4-OHDB.

Pharmacokinetic Analysis.

Mice administered 80 mg/kg of coumarin injected i.p. or 2 mg/kg debrisoquine (DB) gavaged p.o were subjected to retro-orbital draw at 5, 10 15, 30, 60, 90, and 120 minutes after drug administration, and terminal urine collection at 4 h. From ~100 ml blood collections, serum was separated by centrifugation at 1200 g for 10 minutes and stored at −20° C. Glucuronidase/sulfatase-mediated Phase II metabolites in serum or urine were hydrolyzed by incubating samples with b-glucuronidase/arylsulfatase for 2 h at 37° C. Metabolites of coumarin (7-hydroxycoumarin, 7-HC), and debrisoquine (4-hydroxydebrisoquine, 4-OHDB) were quantified using liquid chromatography/mass spectrometry. The area under the curve from time 0 until the time of the last measurable plasma concentration ($AUC_{0-t}$) was calculated using the linear trapezoidal. Peak concentration ($C_{max}$) and time to reach maximum concentration ($t_{max}$) values were obtained directly from the plasma concentration-time profile. Metabolic ratios were determined by dividing the $AUC_{0-t}$ of metabolite by the $AUC_{0-t}$ of the parent drug.

Statistical Analysis.

Experiments were independently repeated 2-3 times with replicate samples as indicated in figure captions. Statistical analysis was performed using one-way ANOVA and Tukey's post-hoc test for group comparisons. Errors bars represent standard error of mean (SEM).

Cell Culture.

All cells were cultured in a 5% $CO_2$ humidified incubator at 37° C. both before and after encapsulation. Fresh primary human hepatocyte suspensions were obtained from a 48-year-old, non-obese Caucasian male with no history of smoking, alcohol or drug abuse. Cryopreserved primary human hepatocytes were obtained from CellzDirect (Lot Hu4151, donor: 50 year-old female) or Celsis technologies (Lot # GHA, donor: 1 year-old female). Primary rat hepatocytes were harvested from 2-3 month old adult female Lew rats. Human hepatocyte medium comprised of high glucose DMEM with 10% (v/v) fetal bovine serum, 1% (v/v) ITS (BD Biosciences), 0.49 pg/ml glucagon, 0.08 ng/ml dexamethasone, 0.018 M HEPES, and 1% (v/v) penicillin-streptomycin. Rat hepatocyte medium contained high glucose DMEM, 10% fetal bovine serum (FBS), 0.5 U/mL insulin, 7 ng/mL glucagons, 7.5 mg/mL hydrocortisone, 10 U/mL penicillin, and 10 mg/mL streptomycin.

J2-3T3 fibroblasts were cultured at <18 passages in Dulbecco's Modified Eagle's Medium (DMEM) with high glucose, 10% (v/v) bovine serum, and 1% (v/v) penicillin-streptomycin. To prepare hepatocyte/fibroblast co-cultures, hepatocytes were seeded at a density of $1.0 \times 10^6$ cells/well in a six-well plate adsorbed with 0.14 mg/mL Collagen-1 extracted from rat-tail tendons. Fibroblasts were added at $0.4 \times 10^6$ cells/well 24 hours after hepatocyte seeding. Media was changed daily on the cultures for 7-10 days prior to hydrogel encapsulation or in vivo injection.

The liver endothelial cell line abbreviated here as 'LEC' and hepatic stellate cell line referred to here as 'HSC' are respectively TMNK-1 and TWNT-1 lines. Both lines were cultured at <18 passages in DMEM with high glucose, 10% (v/v) fetal bovine serum (FBS), and 1% (v/v) penicillin-streptomycin.

Conditioned Media Experiments.

LEC encapsulated at a density of $6 \times 10^6$ cells/ml pre-polymer solution or the same number of cells seeded into a 12-well plate were cultured in 0.5 ml rat hepatocyte medium. Spent conditioned media from 2D monolayer LEC or 3D encapsulated were used to feed rat hepatocyte HEP/FIB liver mimetics in 12-well plates daily, starting 1 day after mimetic fabrication. Supernatants were collected every 48 h and stored at −20° C. for hepatocellular assays.

Drug-Drug Interaction and Toxicity Studies.

Humanized mice at day 6 of implantation were induced for 3 d by daily i.p. injection of RIF (25 mg/kg) or DMSO vehicle control. At day 9 of implantation, mice were fed by oral gavage with 500 ml drinking water or 500 ml acetaminophen (APAP, 250 mg/kg) in water. Mice were fasted for 16 h prior to APAP administration. Following APAP exposure, blood was collected by retro-orbital draw at 4 h. Blood samples were acquired by retro-orbital draw at 4 h following APAP exposure, serum separated, and serum analyzed for enzymatic activity of alanine transaminase (ALT) and aspartame transaminase (AST), non-species specific markers of liver damage (Teco Diagnostics). Engineered liver mimetics and mouse livers were extracted for biochemical and histological analysis. Mouse livers were paraffin-embedded, sectioned with 5 um slices, de-paraffinized and stained for hematoxylin and eosin (H&E).

RNA Isolation and Luminex PCR Analysis.

Total RNA was isolated and purified from 2D and 3D hepatocyte cultures on day 10 after isolation using Trizol and Mini-RNeasy kit, both according to the manufacturer's instructions. Luminex PCR procedures and probes for profiling 83 human-specific drug metabolism enzymes were used. Briefly, total RNA (250 ng) diluted in TCL buffer (20 ml total) was immobilized on a Qiagen turbo capture 384-well plate and reverse-transcribed using olido-DT priming. A solution containing FlexMAP tag upstream probe, phosphorylated downstream probe and ligation buffer were added and reacted at 95° C. for 2 min denaturation, 50° C. for 60 min annealing, 4° C. for 1 min cooling. Taq ligase was then added and incubated at 45° C. for 60 min ligation. Universal PCR was performed for 35 cycles using a biotinylated T7 forward primer and T3 reverse primer in buffer with dNTPs and Taq polymerase. Finally, FlexMAP beads were added and allowed to hybridize in buffer at 45° C. for 60 min after a 2 min 95° C. denaturation step. Streptavidin-phyoerythrin was reacted at 45° C. for 5 min to capture amplicons, and 100 events per bead were analyzed for internal bead color and phyoerythrin reporter fluorescence on a Luminex 100 analyzer. Data for replicate loadings, expressed in Mean Fluorescent Intensity (MFI) of at least 100 beads for each sample, were averaged, scaled to the control human transferrin gene, and log 2 normalized for heat map representation using Gene Pattern open software.

Microscopy.

Fluorescent images were acquired using a Nikon Ellipse TE200 inverted fluorescence microscope and CoolSnap-HQ Digital CCD Camera, with MetaMorph Image Analysis software package for acquiring digital micrographs. Histology images were acquired using a Zeiss Axiophot II upright microscope with color camera and OpenLab/Volocity software.

Encapsulation of Hepatoma Cells.

Huh 7.5 hepatoma cells were cultured at <30 passages in Huh 7.5 medium containing high glucose DMEM, 10% fetal bovine serum, and 1% penicillin-streptomycin in a 37° C., 5% $CO^2$ incubator. 3T3-J2 fibroblasts were cultured at <16 passages in fibroblast medium comprised of high glucose DMEM, 10% bovine serum, and 1% penicillin-streptomycin in a 37° C., 5% $CO^2$ incubator. To create co-cultures, Huh 7.5 were seeded in Huh 7.5 medium at a density of $4 \times 10^5$ cells per well, in 34-mm tissue-culture wells. Twenty-four hours later, fibroblasts were seeded at $4 \times 10^5$ cells per well in fibroblast medium. Medium was replaced daily with Huh 7.5 medium for 4 days prior to harvest by trypsinization and 3D construct encapsulation. Huh 7.5 or Huh 7.5/J2 constructs were made by photoencapsulating $8 \times 10^6$ cells/ml in pre-polymer solution of polyethylene glycol diacrylate (PEGDA, 20 kDa, 10% w/v; Laysan Bio, Inc) and 0.1% w/v Irgacure 2959 photoinitiator (Ciba), using a hydrogel polymerization apparatus previously described[42] and a spot curing system with collimating lens (320-390 nm, 10 mW/cm$^2$, 20-30 s; EXFO Lite). Construct size was defined by the diameter and thickness of the silicone spacer used for cell/pre-polymer solution loading (10-mm diameter, 250 μm-thick). To create constructs containing covalently linked RGDS peptide, pre-polymer solution containing 10 μmol/ml acrylate-PEG-peptide monomers was used to encapsulate cells. Acrylate-PEG-RGDS monomers were synthesized by conjugating RGDS (American Peptide, Sunnyvale, Calif.) to acrylate-PEG-N-hydroxysuccinimide (3.4 kDa, JenKem) at a 1:1 molar ratio in 50 mM sodium bicarbonate buffer (pH 8.5). Reactions were dialyzed overnight against 1000 kDa MWCO cellulose ester membrane and lyophilized for long-term storage at −80° C. Constructs were cultured in Huh 7.5 medium in a 37° C., 5% $CO^2$ incubator, and medium was changed daily.

Assessment of Hepatoma Cell Construct Viability and Function.

Encapsulated cell viability was examined by labeling constructs with calcein AM (5 μg/ml) and ethidium homodimer (2.5 µg/ml) (live/dead) fluorescent stains (Molecular Probes). Images were acquired using a Nikon Ellipse TE200 inverted fluorescence microscope and CoolSnap-HQ Digital CCD Camera. Human albumin in media supernatant or serum was quantified by enzyme-linked immunosorbant assay performed using goat anti-human albumin antibody (Bethyl Labs), horseradish peroxidase (Bethyl) detection, and 3,3',5,5'-tetramethylbenzidine (TMB, Pierce) development.

HCV Reporter Viruses and Hepatoma Cell Construct Infection.

Viruses included a gaussia-luciferase expressing HCV reporter virus (HCV-Gluc), a fully-infectious HCVcc (HCV cell-culture) reporter virus encoding secreted Gaussia luciferase, HCVcc encoding RFP and HCVcc encoding firefly luciferase. Infections were performed by exposing constructs to MOI 0.125 virus, incubating at 37° C. for 8 h, and washing several times after exposure.

To quantify HCV RNA copies in infected 3D constructs, 3-4 constructs of each condition were pestle homogenized in Trizol (Invitrogen). Total RNA was isolated and used in a sensitive Eragen Q-PCR kit for HCV RNA amplification according to manufacturer's instructions.

Example 2

Implantable Human Liver Mimetics

A tissue engineering approach to establish a novel humanized liver mouse model which can be generated rapidly and reproducibly among mice with diverse backgrounds, and which is broadly enabling for research and drug development was used in this study. (FIG. 1a) This approach leverages a micro-engineered hydrogel scaffold capable of functionally stabilizing primary hepatocytes ex vivo, delivering hepatocytes to accessible ectopic sites in vivo, and integrating with host mouse circulation (FIGS. 1b and 1c).

Primary hepatocytes representing the full complement of liver functions and drug metabolism pathways are ideal cells for building implantable human liver mimetics but are challenging to maintain upon isolation. To engineer an implantable microenvironment for stabilizing primary human hepatocytes ex vivo, the effects of hepatocyte-non-parenchymal cell interactions with stromal fibroblasts in 2D and 3D culture models were analyzed. Co-cultivation of hepatocytes with J2-3T3 fibroblasts (HEP/FIB) for one-week followed by encapsulation in PEG-DA at a $8 \times 10^6$ hep/ml final density (~$0.5 \times 10^6$ total encapsulated hepatocytes) led to sustained hepatocyte functions such as albumin secretion and urea synthesis, whereas hepatocytes encapsulated at the same density alone (HEP) declined over two to four days of culture. Subsequently, the tunability of PEG scaffold chemistry was utilized to explore the importance of cell-matrix interactions on encapsulated human hepatocytes in vitro. Covalent NHS ester chemistry was used to conjugate RGDS, or the negative control RGES peptide, to acrylate PEG monomers, and incorporated functionalized monomers within the hydrogel network (FIG. 1d). RGDS improved encapsulated HEP/FIB synthetic and secretory functions by two- to three-fold compared to RGES controls cultured over one week in vitro (FIGS. 1e and 1f). These data, taken with studies from our group, which profiled the integrin expression of primary hepatocytes in vitro (Liu Tsang V, et al. (2007) Fabrication of 3D hepatic tissues by additive photopatterning of cellular hydrogels. *FASEB J* 21(3):790-801) suggest a dependence on juxtacrine cell interactions in 3D and responsiveness to the RGDS ligand via the hepatocyte cell surface integrin, $\alpha_5\beta_1$.

In previous findings, rat hepatocytes were similarly dependent on heterotypic cell-cell interactions and responsive to RGDS via the cell-surface $\alpha_5\beta_1$ receptor. However, optimal human HEP/FIB encapsulation densities were distinct from optimal rat hepatocyte encapsulation densities ($4 \times 10^6$ hep/ml), suggesting a lower metabolic requirement or higher dependence on homotypic interactions for human hepatocytes in 3D PEG hydrogels. Notably, the instant invention demonstrates that tuning hydrogels with optimal human hepatocyte stabilizing factors, resulted in levels of functional marker and viability staining that were comparable between encapsulated fresh and encapsulated cryopreserved human hepatocyte/fibroblast cultures (FIGS. 1g and 1h). Due to their availability and potential for improved reproducibility, further human liver tissues were built from one of two sources of cryopreserved primary hepatocyte donors.

Human liver-derived non-parenchymal cells have been reported to induce the differentiation of mouse embryonic stem cells to hepatocytes via secreted soluble signals. To investigate the effects of soluble stimuli (paracrine signaling) on 3D encapsulated human hepatocytes in vitro, cells from human liver non-parenchymal cell lines were mixed together with HEP/FIB clusters prior to photo-encapsulation, entrapping HEP/FIB clusters near, but not in contact with, the added non-parenchymal cells (FIG. 1i). Co-encapsulation of the TMNK-1 human liver endothelial cell line (LEC) with HEP/FIB was optimally beneficial to hepatocellular functions (FIGS. 1j and 1k), while co-encapsulation of additional FIB was moderately and transiently beneficial, and the human liver TWNT-1 hepatic stellate cell (HSC) line did not improve hepatocyte functions over HEP/FIB only control (FIGS. 1l and 1m). Exploring the mechanism of this tri-culture effect in a rat hepatocyte model, it was found that the stabilizing effect of co-embedded LECs was conserved between human and rat HEP/FIB co-cultures but could not be reproduced without initial co-cultivation with FIB, or with conditioned medium from cultured LEC (FIGS. 1n, 1o and 1p). Thus, while FIB likely provide critical spatiotemporal adhesive cues to help stabilize primary hepatocytes after isolation, co-embedded LEC further improves encapsulated hepatocyte functions through secretion of short-range or rapidly turned over soluble factors. Ultimately, the optimization of cellular and chemical micro-niche properties (juxtacrine and paracrine signaling) (3D HEP/FIB+LEC) resulted in greater than 3 week human hepatocyte stability in vitro.

Example 3

Characterization of Human Liver Mimetics

In order to assess the utility of tissue-engineered hepatocyte cultures for drug metabolism studies, we characterized human liver mimetics, or HEALs, for the expression and function of human drug-metabolizing enzymes, comparing 3D-encapsulated HEP/FIB HEALs to same-donor 2D HEP/FIB cultures on day 10 of culture. The 2D condition acts as reference for a stable hepatocyte coculture model, previously shown to express a number of genes pertinent to ADME/Tox in vitro. However, to date, assessment of hepatocyte models has hinged on the measurement of only a small handful of drug-metabolizing enzymes. Noting that drug-metabolizing enzymes are regulated primarily at the level of transcription, we hypothesized that we could comprehensively assess drug-metabolizing enzyme expression levels in a low-cost, high-throughput assay based on the multiplexed ligation mediated amplification (LMA) of transcripts coupled to detection on Luminex beads. Accordingly, we designed probes for 83 human drug metabolism-encoding transcripts including phase I detoxification enzymes, phase II conjugating enzymes, phase III transporters, several key transcription factors, and albumin (FIG. 2A and FIG. 2G, and Table 1.)

TABLE 1

HUMAN HEPATIC DME GENE SET/LUA-VERSION 4.0

| | |
|---|---|
| CYP2A6 | Cytochrome P450 2A6 |
| CYP2B6 | Cytochrome P450 2B6 |
| CES2 | Carboxylesterase 2 |
| ABCC1 | Multidrug resistance-assoc protein 1 |
| ABCC2 | Canalicular multispecific organic anion transporter 1 |
| ABCG4 | ATP-binding cassette sub-family G member 4 |
| SLCO1A2 | Solute carrier organic anion transporter family member 1A2 |
| SLCO1B1 | Solute carrier organic anion transporter family member 1B1 |
| CYP3A7 | Cytochrome P450 3A7 |
| CYP7A1 | Cytochrome P450 7A1 |
| CYP11B2 | Cytochrome P450 11B1 |
| CYP1A2 | Cytochrome P450 1A2 |
| CYP2C8 | Cytochrome P450 2C8 |
| CYP2C9 | Cytochrome P450 2C9 |
| CYP2C19 | Cytochrome P450 2C19 |
| CYP2D6 | Cytochrome P450 2D6 |
| CYP3A4 | Cytochrome P450 3A4 |
| CYP3A5 | Cytochrome P450 3A5 |
| CYP2E1 | Cytochrome P450 2E1 |
| CYP1A1 | Cytochrome P450 1A1 |
| CYP1B1 | Cytochrome P450 1B1 |
| CYP2A13 | Cytochrome P450 2A13 |
| CYP2F1 | Cytochrome P450 2F1 |
| FMO3 | Flavin containing monooxygenase 3 |
| FMO4 | Flavin containing monooxygenase 4, or Dimethylaniline monooxygenase. |
| MAOA | Monoamine oxidase A |
| MAOB | Monoamine oxidase B |
| EPHX1 | Epoxide hydroxylase 1 |
| EPHX2 | Expoxide hydroxylase 2 |
| CES1 | Liver carboxylesterase 1 |
| NQO1 | NAD(PH)H dehydrogenase (quinone 1) |
| NQO2 | NAD(PH)H dehydrogenase (quinone 2) |
| CBR1 | Carbonyl reductase 1 |
| HSD11B1 | 11b-hydroxysteroid dehydrogenase type 1 |
| DCXR | Dicarbonyl/L-xylulose reductase |
| DHRS2 | Dehydrogenase/reductase SDR family member 2 |
| DHRS4 | Dehydrogenase/reductase SDR family member 4 |
| AKR1A1 | Aldo-keto reductase family 1, or aldehyde reductase |
| LTB4DH | Leukotriene B4 12-hydroxydehydrogenase, or prostaglandin reductase 1 |
| ALDH1A1 | Aldehyde dehydrogenase 1 family, member A1 |
| ALDH2 | Aldehyde dehydrogenase 2 family |
| UGT1A1 | UDP-glucuronosyltransferase 1 family, polypeptide A1 |
| UGT1A3 | UDP-glucuronosyltransferase 1 family, polypeptide A3 |
| UGT1A6 | UDP-glucuronosyltransferase 1 family, polypeptide A6 |
| UGT1A9 | UDP-glucuronosyltransferase 1 family, polypeptide A9 |
| SULT1A1 | Sulfotransferase 1A1 |
| SULT1A2 | Sulfotransferase 1A2 |
| SULT1A3/4 | Sulfotransferase 1A3/4 |
| SULT2A1 | Sulfotransferase 2A1 |
| COMT | Catechol-O-methyltransferase |
| TMPT | Thiopurine S-methyltransferase |
| HNMT | Histamine N-methyltransferase |
| NNMT | Nicotinamde N-methyltransferase |
| NAT1 | N-acetyltransferase 1 |
| NAT2 | N-acetyltransferase 2 |
| GSTA1 | Glutathione S-transferase alpha 1 |
| GSTA4 | Glutathione S-transferase alpha 4 |
| GSTM1 | Glutathione S-transferase mu 1 |
| GSTM2 | Glutathione S-transferase mu 2 |
| GSTP1 | Glutathione S-transferase pi 1 |
| GSTT1 | Glutathione S-transferase theta 1 |
| MGST1 | Microsomal glutathione S-transferase 1 |
| MGST2 | Microsomal glutathione S-transferase 2 |
| ABCA2 | ATP-binding cassette sub-family A member 2 |
| ABCA6 | ATP-binding cassette sub-family A member 6 |
| ABCC3 | ATP-binding casette sub-family C member 3, or Canalicular multispecific organic anion transporter 2. |
| ABCG2 | ATP-binding cassette sub-family G member 2 |
| ABCB1 | ATP-binding casette sub-family B member 1 |
| ABCC4 | ATP-binding casette sub-family C member 4 |
| SLC22A1 | Solute carrier family 22 member 1 |
| SLCO1B3 | Solute carrier organic anion transporter family, member 1B3 |
| SLC10A2 | Solute carrier family 10, member 2 |
| ABCG5 | ATP-binding cassette sub-family G member 5 |
| ABCG8 | ATP-binding cassette sub-family G member 8 |
| ABCB11 | ATP-binding cassette sub-family B member 11 |
| CAR | Constitutive androstane receptor |
| RXRa | Retinoid X receptor alpha |
| FXR | Farnesoid X receptor, or bile acid receptor |
| AhR | Aryl hydrocarbon receptor |
| PXR | Pregnane x receptor |
| RARa | Retinoic acid receptor alpha |
| HNF4a | Hepatocyte nuclear factor-4 alpha |
| HNF4g | Hepatocyte nuclear factor-4 gamma |
| Alb | Albumin |
| ACTB | Actin B |
| TFRC | Transferrin receptor |

In an initial experiment, RNA isolated from day 10 3D HEP/FIB+LEC, 3D HEP/FIB and 2D HEP/FIB mimetics was extensively characterized for comparative drug metabolism enzyme expression and functions in vitro (DonorA). A high-throughput 'Luminex' PCR assay enabled multiplex analysis of 86 genes per sample, including genes encoding Phase I detoxification enzymes, Phase II conjugating enzymes, Phase III transporters, several key transcription factors, and albumin, illustrated by the heatmap in (FIG. 2a). Comparing 2D and 3D HEP/FIB mimetics, it was found that 3 of 6 nuclear receptors, 31 of 36 Phase I including CYP450s, 20 of 22 Phase II, and 17 of 17 Phase III genes were comparable or upregulated in 3D HEP/FIB and 3D HEP/FIB+LEC compared to 2D HEP/FIB (FIG. 2b). Exposure to prototypic CYP3A4 inducer rifampin (RIF) upregulated CYP3A4 in both 2D and 3D culture, and additionally upregulated CYP2A6, CYP2C9, CYP3A7, GSTA1, UGT1A9, EPHX1 and others (FIG. 2c). Importantly, CYPs 3A4, 1A2, 2D6, 2E1 and the 2C isoforms, which collectively metabolize >90% clinical drugs, were highly expressed in 3D mimetics.

To validate gene expression studies and test the utility of engineered human livers for predicting clinical drug-drug interactions, the engineered human livers were treated with omeprazole (OME) or RIF, inducers of CYP1A2 and CYP3A4 respectively, and assessed CYP450 enzymatic activity upon exposure to known substrates (FIG. 2d). Compared to the vehicle control DMSO, OME induced the CYP1A2-mediated metabolism of ethoxyresorufin (ER) 11.5±2.0-fold, but had only a minimal effect on the CYP3A4-mediated metabolism of testosterone (TEST). Conversely, RIF induced the metabolism of TEST by 13.7±2.9-fold, but had no effect on the metabolism of ER. Human liver mimetics, or HEALS, also responded to clinical inhibitors of CYP2A6 and CYP2D6 (FIGS. 2e and 2f). In further experiments, exposure to in vivo rifampin induced the Phase II metabolic activity of HEALs, measured by assessing the conversion of 7-hydroxycoumarin (7-HC, 100 µM) to 7-hydroxycoumarin glucuronide (7-HCG) by uridine diphosphate glucuronyltransferase (UDP-GT) over 2 h. An approximate 4-fold induction was observed following exposure to RIF as compared to a DMSO control. In further experiments, HEALs were extracted and analyzed for albumin secretion (as compared to in vivo human serum albumin secretion levels. Explanted HEALS consistently secreted comparable levels of albumin when tested at 2 days post explantation, evidencing maintained viability of the hepatocytes in the scaffold. Based on these results, human liver mimetics can be used to investigate the downstream effects of CYP450 induction or inhibition on the metabolism of concomitantly administered medications.

Similar data was generated from like samples from a second donor (Donor B) to allow for more detailed evaluation of gene expression profiles. Comparing the relative gene expression between 2D and 3D cultures for the two donors (from independent experiments, Donor A and B), it was found that, on average, 7/7 nuclear receptors, 34/36 phase I [including cytochrome P450 superfamily enzymes (CYP450s)], 11/22 phase II, and 16/17 phase III genes showed similar or higher levels of expression in 3D HEP/FIB HEALs, compared to the 2D HEP/FIB control (FIG. 2h). Importantly, CYP3A4, 1A2, 2D6, 2E1, and the 2C isoforms, which collectively metabolize >90% clinical drugs, were expressed in HEALs established from both donors. These results indicate that relevant human enzymes are expressed in 2D and 3D hepatocyte cocultures and demonstrate the potential use for HEALs in comprehensive and patient-specific profiling of drug-metabolizing enzyme expression and induction.

Additional experiments were performed to compare the mRNA levels of HEALs to an additional adult liver sample. RNA was harvested from adult primary human hepatocytes which were freshly thawed from the cryopreserved donor batch used to fabricate HEALs. This source represents the most relevant 'fresh' adult liver control for profiling drug metabolism enzyme (DME) gene expression, as DME transcripts can vary substantially among donor batches (Lamba J K, Lin Y S, Schuetz E G, & Thummel K E (2002) Genetic contribution to variable human CYP3A-mediated metabolism. Adv Drug Deliv Rev 54(10):1271-1294). Furthermore, gene expression in dispersed cells from the liver, such as those isolated just before cryopreservation, has been shown to be comparable to the intact liver of origin.

Comparative gene expression levels of 83 human-specific DME genes in adult liver samples ('Adult hep'), 3D HEP/FIB HEALs ('3D') and 3D HEP/FIB+LEC HEALS ('3D+') were assessed in a single Luminex multiplex PCR assay and represented in heatmap display (FIG. 2i). Looking specifically at the CYP450 genes and their regulators, nuclear receptors AhR, PXR, and CAR and the CYPs responsible for metabolizing most clinical drugs are expressed at high levels in 3D and 3D+ HEALs (black bars) relative to the adult liver control (gray bars) (FIG. 2j). Table 2 summarizes the overall results: 5 out 7 nuclear receptors, 22 out of 36 Phase I genes, 12 out of 22 Phase II genes, and 17 out of 17 Phase III genes could be classified as conserved or upregulated in 3D HEALs compared to same-donor, freshly thawed adult human hepatocytes. Column 1 lists genes conserved or upregulated and column 2 lists genes down-regulated.

TABLE 2

| | | | | |
|---|---|---|---|---|
| Nuclear Receptors | AhR | | FXR | |
| | CAR | | RXRa | |
| | PXR | | | |
| | RARa | | | |
| | HNF4g | | | |
| Phase I | CYP1A1 | CYP11B2 | CYP2A6 | |
| | CYP1A2 | FMO3 | CYP2C8 | |
| | CYP1B1 | FMO4 | CYP2C9 | |
| | CYP2A13 | MAOA | CYP3A4 | |
| | CYP2B6 | MAOB | CYP3A5 | |
| | CYP2C19 | NQO1 | ALDH1A1 | |
| | CYP2D6 | NQO2 | ALDH2 | |
| | CYP2E1 | CBR1 | DCXR | |
| | CYP2F1 | HSD11B1 | AKR1A1 | |
| | CYP3A7 | DHRS2 | LTB4DH | |
| | CYP7A1 | DHRS4 | CES1 | |
| | | | CES2 | |
| | | | EPHX1 | |
| | | | EPHX2 | |
| Phase II | UGT1A1 | NAT2 | UGT1A3 | |
| | UGT1A6 | GSTA4 | UGT1A9 | |
| | SULT1A3/4 | GSTM1 | SULT1A1 | |
| | TMPT | GSTM2 | SULT1A2 | |
| | HNMT | GSTP1 | SULT2A1 | |
| | NAT1 | MGST2 | COMT | |
| | | | NNMT | |
| | | | GSTA1 | |
| | | | GSTT1 | |
| | | | MGST1 | |
| Phase III | ABCA2 | ABCG4 | | |
| | ABCA6 | ABCG5 | | |
| | ABCB1 | ABCG8 | | |
| | ABCB11 | SLCO1A2 | | |
| | ABCC1 | SLCO1B1 | | |
| | ABCC2 | SLCO1B3 | | |
| | ABCC3 | SLC10A2 | | |
| | ABCC4 | SLC22A1 | | |
| | ABCG2 | | | |

Differences between HEALs and freshly thawed hepatocytes are expected, as livers are harvested from patients at the end-of-life and often exposed to a number of unknown medications which could impact their metabolic activity. Furthermore, it is well established that primary hepatocytes take several days to reach steady-state functional transcript levels following the trauma of isolation and culturing (Guillouzo A (1998) Liver cell models in in vitro toxicology. Environ Health Perspect 106 Suppl 2:511-532). In anticipation of this, 10 2D hepatocyte co-cultures were selected for use, which we have previously determined to exhibit a steady-state rate of hepatocyte function (albumin secretion) approaching in vivo levels (Khetani S R & Bhatia S N (2008) Microscale culture of human liver cells for drug development. Nat Biotechnol 26(1):120-126), as a more robust positive control. Additionally, the analysis has been expanded using this control to assess 2D versus 3D differences for HEALs made from multiple hepatocyte donors. This comprehensive data set, taken together with the enzymatic activity data described above, strongly support the utility of HEALs for generic or personalized drug development studies.

In further experiments, human fetal liver cells were used as the parenchymal cell source. As these cells often are contaminated with surrounding non-parenchymal cells upon isolation using art recognized techniques, encapsulation was performed with both mixed populations (i.e., human fetal liver cells with isolated contaminating non-parenchymal cells) as also encapsulated after additional purification step to enhance purity.

Example 4

Humanized Mice Via Ectopic Implantation and Functional Assessment of Human Liver Mimetics In Vivo To explore the capacity of human liver mimetics for humanized in vivo models, human liver mimetics were implanted at multiple ectopic sites in athymic nude mice. Human liver mimetics reporting luciferase under the human albumin promoter were created (FIG. 3a) and functionally monitored within both subcutaneous and intraperitoneal cavities (FIG. 3b). Whole-animal bioluminescence imaging and quantitation of reporter albumin-luciferase HEP/FIB+ LEC mimetics indicated that the intraperitoneal site could support hepatic survival and albumin expression for several weeks and up to 3 or more months (FIGS. 3b and 3c). Serum analysis from humanized mice confirmed production and secretion of human albumin (FIG. 3d) and alpha-1-antitrypsin (A1AT) (FIG. 3e), suggesting connection to mouse circulation. Notably, A1AT was detected at significant levels above control animals without implants, and in both athymic nude mice (shown over 7 days) (FIG. 3e) and immunocompetent C57/BL6 mice (shown on day 2 post-implantation) (FIG. 3f). Based on the qualitative inspection of vessels supplying implants at day 6 or greater, engraftment of human liver mimetics in vivo was highly efficient (91.6% of n=131 mice engrafted with human livers). Vascular casting at day 35, followed by micro-CT angiography of extracted liver mimetics enabled quantitative analysis of host vessel recruitment to, around and penetrating the implant (FIG. 3g).

These results demonstrate the novel finding that biomaterials engineered to pre-stabilize primary hepatocytes prior to implantation can prime cells for delivery to ectopic sites in mice, and further indicate an ability to protect implanted cells from death due to anoikis, loss of cellular signaling or compromised oxygen transport during engraftment, and also decreases dependence on hepatotrophic factors from the portal vein. To date, mice with chimeric livers have only been successfully established on transgenic liver-injury backgrounds, in which high-quality hepatocytes with a strong selective advantage can home from the injection site to the mouse liver, engraft and, over weeks to months, grow with variable efficiencies.

Here, it was surprisingly shown that, in less than one week, reproducible fabrication of human liver mimetics from two cyropreserved primary donors for implantation in mice were generated (FIGS. 4a, 4b, and 4c). This work further provides the first demonstration of humanized mice established on diverse, non-liver-injury backgrounds (FIG. 4d).

Example 5

Humanized Mice are Predictive of Human Drug Metabolism

The drug-metabolism profile of human liver mimetics (HEALs) and the relatively facile generation of humanized mice through their implantation suggested the potential for in vivo preclinical studies. Major metabolites can pass undetected in standard animal models due to differences in drug metabolism pathways among species. Upon discovery in man, major metabolites require new preclinical phase evaluation and contribute to an alarming rate of prelaunch failures.

To assess whether diverse engineered humanized mice could be useful for preclinical drug metabolism studies and identification of 'major' human metabolites, athymic nude or immune-competent C57/BL6 mice were treated with drugs probing human CYP2A6 or CYP2D6 activity by intraperitoneal and oral routes of administration. The CYP2A6 probe coumarin is primarily metabolized by humans to 7-hydroxycoumarin (7-HC), but preferentially metabolized to coumarin-3,4-expoxide by the 1a1/2 and 2e1 cyp isoforms in mice, while the CYP2D6 probe debrisoquine is metabolized to 4-hydroxydebrisoquine (4-OHDB) in humans and not metabolized in mice. Importantly, the human CYP2D6 gene is responsible for metabolism of 25% of known drugs and, due to its high polymorphism, contributes to pronounced interindividual variability (up to 30-40-fold differences) in the disposition of many xenobiotics. Indeed, debrisoquine hydroxylation genotyping and phenotyping is used to classify patients as clinical poor, intermediate, extensive or ultra-rapid metabolizers. Thus, both CYP2D6 mRNA expression and enzymatic activity of our two human hepatocyte donors was assessed in vitro (FIG. 4b) and the poorer metabolizer was implanted in C57/BL6 mice for comparison to background mouse metabolic activity. Following coumarin or debrisoquine exposure, serum or urine was sampled for quantitation of drug parent and metabolite concentrations by liquid chromatography (LC)/MS/MS. Humanized mice were found to metabolize parent compounds to metabolites significantly more than wild-type mice, according to pharmacokinetic profiles (FIGS. 4e, 4f, 4h and 4i). For debrisoquine, the metabolic ratios (metabolite exposure over parent drug exposure, based on the area under the curve (AUC)) in humanized mice fall within the range of clinical reports for debrisoquine hydroxylation; however, studies on the pharmacokinetics of coumarin hydroxylation in humans have reported up to twice the metabolic ratio as that determined in our engineered humanized mouse (FIG. 4g). The latter may be due to the contribution of CYP2A6 expressed in non-hepatic tissues, which would not be recapitulated in humanized liver mice. Despite this discrepancy, pharmacokinetic analysis of humanized mouse profiles could correctly classify 7-HC and 4-OHDB as 'major' human metabolites, defined as a metabolic ratio of >0.1 by the FDA, while wild-type mouse could not (FIG. 4g). Disproportionate human metabolites that are not detected in animal models contribute to an alarming rate of pre-launch failures, because they must be evaluated as new compounds subject to pre-clinical tests upon their discovery in man. Thus, the novel humanized mice of the instant invention, which were established via tissue-engineering could lower clinical trial attrition rates by helping to identify potentially hazardous metabolites earlier in the drug development pipeline, without patient exposure.

Example 6

Humanized Mice are Predictive of Drug-Drug Interactions and Toxicity

The ability of engineered humanized mice (HEAL-humanized mice) to probe clinical drug-drug interactions was next analyzed. Drug-drug interactions are critical determinants of drug efficacy and safety due to the potential for CYP450-inducing or CYP450-inhibiting drugs to alter the therapeutic or toxic effect of concomitantly administered compounds. In particular, the ability of engineered humanized mice to probe clinical drug-drug interactions that may occur when one CYP450-inducing or -inhibiting drug alters the therapeutic or toxic effect of a second drug was characterized. Systemically, the mice were exposed to CYP3A4 inducer rifampin, then the downstream effects were assessed by analyzing explanted mimetics or mouse serum. The ability to extract mimetics and probe in vivo-induced human livers using standard P450 assays proved useful for testing a variety of drug-drug effects. In response to intraperitoneal RIF, explants exposed to the 3A4 fluorogenic substrate 7-benzyloxy-4-trifluoromethylcoumarin exhibited a 5.1 (±2.3)- to 9.4(±0.4)-fold up-regulation of CYP450 activity in the first week of RIF induction and a 11.1(+0.1)-fold upregulation in the second week of RIF induction (FIGS. 5a, 5b, 5d and 5e). Explants exposed to RIF could also metabolize testosterone (TEST) at 5.9(±0.6) fold-induction over explants from DMSO-treated mice, while ethoxyresorufin (ER) metabolism mediated by CYP1A2 was not induced (FIG. 5b).

To explore the utility of the humanized mouse for predicting toxic drug-drug interactions in vivo, RIF-induced or non-induced (DMSO treated) humanized mice were dosed with therapeutic levels of acetaminophen (APAP) and human hepatotoxicity was assessed. Acetaminophen (APAP) is a common analgesic that is severely hepatotoxic at high doses due to the CYP450-mediated formation of the reactive metabolite N-acetyl-p-benzoquinone (NAPQI), but innocuous at therapeutic doses due to detoxification of NAPQI by cellular glutathione. Four hours after oral APAP administration, mice that had been pre-induced with RIF showed evidence of human hepatocellular injury, while mice exposed to only APAP or RIF exhibited human serum albumin levels similar to untreated controls (FIG. 5c and FIG. 5f). Mouse livers exposed to RIF, APAP or RIF+APAP appeared uninjured based on serum liver function enzyme tests and histopathological analysis of mouse liver sections (FIGS. 5g-i). Humanized mice containing human liver mimetics expressing a broader complement of drug metabolism genes (other CYP450s, transcription factors, transporters) could therefore be useful for screening hepatotoxic drug-drug combinations and doses by multiple administration routes in vivo.

The instant invention has thus established a novel humanized mouse model and demonstrated its utility for predicting human drug responses, pharmacokinetics upon multiple routes of administration, and metabolite formation in vivo. Unlike current transgenic and transplantation approaches, engineered humanized mice can be generated rapidly (<2 weeks), at high yield and reproducibility, and using mice with non-liver injury genetic backgrounds. The instant invention also enables applications beyond drug safety, as extension to disease mouse models or models with different immunities could be useful for the development of therapies for diverse diseases. In addition, the instant invention has further demonstrated the feasibility of implanting human liver mimetics in immune-competent (Swiss Webster, C57/BL6) mice (FIGS. 5j and 5k), and the micro-engineered polymer scaffold may serve as not only a supportive microenvironment for hepatocytes but a delivery vehicle and potential immunoisolatory (rejection-delaying) barrier. This work also indicates that the incorporation of multiple and multiplexed implanted engineered livers can be used to compare different patient responses in one animal. The model animals of the instant invention may also prove useful for the study of immune-mediated toxicity, idiosyncratic toxicity, and gut-liver interactions, Example 7

3D Huh 7.5 Construct Encapsulation and Viability In Vitro and In Vivo

Towards engineering mice with implantable liver constructs for HCV infection, the utility of the photopolymerizable, polyethylene-glycol (PEG)-based scaffold for the encapsulation and implantation of HCV-infectible Huh 7.5 human hepatoma cells was explored. In vitro, Huh 7.5 human hepatoma cells have been widely used for their high susceptibility to hepatitis C virus infection; however, the direct transplantation of Huh 7.5 cells in the subcutaneous or peritoneal cavities of mice results in rampant tumor formation, and resultant tumors—which become necrotic as they lose accessibility to host vessels—have not been able to support long-term HCV infection in vivo. It was hypothesized that encapsulating Huh 7.5 cells in tunable polyethylene glycol-diacrylate (PEG-DA) hydrogel networks commonly used for tissue-engineering applications would facilitate the transplantation of controllable densities of Huh 7.5 which would survive for longer periods of time (weeks) in vivo and, further, could be engineered to support HCV infection.

Figure 6B:
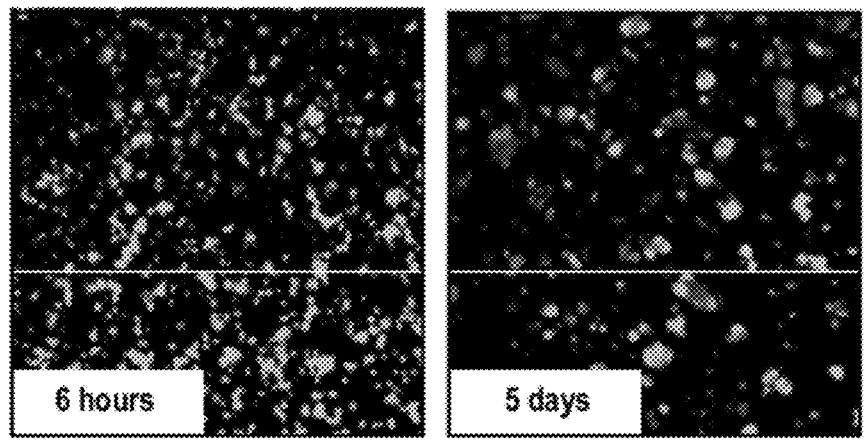
Figure 6C:
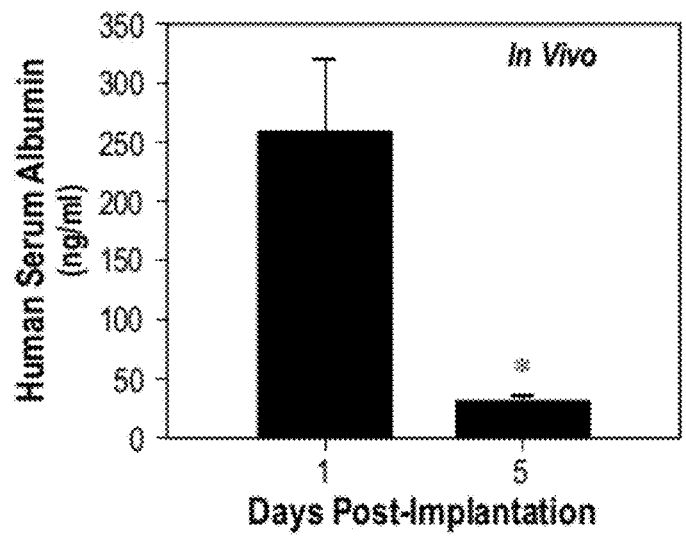

As a first step, Huh 7.5 were encapsulated at a density of $8 \times 10^6$ cells/ml within unmodified PEG-DA networks (20 kDa chain length, 10% w/v polymer) (FIG. 6A) and assessed the viability of 3D Huh 7.5 over time in vitro. Using a calcein AM/ethidium-homodimer Live/Dead stain and epifluorescence imaging, it was found that 3D encapsulated Huh 7.5 exhibited negligible toxicity at 6 hours after encapsulation (FIG. 6B), suggesting minimal cell death by free radical damage during photopolymerization. Over five days of in vitro culture, cells maintained similar levels of viability, but viable cells on Day 5 had coalesced and/or proliferated into spheroidal cell clusters within the 3D matrix (FIG. 6B). The spheroidal morphology was consistent with the growth pattern and morphology of other PEG-encapsulated hepatoma cells, based on previous experience encapsulating hepatic cells from multiple stages of differentiation (primary rat and human hepatocytes, progenitor liver cells and HepG2 hepatoma cells). After confirming viability of 3D Huh 7.5 constructs over time in vitro, the constructs were implanted in athymic nude (NCR nu/nu) mice and construct survival was assessed over time in vivo. Constructs were amenable to facile implantation in the intraperitoneal site of nude mice. However, serum from test mice analyzed for the hepatic functional marker human albumin showed a decline in Huh 7.5 function from one- to five-days post-implantation (FIG. 6C), and, thus, optimization conditions for the PEG-based constructs were further investigated.

Example 8

Optimizing 3D Huh 7.5 Constructs for Engraftment In Vivo

Previously, the inventors had discovered that primary hepatocytes were dependent on cell-cell and cell-matrix interactions presented within PEG-DA hydrogels for stability in vitro, as well as engraftment and functional maintenance in vivo. Although Huh 7.5 did not appear to require these microenvironmental cues to be viable over one week of in vitro culture, it was considered that in vivo carcinoma cells are often associated with tumor stroma, and that interactions between stromal fibroblasts and Huh 7.5 have been found to influence tumor cell growth and migration in mouse models. Thus, to improve 3D Huh 7.5 construct engraftment in nude mice, the incorporation of the supportive stromal J2-3T3 murine fibroblast line with Huh 7.5 encapsulated within implantable PEG networks was explored. Further, utilizing the chemical tunability of PEG-based hydrogels to present matrix-derived peptides for cell adhesion and receptor ligation, the fibronectin-derived RGDS peptide was conjugated to acrylate PEG monomers and tested the influence of RGDS on Huh 7.5 functions and engraftment, with and without J2-3T3 fibroblast co-culture.

Figure 7A:
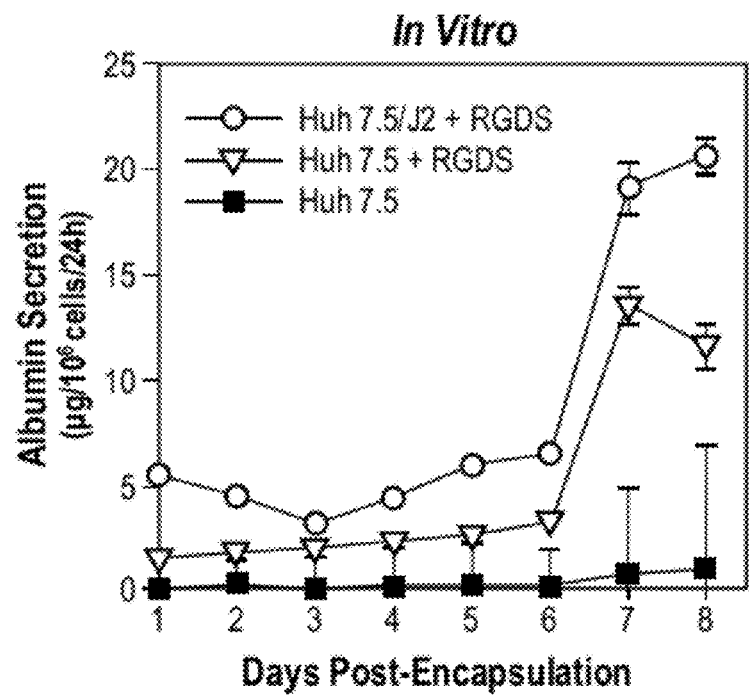
Figure 7B:
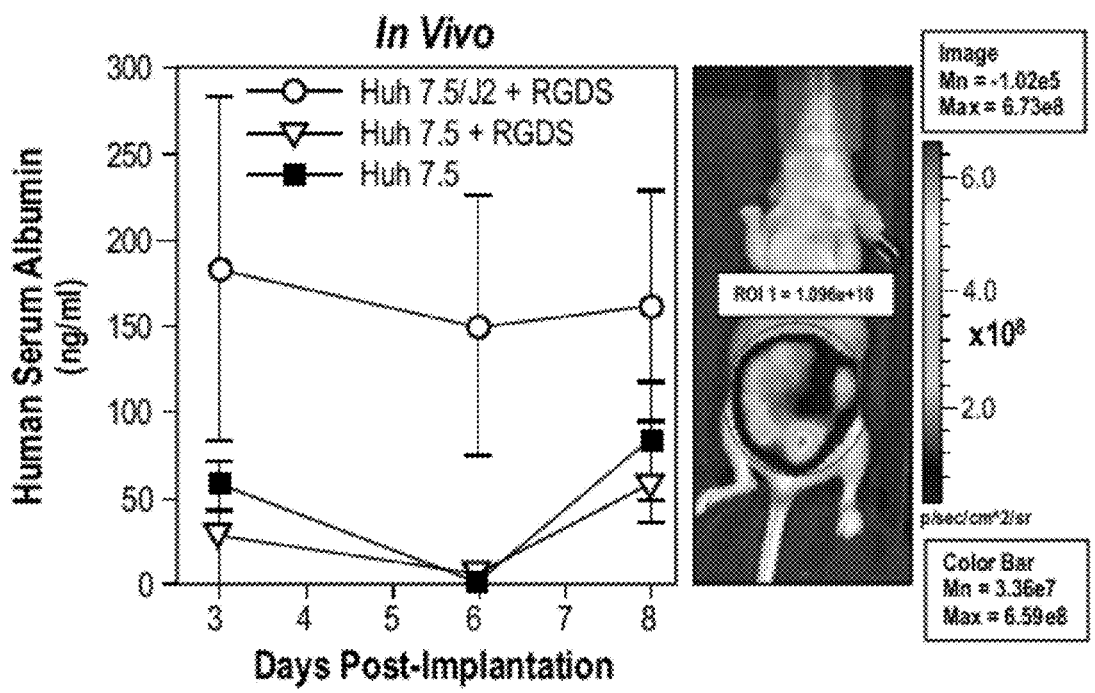

In vitro, co-cultivation of 0.4×10⁶/ml Huh 7.5 with 0.4× 10⁶/ml J2-3T3 for one-week prior to encapsulation in PEG+ RGDS hydrogels at a 8×10⁶ Huh 7.5/ml final density improved human albumin secretion functions compared to Huh 7.5 encapsulated at the same density alone, independent of RGDS (FIG. 7A). More importantly, the combination of J2-3T3 co-culture and RGDS improved 3D culture engraftment over one week in vivo, as assessed by comparing levels of human albumin in the serum (FIG. 6.2B) over time. Bioluminescence imaging of reporter Huh 7.5, Huh 7.5/J2 and Huh 7.5/J2+RGDS constructs (fabricated using Huh 7.5 cells stably transduced to express a human albumin promoter-driver firefly luciferase gene), correlated with these trends; a representative image of mice transplanted with Huh 7.5/J2+RGDS construct and imaged on day 8 is shown in FIG. 7B. Therefore, the local microenvironment of the PEG-DA hydrogel scaffold could be modulated to incorporate cell-cell and cell-matrix interactions important for ensuring encapsulated Huh 7.5 engraftment in a nude mouse model. These interactions likely influence Huh 7.5 engraftment through multiple mechanisms, including improved maintenance of Huh 7.5 phenotype, improved Huh 7.5 adhesion, migration and proliferation, and improved host vessel recruitment to angiogenic factors secreted from J2-3T3 fibroblasts.

Example 9

HCV Infection of 3D Huh 7.5 Constructs In Vitro

To assess the potential for 3D Huh 7.5 constructs to be infected with HCV upon implantation in mice, constructs were exposed to 0.125 MOI of hepatitis C virus encoding a secreted Gaussia luciferase (Gluc) reporter, and luciferase activity was monitored in culture supernatant over time. Infectious virus was detected at 3 days and up to 1 week following construct infection (FIG. 8), demonstrating that virus particles can enter the PEG-DA matrix, infect encapsulated Huh 7.5 cells, replicate, translate proteins and secrete Gluc protein for detection in supernatant. Interestingly, the calculated mesh size of the PEG-DA network at the polymerization conditions used here (20 kDa chain length, 10% w/v) is only 70 Å and could not theoretically permit diffusion of large ~50 nm HCV particles. These results are consistent with other literature reports that hepatitis C virus and lentivirus particles 50-100 nm in size permeate through PEG-DA networks as small as 50 Å mesh size (8 kDa chain length, 10% w/v). Although the precise mechanism of this phenomenon has not been established, artisans in this field have postulated that the photo-encapsulation of particles, cells, and other porogens, can alter local PEG chain network formation, causing polymer defects and significantly increasing the effective hydrogel porosity.

Figure 9B:
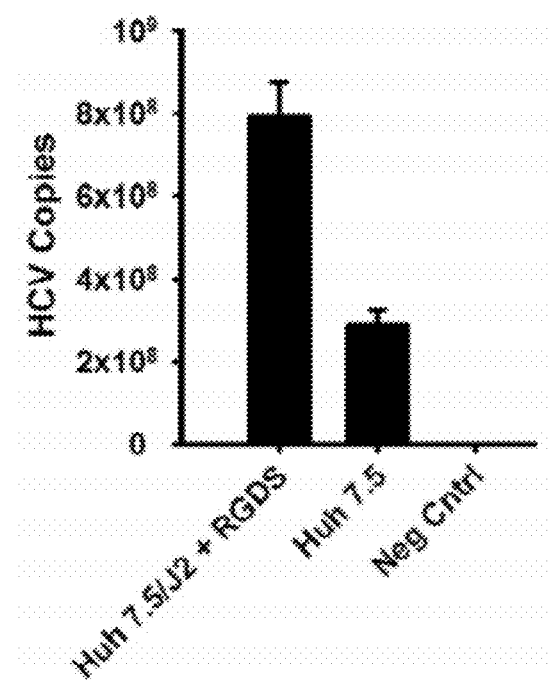

To further characterize and quantify the infectivity of Huh 7.5 constructs following optimization with J2-3T3 fibroblast co-culture and RGDS peptide conjugation, Huh 7.5 constructs were infected with HCV reporter virus encoding red fluorescence protein (RFP) and infection was assessed qualitatively using epifluorescence microscopy. Additionally, total RNA was harvested from infected Huh 7.5 constructs and Q-PCR methods were performed to quantify HCV copies present within encapsulated Huh 7.5 cells. Consistent with the results using the Gluc reporter, it was found that HCV particles could diffuse into the PEG-DA network and robustly infect encapsulated Huh 7.5. Infected Huh 7.5 constructs exhibited measurable levels of reporter RFP activity (FIG. 9A) and up to ~3×10⁸ copies/ml HCV RNA (FIG. 9B), while uninfected negative control constructs showed no red fluorescence and null copy detection of HCV RNA. It was further determined that Huh 7.5 constructs optimized for engraftment in vivo with J2-3T3 stromal fibroblasts and RGDS peptide presentation yielded improved, brighter HCV-RFP signal (FIG. 9A) and ~2.7-fold increased copy numbers of HCV per ml total RNA (FIG. 9B). It is believed that the mechanism explaining the improved infectivity of Huh 7.5 following encapsulation with stromal cells and matrix-derived peptides may be related to differences in Huh 7.5 viability, phenotype, growth rate, morphology, or polarity.

Example 9 demonstrates the development and optimization a biomaterial platform for the encapsulation and implantation of Huh 7.5 constructs, characterized the in vitro infectivity of Huh 7.5 constructs using a broad array of HCV reporter viruses, These findings can assist researchers in the study of the pathogenesis of HCV in physiologic settings. The models are predicted to be equally suitable for integration of human liver implants with immune-competent mice or mice with humanized immune systems. Humanized mouse models established with primary human hepatocytes, as described above, and integrated with humanized immune system mice, can help elucidate how individuals mount an immune response, how virus persists or resolves, and how stimulation of the immune system eliminates virus. Mice humanized with simple Huh 7.5 construct implants can readily serve as potential sources of highly infectious virus particles, or as test beds to screen novel anti-viral therapies.

Example 10

Alginate—a Macroporous Hydrogel—Supports In Vitro 3D Culture of Primary Adult Human Hepatocytes To solve transport issue (of sporozoites into hydrogels), alginate was used as a model material that has pores that allow sporozoite traversal. Primary adult human hepatocytes and J2 stromal fibroblasts were seeded in lyophilized alginate sponges selected for pore sizes that would allow malaria sporozoites to access the encapsulated hepatocytes (FIG. 10a). J2 stromal fibroblasts were included to maintain albumin secretion of primary adult human hepatocytes encapsulated in alginate for 20 days (FIG. 10b). Phase contrast imaging (FIG. 10c, left panel) and H&E staining (FIG. 10c, right panel) demonstrated viable culture of primary human hepatocyte/fibroblast aggregates in alginate. These data demonstrate that primary human hepatocytes can be supported in such hydrogels by coculture with fibroblasts.

Example 11

Figures 11A, 11B:
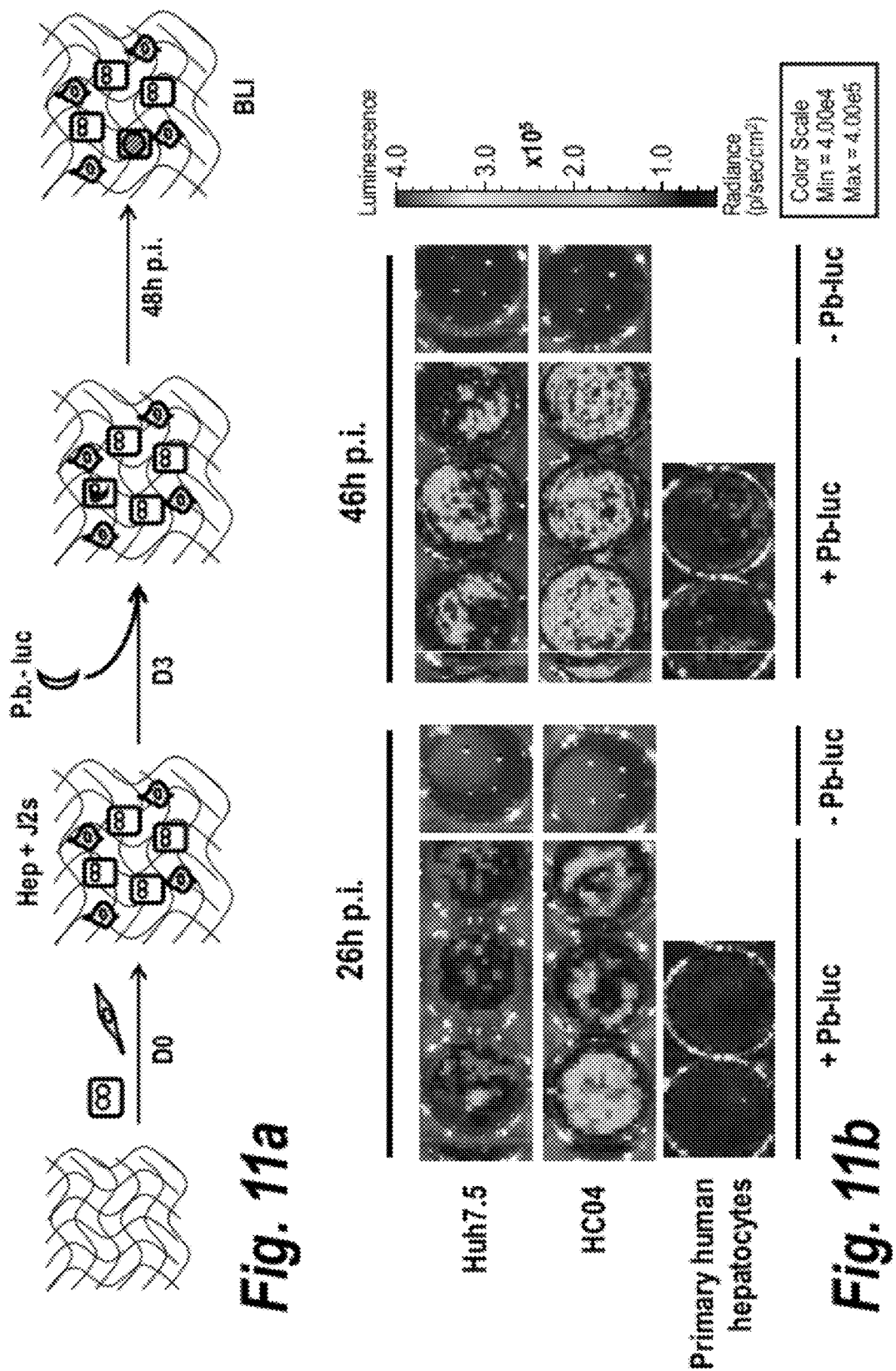

Alginate Supports In Vitro Infection of Encapsulated Hepatoma or Cocultured Human Hepatocytes by *P. Berghei*-Luciferase Primary adult human hepatocytes and J2 stromal fibroblasts were seeded in lyophilized alginate sponges and infected with luciferase-expressing *Plasmodium berghei* (Pb-luc) three days post-seeding. Bioluminescence imaging was performed two days post-infection (FIG. 11a). Bioluminescence imaging of hepatoma cells Huh7.5 and HC04 as well as primary human hepatocytes indicated successful infection with Pb-luc 26 h and 46 h post-infection (FIG. 11b).

Figure 12A:
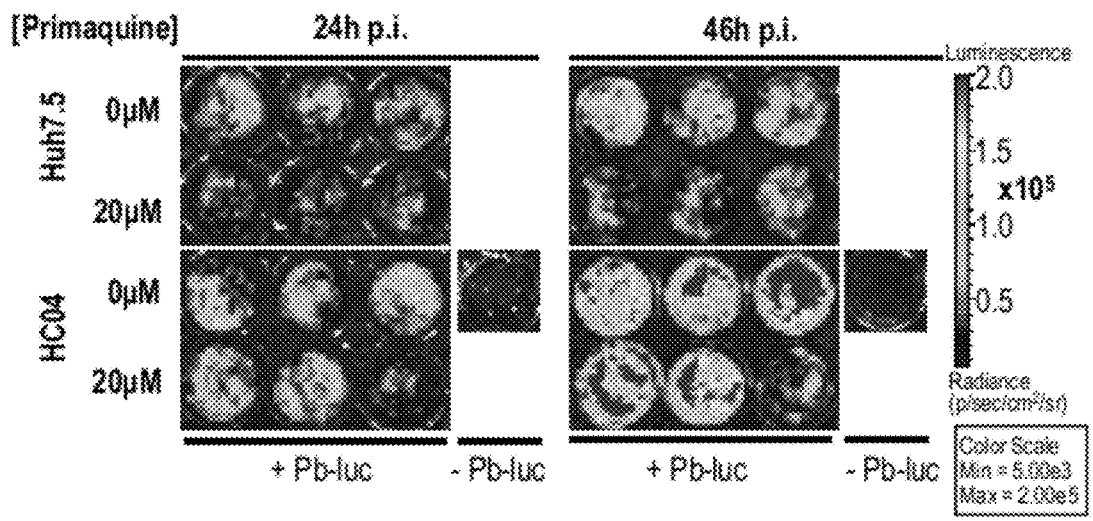
Figure 12B:
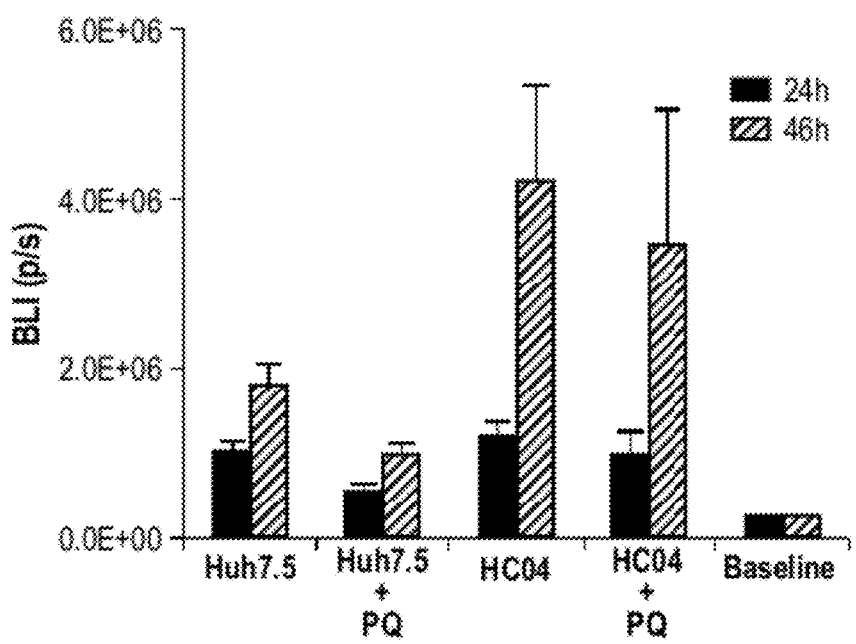

Next, the response of Pb-luc-infected hepatoma aggregates in alginate to primaquine treatment was tested. Bioluminescence imaging of hepatoma cells Huh7.5 and HC04 infected with Pb-luc and treated with primaquine, a liver-stage specific antimalarial drug was performed (FIG. 12a.) Quantification of BLI imaging showing that primaquine had a greater effect on inhibiting parasite development in Huh7.5 than in HC04 (FIG. 12b.) These data, collectively, evidence the usefulness of the constructs of the invention in a model system for studying malaria infection, as well as the suitability of such systems, for example, in screening and studying potential anti-malarial therapeutics.

Using pre-infected humanized mouse models, studies can be performed to characterize the kinetics of viral persistence, as well as assess viral clearance and clinical outcomes over time. Additionally, experiments can be performed to compare and contrast the infectivity of humanized mouse-derived and construct culture-derived HCV, as virions from animal-versus cell-sources that have been reported to have different biophysical properties influencing infectivity. Additionally, cohorts of pre-infected humanized mice can be generated to test against a panel of anti-viral combination therapies, as validation for their utility in drug screening.

EQUIVALENTS

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the invention, and exclusive use of all modifications that come within the scope of the appended claims is reserved. It is intended that the present invention be limited only to the extent required by the appended claims and the applicable rules of law.

All literature and similar material cited in this application, including, patents, patent applications, articles, books, treatises, dissertations, web pages, figures and/or appendices, regardless of the format of such literature and similar materials, are expressly incorporated by reference in their entirety. In the event that one or more of the incorporated literature and similar materials differs from or contradicts this application, including defined terms, term usage, described techniques, or the like, this application controls. Such equivalents are intended to be encompassed by the following claims.

We claim:

1. An implantable human liver tissue construct, comprising:
(a) a biocompatible, porous hydrogel scaffold comprising one or more cell adhesive peptides,
(b) a population of cells comprising human hepatocytes and non-parenchymal cells seeded on the hydrogel scaffold of (a), wherein the non-parenchymal cells support hepatocellular viability and function; and
(c) a population of cells comprising human liver-derived non-parenchymal cells seeded on the hydrogel scaffold of (a),
wherein the cell populations of (b) and (c) are encapsulated in (a) in a pattern to prevent physical contact between the cell populations of (b) and (c).

2. The construct of claim 1, wherein the hepatocytes are infected with a human liver-trophic pathogen.

3. The construct of claim 2, wherein the human liver-trophic pathogen is a virus or a parasite.

4. The construct of claim 3, wherein the virus is HCV or malaria.

5. The construct of claim 1, wherein the hydrogel is photopolymerized polyethylene glycol (PEG) hydrogel.

6. The construct of claim 5, wherein the photopolymerized polyethylene glycol (PEG) hydrogel is a polyethylene glycol-diacrylate (PEG-DA) hydrogel.

7. The construct of claim 1, wherein the non-parenchymal cells are stromal cells.

8. The construct of claim 7, wherein the stromal cells are fibroblasts.

9. The construct of claim 1, wherein the hydrogel contains about $8 \times 10^6$ hepatocytes/ml.

10. The construct of claim 8, wherein the hydrogel contains about $15\text{-}25 \times 10^6$ fibroblasts/ml.

11. The construct of claim 1, wherein the human liver-derived non-parenchymal cells are human liver endothelial cells (LECs).

12. The construct of claim 11, wherein the hydrogel contains about $6 \times 10^6$ LECs/ml.

13. The construct of claim 11, wherein the LECs are TMNK-1 cells.

14. The construct of claim 1, wherein maintenance of hepatocellular viability and function is evidenced by albumin secretion or urea synthesis at levels of at least about 90% relative to starting levels.

15. The construct of claim 1, wherein maintenance of hepatocellular viability and function is evidenced by drug metabolism enzyme expression or function at levels of about 90% relative to starting levels.

16. The construct of claim 1
(a) wherein the construct has a diameter of about 20-mm and a thickness of about 250 µm, the construct comprising about $0.5 \times 10^6$ human hepatocytes;
(b) wherein the hydrogel comprises perfusion channels supporting diffusive transport of oxygen and nutrients;
(c) wherein the scaffold is non-biodegradable; and
(d) wherein the cell-adhesive peptide is an extracellular matrix- (ECM-) derived peptide, optionally covalently attached to a component of the hydrogel.

17. The construct of claim 1, wherein the construct remains viable for at least three, four, six, eight or twelve weeks upon in vivo implantation.

18. The construct of claim 1, wherein the ECM-derived peptide is an RGDS peptide.

19. The construct of claim 1, wherein the construct is explantable.

20. The construct of claim 1, wherein
(a) the construct has a diameter or width of about 5-50 mm; and
(b) the construct has a thickness of about 50-1000 µm.

21. The construct of claim 1, wherein
(a) the construct has a diameter or width of about 5-50 mm;
(b) the construct has a thickness of about 50-1000 µm; and
(c) the construct comprises about 1 to $50 \times 10^6$ human hepatocytes/ml.

22. The construct of claim 1, wherein the construct has a diameter of about 20-mm and a thickness of about 250 µm, and wherein the construct comprises about $0.5 \times 10^6$ human hepatocytes.

23. The construct of claim 1, wherein the hydrogel comprises perfusion channels supporting diffusive transport of oxygen and nutrients.

24. The construct of claim 1, wherein the scaffold is non-biodegradable.

25. The construct of claim 1, wherein the cell-adhesive peptide is an extracellular matrix- (ECM-) derived peptide covalently attached to a component of the hydrogel.

26. The construct of claim 25, wherein one or more of the populations of cells is engineered to express a reporter protein.

27. The construct of claim 1, wherein the ECM-derived peptide is an RGDS peptide covalently attached to an acrylate PEG monomer polymerized in the hydrogel.

28. The construct of claim 1, wherein the hydrogel is patterned to permit diffusion of oxygen and nutrients to the innermost cells.

29. The construct of claim 1, wherein the hepatocytes are primary hepatocytes, progenitor-derived, ES-derived, or induced pluripotent stem cell-derived.

30. The construct of claim 1, wherein the non-parenchymal cells are fibroblasts and the human liver-derived non-parenchymal cells are endothelial cells.

31. The construct of claim 29, wherein the non-parenchymal cells are fibroblasts and the human liver-derived non-parenchymal cells are endothelial cells.

32. The construct of claim 30, further comprising more than one population of fibroblasts.

33. The construct of claim 30, wherein the fibroblasts are normal human fibroblasts.

34. The construct of claim 1, further comprising at least one other cell type.

35. The construct of claim 34, wherein the at least one cell type is a liver cell type selected from the group consisting of Kupffer cells, Ito cells, and biliary ductal cells.

36. The construct of claim 34, wherein the at least one cell type is an immune cell type selected from the group consisting of macrophages, B-cells, and dendritic cells.

37. The construct of claim 1, wherein the hepatocytes are a combination of hepatocytes and liver cells.

38. A method of making an implantable human liver tissue construct, comprising obtaining a co-culture comprising a population of human hepatocytes, a population of non-parenchymal cells supporting hepatocellular viability and function, and a population of human liver-derived non-parenchymal cells, wherein the co-culture has been previously cultured in vitro for a time sufficient to stabilize hepatocyte function; and encapsulating the co-culture in a biocompatible, hydrogel scaffold comprising one or more cell-adhesive peptides, wherein the population of liver-derived non-parenchymal cells are encapsulated in a pattern to prevent physical contact between the hepatocytes and the non-parenchymal cells.

39. The method of claim 38, wherein the hydrogel is photopolymerized polyethylene glycol (PEG) hydrogel, for example, a polyethylene glycol-diacrylate (PEG-DA) hydrogel.

40. The method of claim 39, wherein the non-parenchymal cells are stromal cells.

41. The method of claim 39, wherein the hydrogel contains about $8 \times 10^6$ hepatocytes/ml.

42. The method of claim 40, wherein the stromal cells are fibroblasts and the hydrogel contains about $24 \times 10^6$ fibroblasts/ml.

43. The method of claim 38, wherein the human liver-derived non-parenchymal cells are human liver endothelial cells (LECs), and wherein the hydrogel contains about $6 \times 10^6$ LECs/ml.

44. The method of claim 38, wherein
(a) the construct has a diameter of about 20-mm and a thickness of about 250 μm, the construct comprising about $0.5 \times 10^6$ human hepatocytes;
(b) the hydrogel comprises perfusion channels supporting diffusive transport of oxygen and nutrients;
(c) the scaffold is non-biodegradable; and
(d) the cell-adhesive peptide is an extracellular matrix- (ECM-) derived peptide, optionally covalently attached to a component of the hydrogel.

45. The method of claim 38, wherein the construct remains viable for at least three, four, six, eight or twelve weeks upon in vivo implantation or wherein one or more of the populations of cell is engineered to express a reporter protein.

46. The method of claim 40, wherein the stromal cells are fibroblasts.

47. The method of claim 43, wherein the LECs are TMNK-1 cells.

48. The method of claim 44, wherein the ECM-derived peptide is an RGDS peptide, optionally covalently attached to an acrylate PEG monomer polymerized in the hydrogel.

* * * * *

UNITED STATES PATENT AND TRADEMARK OFFICE
CERTIFICATE OF CORRECTION

Page 1 of 1

PATENT NO.         : 10,004,826 B2
APPLICATION NO.    : 13/267866
DATED              : June 26, 2018
INVENTOR(S)        : Sangeeta N. Bhatia et al.

It is certified that error appears in the above-identified patent and that said Letters Patent is hereby corrected as shown below:

In the Claims

At Column 54, Claim number 18, Line number 47, please replace "The construct of claim 1" with --The construct of claim 16--

At Column 55, Claim number 26, Line number 6, please replace "The construct of claim 25" with --The construct of claim 1--

At Column 55, Claim number 27, Line number 9, please replace "The construct of claim 1" with --The construct of claim 25--

Signed and Sealed this
Second Day of October, 2018

Andrei Iancu
*Director of the United States Patent and Trademark Office*